US012577253B2

(12) United States Patent
Xu et al.

(10) Patent No.: US 12,577,253 B2
(45) Date of Patent: Mar. 17, 2026

(54) 5,6-DIHYDROTHIENO[3,4-H]QUINAZOLINE COMPOUND

(71) Applicant: SHANGHAI FOSUN PHARMACEUTICAL INDUSTRIAL DEVELOPMENT CO., LTD., Shanghai (CN)

(72) Inventors: Yangyang Xu, Shanghai (CN); Wentao Wu, Shanghai (CN); Haizhong Tan, Shanghai (CN); Dongkai Zhang, Shanghai (CN); Jikui Sun, Shanghai (CN); Yang Zhang, Shanghai (CN); Shuhui Chen, Shanghai (CN)

(73) Assignee: SHANGHAI FOSUN PHARMACEUTICAL INDUSTRIAL DEVELOPMENT CO., LTD., Shanghai (CN)

( * ) Notice: Subject to any disclaimer, the term of this patent is extended or adjusted under 35 U.S.C. 154(b) by 423 days.

(21) Appl. No.: 18/276,226

(22) PCT Filed: Jan. 26, 2022

(86) PCT No.: PCT/CN2022/074110
§ 371 (c)(1),
(2) Date: Aug. 7, 2023

(87) PCT Pub. No.: WO2022/166725
PCT Pub. Date: Aug. 11, 2022

(65) Prior Publication Data

US 2024/0140962 A1 May 2, 2024

(30) Foreign Application Priority Data

| | | |
|---|---|---|
| Feb. 8, 2021 | (CN) | 202110172946.6 |
| Jun. 11, 2021 | (CN) | 202110655630.2 |
| Jul. 29, 2021 | (CN) | 202110864387.5 |
| Sep. 27, 2021 | (CN) | 202111137961.3 |
| Nov. 29, 2021 | (CN) | 202111473661.2 |

(51) Int. Cl.
*C07D 495/04* (2006.01)
*A61P 35/00* (2006.01)
*C07D 519/00* (2006.01)

(52) U.S. Cl.
CPC ............ *C07D 495/04* (2013.01); *A61P 35/00* (2018.01); *C07D 519/00* (2013.01)

(58) Field of Classification Search
CPC ...... C07D 495/04; C07D 519/00; A61P 35/00
USPC .................................................... 514/252.02
See application file for complete search history.

(56) References Cited

FOREIGN PATENT DOCUMENTS

| | | | |
|---|---|---|---|
| CN | 1826343 | A | 8/2006 |
| CN | 101484457 | A | 7/2009 |
| CN | 101563351 | A | * 10/2009 |
| CN | 101824043 | A | 9/2010 |
| CN | 101952291 | A | 1/2011 |
| CN | 103097388 | A | 5/2013 |
| CN | 103122001 | A | 5/2013 |
| CN | 118382626 | A | 7/2024 |
| EP | 2010542 | B1 | 1/2012 |
| EP | 3848377 | A1 | 7/2021 |
| JP | 2007502851 | A | 2/2007 |
| JP | 2007509848 | A | 4/2007 |
| JP | 2010536760 | A | 12/2010 |
| JP | 2010540463 | A | 12/2010 |
| JP | 2013532652 | A | 8/2013 |
| JP | 2013533276 | A | 8/2013 |
| JP | 2014503566 | A | 2/2014 |
| JP | 2016515537 | A | 5/2016 |
| WO | 2004104007 | A1 | 12/2004 |
| WO | 2005037843 | A1 | 4/2005 |
| WO | 2008074788 | A1 | 6/2008 |
| WO | 2009023269 | A2 | 2/2009 |
| WO | 2009042806 | A1 | 4/2009 |
| WO | 2009049422 | A1 | 4/2009 |
| WO | 2009112324 | A1 | 9/2009 |
| WO | 2009112524 | A1 | 9/2009 |
| WO | 2012010704 | A1 | 1/2012 |
| WO | 2012013557 | A1 | 2/2012 |

(Continued)

OTHER PUBLICATIONS

Search Report issued in the corresponding JP Application No. 2023-547663, dated Jun. 27, 2024.

(Continued)

*Primary Examiner* — Kahsay Habte
(74) *Attorney, Agent, or Firm* — Morgan, Lewis & Bockius LLP

(57) ABSTRACT

Provided are a series of 5,6-dihydrothieno[3,4-h]quinazoline compounds as represented by formula (P) and pharmaceutically acceptable salts thereof, and the use of the compounds or pharmaceutically acceptable salts thereof in the preparation of solid tumor drugs, such as solid tumor drugs associated with selective PLK1 inhibitors.

(P)

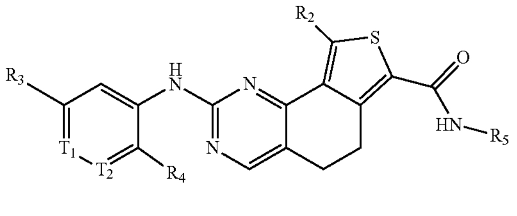

13 Claims, 1 Drawing Sheet

(56) References Cited

FOREIGN PATENT DOCUMENTS

| | | | |
|---|---|---|---|
| WO | 2014145909 | A2 | 9/2014 |
| WO | 2020063788 | A1 | 4/2020 |
| WO | 2020160321 | A1 | 8/2020 |

OTHER PUBLICATIONS

Araki et al., "The Effect of Conformational Flexibility on Binding Free Energy Estimation between Kinases and Their Inhibitors", Journal of Chemical Information and Modeling, 2016, 56:2445-2456.

Apr. 28, 2022 International Search Report issued in International Patent Application No. PCT/CN2022/074110.

Apr. 28, 2022 Written Opinion of the International Searching Authority issued in International Patent Application No. PCT/CN2022/074110.

Dec. 12, 2022, Onvansertib, NMS-1286937, NMS-P937, PCM-075. Copyright Cayman Chemical Company.

Office Action issued in corresponding Chinese Patent Application No. 202280011925.9, dated Mar. 21, 2025.

* cited by examiner

5,6-DIHYDROTHIENO[3,4-H]QUINAZOLINE COMPOUND

This is a National Phase Application filed under 35 U.S.C. 371 as a national stage of PCT/CN2022/074110, filed Jan. 26, 2022, and application claiming the benefit of CN202110172946.6, filed on Feb. 8, 2021, CN202110655630.2, filed on Jun. 11, 2021, CN202110864387.5, filed on Jul. 29, 2021, CN202111137961.3, filed on Sep. 27, 2021 and CN202111473661.2, filed on Nov. 29, 2021 the content of each of which is hereby incorporated by reference in its entirety.

TECHNICAL FIELD

The present disclosure relates to a series of 5,6-dihydrothieno[3,4-h]quinazoline compounds, in particular to a compound of formula (P) and a pharmaceutically acceptable salt thereof.

BACKGROUND

Polo-like kinases (PLKs) are a class of highly conserved serine/threonine protein kinases, each of which has a highly homologous serine/threonine kinase domain at its N-terminal, and a characteristic domain (polobox domain, PBD) regulating PLKs activities and subcellular dynamic localization at its C-terminal. There are many members of the PLKs family, and there are four subtypes in the human body, namely PLK1, PLK2, PLK3, and PLK4, which play a vital role in the regulation of each phase of the cell cycle. Among these four family members, PLK1 is currently the most thoroughly studied. Therefore, PLK1 is a widely concerned target in tumor diagnosis and treatment.

Cardiff Oncology (formerly Trovagene), under license from Nerviano, is developing onvansertib (PCM-075; NMS-P937; nms—1286937; NMS-937) as a fumarate, which is an oral Polo-like kinase precursor (Plk)-1 inhibitor. Onvansertib is a potential oral drug for cancer treatment with indications comprising metastatic colorectal cancer (mCRC), solid tumors, acute myeloid leukemia (AML), and anti-metastatic castration prostate cancer. PLK1 is a potent therapeutic target overexpressed in most cancers, and Onvansertib is a novel, highly selective PLK1 inhibitor.

The PLK1 inhibitor Onvansertib is the first PLK1 inhibitor to enter clinical research, with early clinical research results showing clinical benefit in 88% of KRAS-mutant mCRC patients and demonstrating an acceptable safety profile in clinical studies, with a higher response rate in CRC patients compared to KRASG12C inhibitors and an efficacy against all KRAS mutant subtypes. CRC is the third largest malignant tumor after lung cancer and breast cancer, with a global market of approximately $25 billion in 2018, and therefore, small molecule PLK1 inhibitors with high activity, high selectivity and stable metabolism can be sought for the treatment of tumors.

CONTENT OF THE PRESENT INVENTION

The present disclosure provides a compound of formula (P) or a pharmaceutically acceptable salt thereof (P)

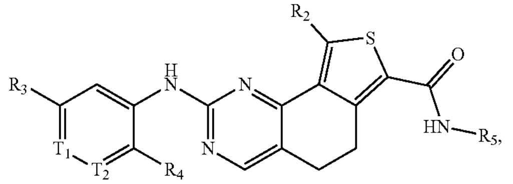

wherein $T_1$ is selected from $CR_1$ and N;

$T_2$ is selected from CH and N;

$R_1$ is selected from H;

$R_2$ is selected from H, CN, $C_{1-3}$ alkyl, $C_{1-3}$ alkoxy, $C_{1-3}$ alkylthiol, $S(=O)_2C_{1-3}$ alkyl, $C_{2-3}$ alkynyl, $C_{3-5}$ cycloalkyl, —O—$C_{3-5}$ cycloalkyl, and 5-membered heteroaryl, and the $C_{1-3}$ alkyl, $C_{1-3}$ alkoxy, $C_{1-3}$ alkylthiol, $S(=O)_2C_{1-3}$ alkyl, $C_{2-3}$ alkynyl, $C_{3-5}$ cycloalkyl, —O—$C_{3-5}$ cycloalkyl, and 5-membered heteroaryl are optionally substituted by 1, 2, or 3 $R_b$;

$R_3$ is selected from $C_{1-4}$ alkyl, piperazinyl, and 7- to 9-membered heterocycloalkyl, and the $C_{1-4}$ alkyl, piperazinyl, and 7- to 9-membered heterocycloalkyl are optionally substituted by 1, 2, or 3 $R_c$;

$R_4$ is selected from $C_{1-3}$ alkyl and $C_{1-3}$ alkoxy, and the $C_{1-3}$ alkyl and $C_{1-3}$ alkoxy are optionally substituted by 1, 2, or 3 $R_d$;

$R_5$ is selected from H and OH;

or, $R_1$ and $R_3$ together with the atom to which they are attached form a ring, so that the structural moiety

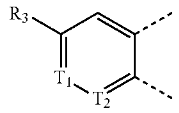

is selected from

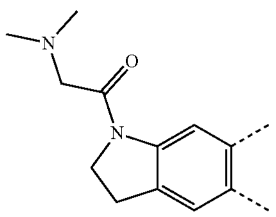

;

each $R_b$ is independently selected from F, Cl, Br, I, OH, and $OCH_3$;

each $R_c$ is independently selected from =O, $C_{1-3}$ alkyl, $C_{1-4}$ alkylamino, and heterocyclobutyl, and the $C_{1-3}$ alkyl, $C_{1-4}$ alkylamino, and heterocyclobutyl are optionally substituted by 1, 2, or 3 R;

each $R_d$ is independently selected from F, Cl, Br, and I;

each R is independently selected from F, Cl, Br, I, and OH;

heteroatoms of the "heterocyclobutyl" and "7- to 9-membered heterocycloalkyl" are selected from N, O, and S.

In some embodiments of the present disclosure, the $R_2$ is selected from H, CN, $SCH_3$, $SCH_2CH_3$, $SCH(CH_3)_2$, $S(=O)_2CH_3$, $OCH_3$, $OCH_2CH_3$, $OCH(CH_3)_2$, $CH_3$, $CH_2CH_3$, $CH(CH_3)_2$, cyclopropyl,

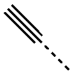, 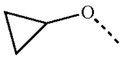, and 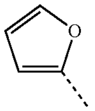, and the $SCH_3$, $SCH_2CH_3$, $SCH(CH_3)_2$, $S(=O)_2CH_3$, $OCH_3$, $OCH_2CH_3$, $OCH(CH_3)_2$, $CH_3$, $CH_2CH_3$, $CH(CH_3)_2$, cyclopropyl,

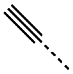, 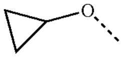, and 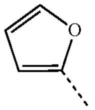, are optionally substituted by 1, 2, or 3 $R_b$, and other variables are as defined in the present disclosure.

In some embodiments of the present disclosure, the $R_2$ is selected from H, CN, $SCH_3$, $SCH_2CH_2OH$, $S(=O)_2CH_3$, $OCH_2CH_3$, $OCH_2CH_2OH$, $OCH_2CH_2OCH_3$, $CH_3$, $CH_2CH_2OH$, $CH_2OCH_3$, cyclopropyl,

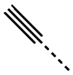, 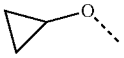, and 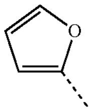, and other variables are as defined in the present disclosure.

In some embodiments of the present disclosure, the $R_c$ is selected from =O, $CH_3$, $CH_2CH_3$, $N(CH_3)_2$, and

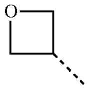, and the $CH_3$, $CH_2CH_3$, and $N(CH_3)_2$ are optionally substituted by 1, 2, or 3 R, and other variables are as defined in the present disclosure.

In some embodiments of the present disclosure, the $R_c$ is selected from =O, $CH_3$, $CH_2CH_2OH$, $N(CH_3)_2$, and

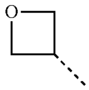

and other variables are as defined in the present disclosure.

In some embodiments of the present disclosure, the $R_3$ is selected from $CH_2CH_2CH_3$,

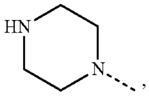, 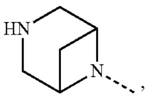, 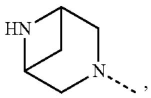, and 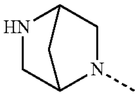, and the $CH_2CH_2CH_3$,

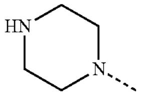 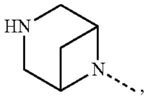, 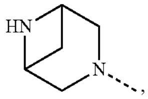, and 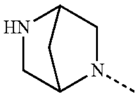

are optionally substituted by 1, 2, or 3 $R_c$, and other variables are as defined in the present disclosure.

In some embodiments of the present disclosure, the $R_3$ is selected from

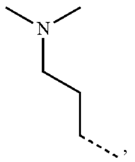, 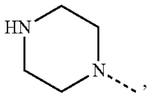, 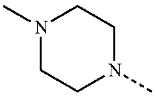, 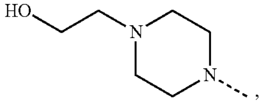, 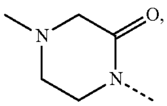 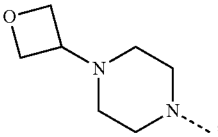, 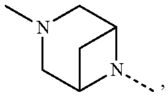, 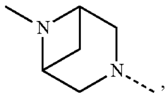, and 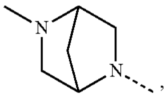, and other variables are as defined in the present disclosure.

The compound or a pharmaceutically acceptable salt thereof according to claim 1, wherein $R_4$ is selected from $CH_3$, $OCH_3$, $OCHF_2$, and $OCF_3$, and other variables are as defined in the present disclosure.

The present disclosure provides a compound of formula (II) or a pharmaceutically acceptable salt thereof (II)

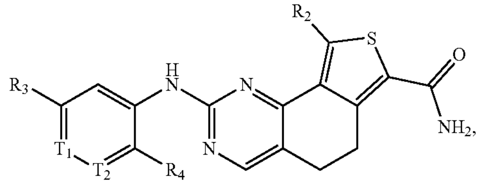

wherein $T_1$ is selected from $CR_1$ and N;

$T_2$ is selected from CH and N;

$R_1$ is selected from H;

$R_2$ is selected from H, CN, $C_{1-3}$ alkyl, $C_{1-3}$ alkoxy, $C_{1-3}$ alkylthiol, $S(=O)_2C_{1-3}$ alkyl, $C_{2-3}$ alkynyl, $C_{3-5}$ cycloalkyl, —O—$C_{3-5}$ cycloalkyl and 5-membered heteroaryl, and the $C_{1-3}$ alkyl, $C_{1-3}$ alkoxy, $C_{1-3}$ alkylthiol, $S(=O)_2C_{1-3}$ alkyl, $C_{2-3}$ alkynyl, $C_{3-5}$ cycloalkyl, —O—$C_{3-5}$ cycloalkyl and 5-membered heteroaryl are optionally substituted by 1, 2, or 3 $R_b$;

$R_3$ is selected from $C_{1-4}$ alkyl, piperazinyl, and 7- to 9-membered heterocycloalkyl, and the $C_{1-4}$ alkyl, piperazinyl, and 7- to 9-membered heterocycloalkyl are optionally substituted by 1, 2, or 3 $R_c$;

$R_4$ is selected from $C_{1-3}$ alkyl and $C_{1-3}$ alkoxy, and the $C_{1-3}$ alkyl and $C_{1-3}$ alkoxy are optionally substituted by 1, 2, or 3 $R_d$;

or, $R_1$ and $R_3$ together with the atom to which they are attached form a ring, so that the structural moiety

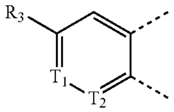

is selected from

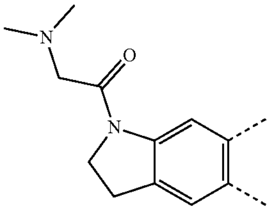

each $R_b$ is independently selected from F, Cl, Br, I, OH, and $OCH_3$;

each $R_c$ is independently selected from =O, $C_{1-3}$ alkyl, $C_{1-4}$ alkylamino, and heterocyclobutyl, and the $C_{1-3}$ alkyl, $C_{1-4}$ alkylamino, and heterocyclobutyl are optionally substituted by 1, 2, or 3 R;

each $R_d$ is independently selected from F, Cl, Br, and I;

each R is independently selected from F, Cl, Br, I, and OH;

heteroatoms of the "heterocyclobutyl" and "7- to 9-membered heterocycloalkyl" are selected from N, O, and S.

In some embodiments of the present disclosure, the $R_2$ is selected from H, CN, $SCH_3$, $SCH_2CH_3$, $SCH(CH_3)_2$, $S(=O)_2CH_3$, $OCH_3$, $OCH_2CH_3$, $OCH(CH_3)_2$, $CH_3$, $CH_2CH_3$, $CH(CH_3)_2$, cyclopropyl,

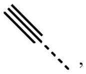 , 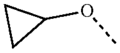 , and 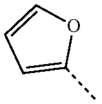 , and the $SCH_3$, $SCH_2CH_3$, $SCH(CH_3)_2$, $S(=O)_2CH_3$, $OCH_3$, $OCH_2CH_3$, $OCH(CH_3)_2$, $CH_3$, $CH_2CH_3$, $CH(CH_3)_2$, cyclopropyl,

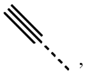 , 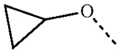 , and 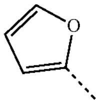 , are optionally substituted by 1, 2, or 3 $R_b$, and other variables are as defined in the present disclosure.

In some embodiments of the present disclosure, the $R_2$ is selected from H, CN, $SCH_3$, $SCH_2CH_2OH$, $S(=O)_2CH_3$, $OCH_2CH_3$, $OCH_2CH_2OH$, $OCH_2CH_2OCH_3$, $CH_3$, $CH_2CH_2OH$, $CH_2OCH_3$, cyclopropyl,

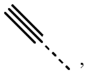 , 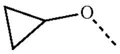 , and 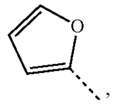 , and other variables are as defined in the present disclosure.

In some embodiments of the present disclosure, the $R_c$ is selected from $CH_3$, $CH_2CH_3$, $N(CH_3)_2$, and

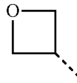 , and the $CH_3$, $CH_2CH_3$, and $N(CH_3)_2$ are optionally substituted by 1, 2, or 3 R, and other variables are as defined in the present disclosure.

In some embodiments of the present disclosure, the $R_c$ is selected from $CH_3$, $CH_2CH_2OH$, $N(CH_3)_2$, and

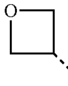 , and other variables are as defined in the present disclosure.

In some embodiments of the present disclosure, the $R_3$ is selected from $CH_2CH_2CH_3$,

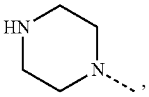 , 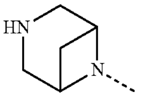 , 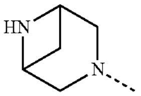 , and 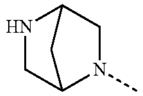 , and the $CH_2CH_2CH_3$,

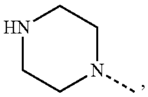 , 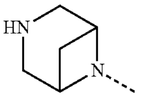 , 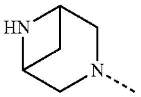 , and 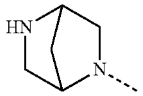 , are optionally substituted by 1, 2, or 3 $R_c$, and other variables are as defined in the present disclosure.

In some embodiments of the present disclosure, the $R_3$ is selected from

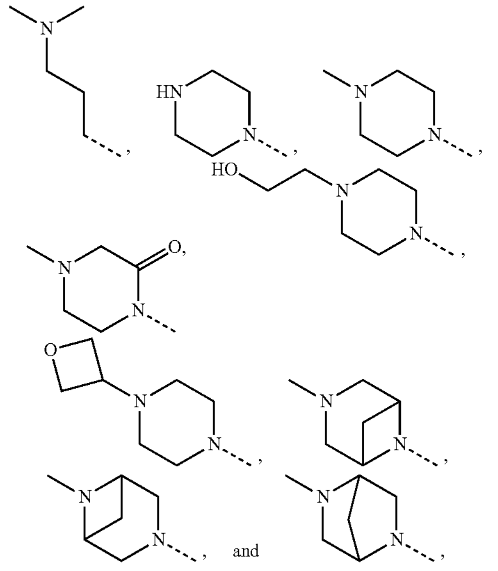

and and other variables are as defined in the present disclosure.

In some embodiments of the present disclosure, the $R_4$ is selected from $CH_3$, $OCH_3$, $OCHF_2$, and $OCF_3$, and other variables are as defined in the present disclosure.

The present disclosure provides a compound of formula (II) or a pharmaceutically acceptable salt thereof (II)

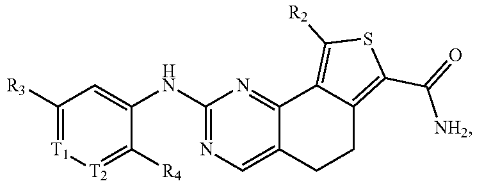

wherein $T_1$ is selected from $CR_1$ and N;

$T_2$ is selected from CH and N;

$R_1$ is selected from H;

$R_2$, is selected from H, CN, $C_{1-3}$ alkyl, $C_{1-3}$ alkoxy, $C_{1-3}$ alkylthiol, and $C_{3-5}$ cycloalkyl, and the $C_{1-3}$ alkyl, $C_{1-3}$ alkoxy, $C_{1-3}$ alkylthiol, and $C_{3-5}$ cycloalkyl are optionally substituted by 1, 2, or 3 $R_b$;

$R_3$ is selected from $C_{1-4}$ alkyl, piperazinyl, and 7- to 9-membered heterocycloalkyl, and the $C_{1-4}$ alkyl, piperazinyl, and 7- to 9-membered heterocycloalkyl are optionally substituted by 1, 2, or 3 $R_c$;

$R_4$ is selected from $C_{1-3}$ alkyl and $C_{1-3}$ alkoxy, and the $C_{1-3}$ alkyl and $C_{1-3}$ alkoxy are optionally substituted by 1, 2, or 3 $R_d$;

or, $R_1$ and $R_3$ together with the atom to which they are attached form a ring, so that the structural moiety

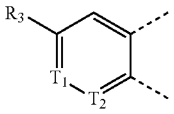

is selected from

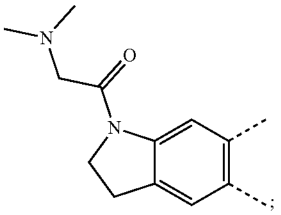

each $R_a$ is independently selected from F, Cl, Br, I, $CH_3$, and $CF_3$;

each $R_b$ is independently selected from F, Cl, Br, I, OH, and $OCH_3$;

each $R_c$ is independently selected from =O, $C_{1-3}$ alkyl, $C_{1-4}$ alkylamino, and heterocyclobutyl, and the $C_{1-3}$ alkyl, $C_{1-4}$ alkylamino, and heterocyclobutyl are optionally substituted by 1, 2, or 3 R;

each $R_d$ is independently selected from F, Cl, Br, and I;

each R is independently selected from F, Cl, Br, I, and OH;

heteroatoms of the "heterocyclobutyl" and "7- to 9-membered heterocycloalkyl" are selected from N, O, and S.

In some embodiments of the present disclosure, the $R_2$ is selected from H, CN, $SCH_3$, $SCH_2CH_3$, $SCH(CH_3)_2$, $OCH_3$, $OCH_2CH_3$, $OCH(CH_3)_2$, $CH_3$, $CH_2CH_3$, $CH(CH_3)_2$, and cyclopropyl, and the $SCH_3$, $SCH_2CH_3$, $SCH(CH_3)_2$, $OCH_3$, $OCH_2CH_3$, $OCH(CH_3)_2$, $CH_3$, $CH_2CH_3$, $CH(CH_3)_2$, and cyclopropyl are optionally substituted by 1, 2, or 3 $R_b$, and other variables are as defined in the present disclosure.

In some embodiments of the present disclosure, the $R_2$ is selected from H, CN, $SCH_3$, $SCH_2CH_2OH$, $OCH_2CH_3$, $OCH_2CH_2OH$, $CH_3$, $CH_2CH_2OH$, $CH_2OCH_3$, and cyclopropyl, and other variables are as defined in the present disclosure.

In some embodiments of the present disclosure, the $R_c$ is selected from $CH_3$, $CH_2CH_3$, $N(CH_3)_2$, and

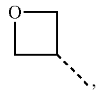

and the $CH_3$, $CH_2CH_3$, and $N(CH_3)_2$ are optionally substituted by 1, 2, or 3 R, and other variables are as defined in the present disclosure.

In some embodiments of the present disclosure, the $R_c$ is selected from $CH_3$, $CH_2CH_2OH$, $N(CH_3)_2$, and

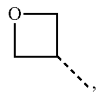

and other variables are as defined in the present disclosure.

In some embodiments of the present disclosure, the $R_3$ is selected from $CH_2CH_2CH_3$,

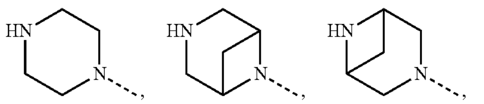

and

-continued

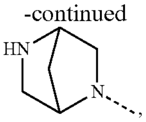

and the $CH_2CH_2CH_3$,

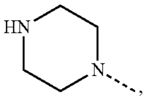 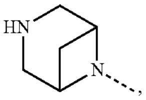 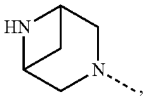 and 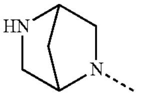

are optionally substituted by 1, 2, or 3 $R_c$, and other variables are as defined in the present disclosure.

In some embodiments of the present disclosure, the $R_3$ is selected from

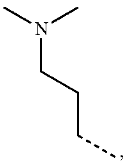 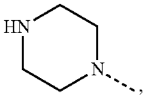 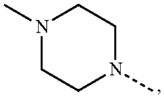

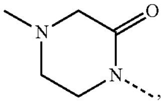 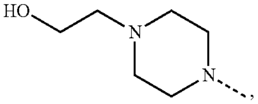

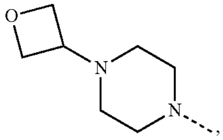 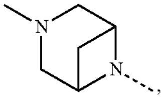

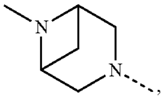 and 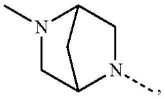

and other variables are as defined in the present disclosure.

In some embodiments of the present disclosure, the $R_4$ is selected from $CH_3$, $OCH_3$, $OCHF_2$, and $OCF_3$, and other variables are as defined in the present disclosure.

The present disclosure provides a compound of formula (II) or a pharmaceutically acceptable salt thereof (II)

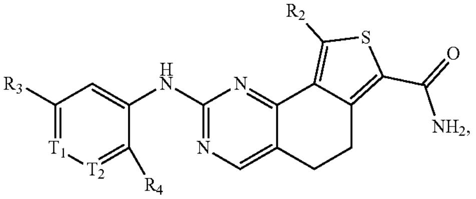

wherein $T_1$ is selected from $CR_1$ and N;

T2 is selected from CH and N;

$R_1$ is selected from H;

$R_2$ is selected from $C_{1-3}$ alkyl, $C_{1-3}$ alkoxy, and $C_{1-3}$ alkylthiol, and the $C_{1-3}$ alkyl, $C_{1-3}$ alkoxy, and $C_{1-3}$ alkylthiol are optionally substituted by 1, 2, or 3 $R_b$;

$R_3$ is selected from $C_{1-4}$ alkyl and piperazinyl, and the $C_{1-4}$ alkyl and piperazinyl are optionally substituted by 1, 2, or 3 $R_c$;

$R_4$ is selected from $C_{1-3}$ alkyl and $C_{1-3}$ alkoxy, and the $C_{1-3}$ alkyl and $C_{1-3}$ alkoxy are optionally substituted by 1, 2, or 3 $R_d$;

or, $R_1$ and $R_3$ together with the atom to which they are attached form pyrrolidinyl, and the pyrrolidinyl is optionally substituted by

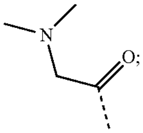

each $R_a$ is independently selected from F, Cl, Br, I, $CH_3$, and $CF_3$;

each $R_b$ is independently selected from F, Cl, Br, I, and OH;

each $R_c$ is independently selected from $C_{1-3}$ alkyl, $C_{1-4}$ alkylamino, and heterocyclobutyl, and the $C_{1-3}$ alkyl, $C_{1-4}$ alkylamino, and heterocyclobutyl are optionally substituted by 1, 2, or 3 R;

each $R_d$ is independently selected from F, Cl, Br, and I;

each R is independently selected from F, Cl, Br, I, and OH;

heteroatoms of the heterocyclobutyl are selected from N, O, and S.

In some embodiments of the present disclosure, the $R_2$ is selected from $SCH_3$, $SCH_2CH_3$, $SCH(CH_3)_2$, $OCH_3$, $OCH_2CH_3$, $OCH(CH_3)_2$, $CH_3$, $CH_2CH_3$, and $CH(CH_3)_2$, and the $SCH_3$, $SCH_2CH_3$, $SCH(CH_3)_2$, $OCH_3$, $OCH_2CH_3$, $OCH(CH_3)_2$, $CH_3$, $CH_2CH_3$, and $CH(CH_3)_2$ are optionally substituted by 1, 2, or 3 $R_b$, and other variables are as defined in the present disclosure.

In some embodiments of the present disclosure, the $R_2$ is selected from $SCH_3$, $SCH_2CH_2OH$, $OCH_2CH_3$, and $CH_2CH_2OH$, and other variables are as defined in the present disclosure.

In some embodiments of the present disclosure, the $R_c$ is selected from $CH_3$, $CH_2CH_3$, $N(CH_3)_2$, and

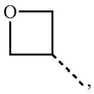

and the $CH_3$, $CH_2CH_3$, and $N(CH_3)_2$ are optionally substituted by 1, 2, or 3 R, and other variables are as defined in the present disclosure.

In some embodiments of the present disclosure, the $R_c$ is selected from $CH_3$, $CH_2CH_2OH$, $N(CH_3)_2$, and

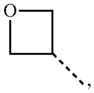

and other variables are as defined in the present disclosure.

In some embodiments of the present disclosure, the $R_3$ is selected from $CH_2CH_2CH_3$ and

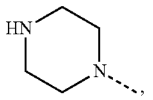

and the

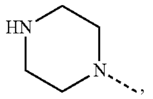

is optionally substituted by 1, 2, or 3 $R_c$, and other variables are as defined in the present disclosure.

In some embodiments of the present disclosure, the $R_3$ is selected from

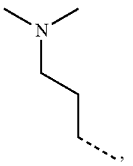

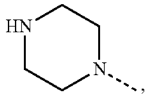

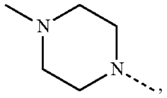

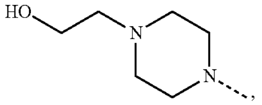

and

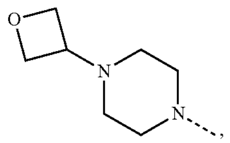

and other variables are as defined in the present disclosure.

In some embodiments of the present disclosure, the $R_4$ is selected from $CH_3$, $OCH_3$, and $OCF_3$, and other variables are as defined in the present disclosure.

In some embodiments of the present disclosure, the $R_1$ and $R_3$ together with the atom to which they are attached form pyrrolidinyl, so that the structural moiety

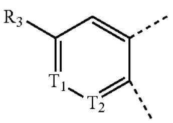

is selected from

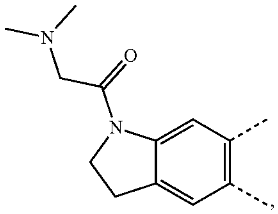

and other variables are as defined in the present disclosure.

In some embodiments of the present disclosure, the compound or the pharmaceutically acceptable salt thereof, the compound is selected from (P-1)

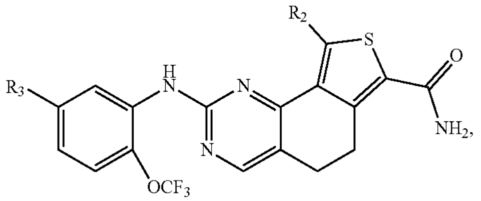

wherein $R_2$ and $R_3$ are as defined in the present disclosure.

In some embodiments of the present disclosure, the compound or the pharmaceutically acceptable salt thereof, the compound is selected from (P-2)

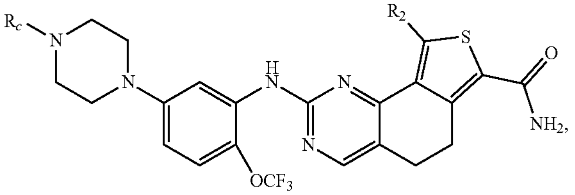

wherein $R_2$, and $R_c$ are as defined in the present disclosure.

In some embodiments of the present disclosure, the $R_2$ is selected from $C_{1-3}$ alkoxy, $C_{1-3}$ alkylthiol, and —O—$C_{3-5}$ cycloalkyl, and the $C_{1-3}$ alkoxy, $C_{1-3}$ alkylthiol, and —O—$C_{3-5}$ cycloalkyl are optionally substituted by 1, 2, or 3 $R_b$, and other variables are as defined in the present disclosure.

In some embodiments of the present disclosure, the $R_2$ is selected from $SCH_3$, $SCH_2CH_3$, $SCH(CH_3)_2$, $OCH_3$, $OCH_2CH_3$, $OCH(CH_3)_2$, and

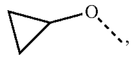

and the $SCH_3$, $SCH_2CH_3$, $SCH(CH_3)_2$, $OCH_3$, $OCH_2CH_3$, $OCH(CH_3)_2$, and

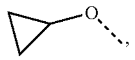

are optionally substituted by 1, 2, or 3 $R_b$, and other variables are as defined in the present disclosure.

In some embodiments of the present disclosure, the $R_2$ is selected from $SCH_3$, $SCH_2CH_2OH$, $OCH_2CH_3$, $OCH_2CH_2OH$, $OCH_2CH_2OCH_3$, and

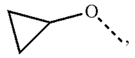

and other variables are as defined in the present disclosure.

In some embodiments of the present disclosure, the $R_c$ is selected from $CH_3$ and $CH_2CH_2OH$.

The present disclosure also provides a compound of formula (P-3) or a pharmaceutically acceptable salt thereof (P-3)

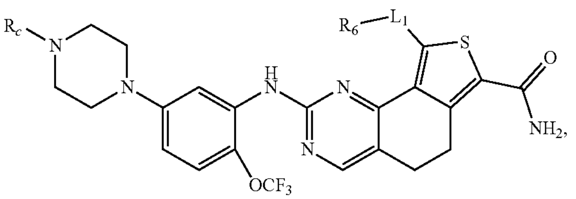

wherein $R_c$ is as defined in the present disclosure;

$L_1$ is selected from O and S;

$R_6$ is selected from $C_{1-3}$ alkyl and $C_{3-5}$ cycloalkyl.

In some embodiments of the present disclosure, the $R_6$ is selected from $CH_3$, $CH_2CH_3$, $CH_2CH_2CH_3$, $CH(CH_3)_2$, cyclopropyl, and cyclobutyl.

There are also some embodiments of the present disclosure that come from any combination of the above-mentioned variables.

The present disclosure also provides a compound shown below or a pharmaceutically acceptable salt thereof, and the compound is selected from

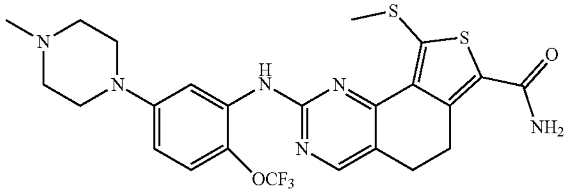

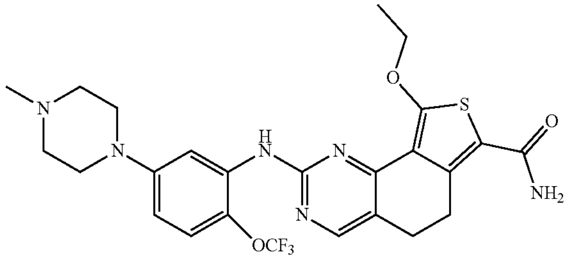

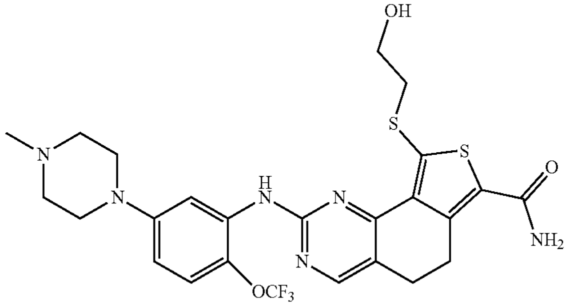

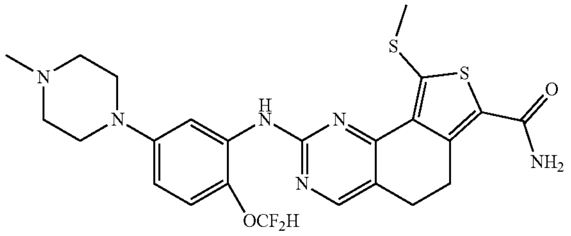

-continued

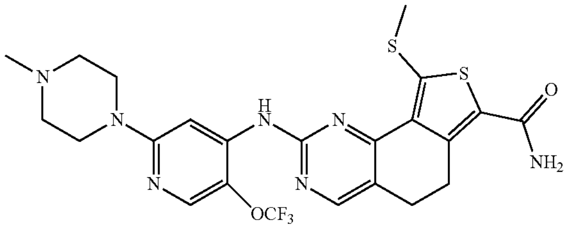

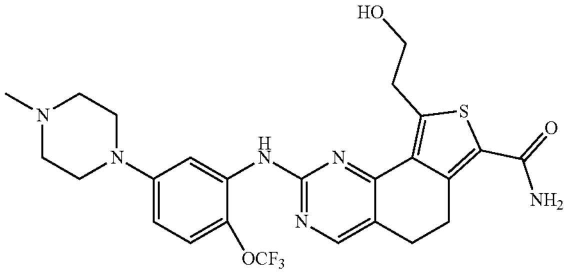

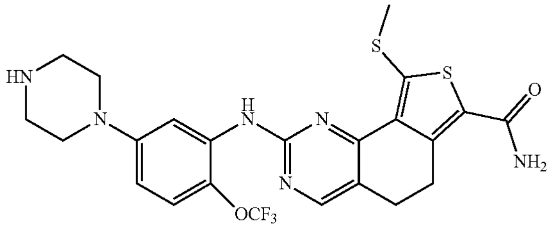

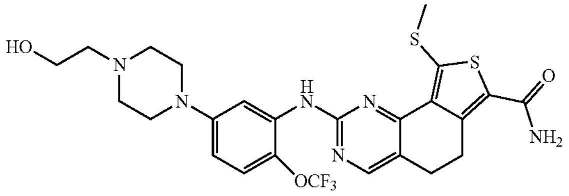

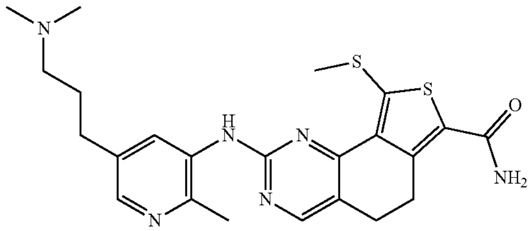

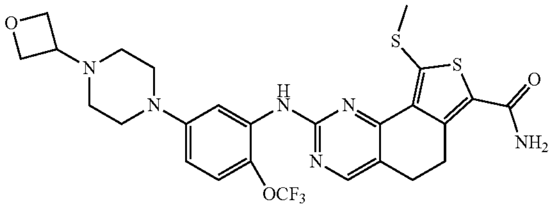

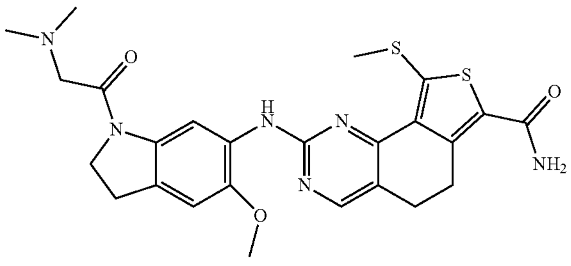

-continued
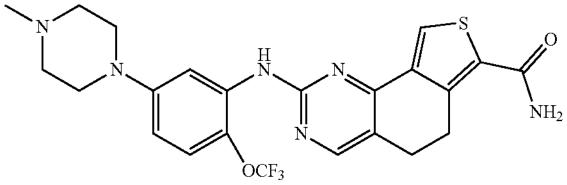
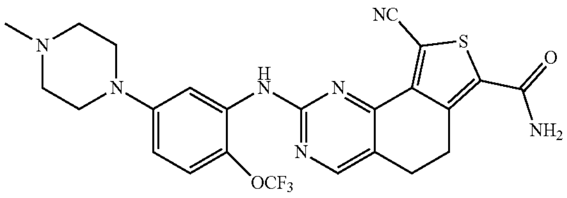
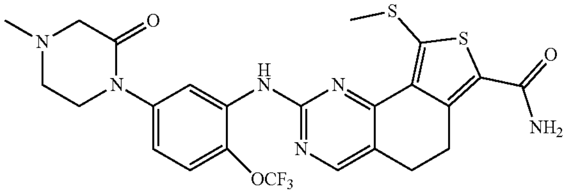
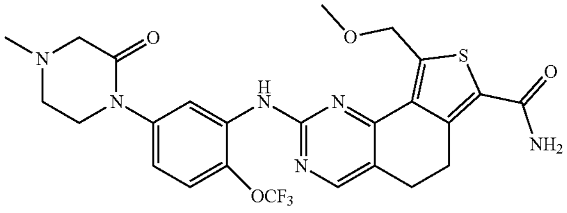
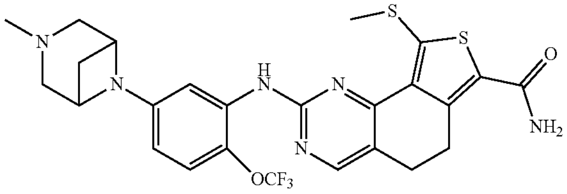
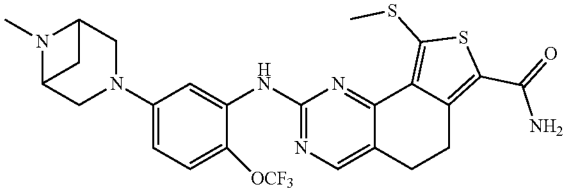
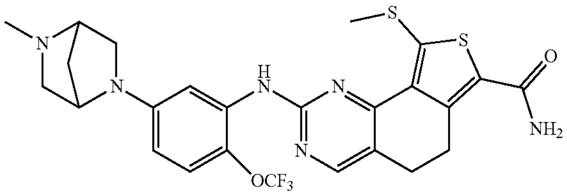
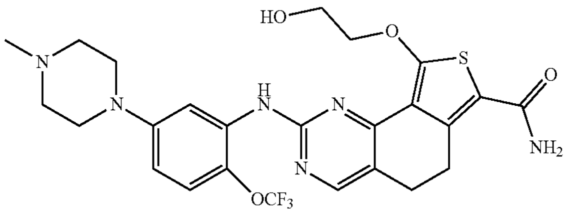
-continued
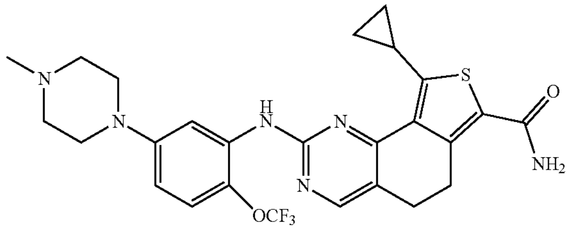
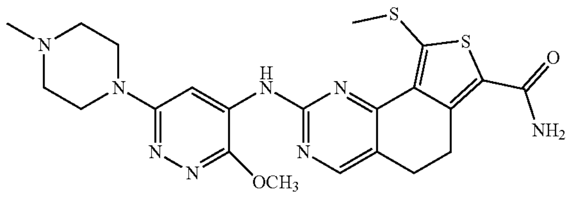
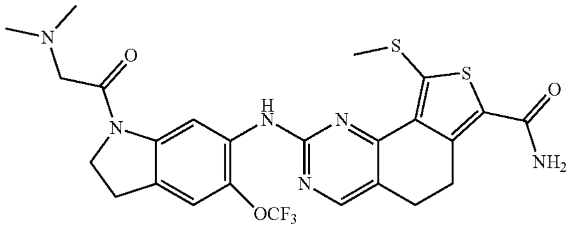
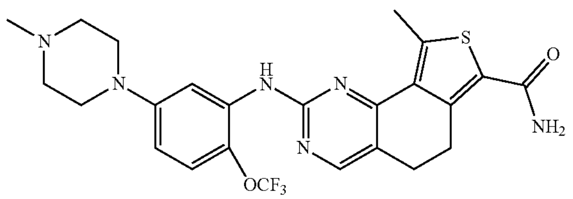
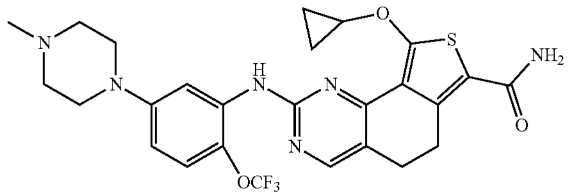
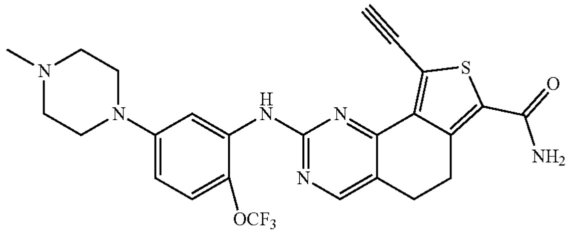
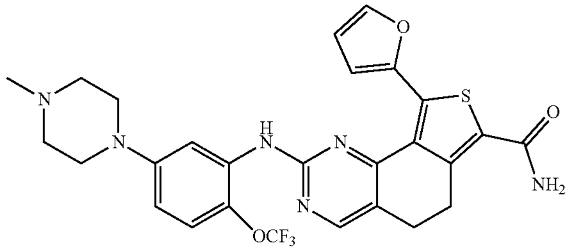

-continued

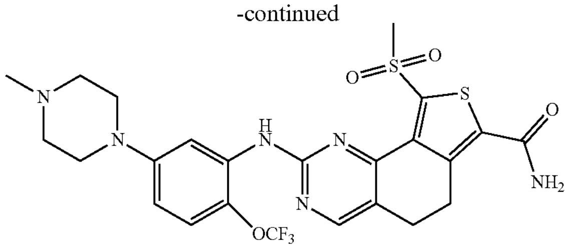

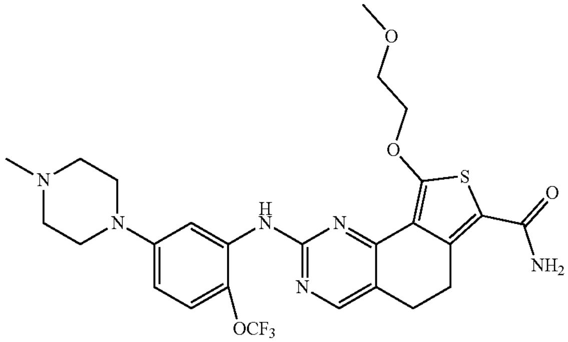

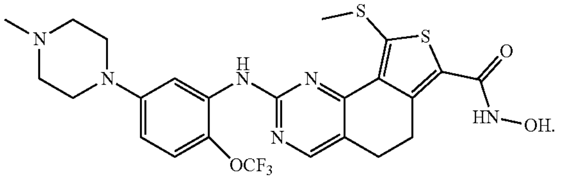

The present disclosure also provides a use of the compound or the pharmaceutically acceptable salt thereof in the manufacture of a medicament for treating solid tumors The present disclosure also provides a use of the compound or a pharmaceutically acceptable salt thereof in the manufacture of a medicament for treating solid tumors associated with a selective PLK1 inhibitor.

In some embodiments of the present disclosure, the solid tumor is colorectal cancer.

Related Definitions

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)-and (+)-enantiomers, (R)-and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by the sub stituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted by a ketone. The term "optionally substituted" means an atom can be substituted by a substituent or not, unless otherwise specified, the type and number of the sub stituent may be arbitrary as long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the sub stituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. When the group is a fused ring, spiro ring, or bridged ring structure, and when the fused ring, spiro ring, or bridged ring structure is linked to other groups through non-localized chemical bonds, any one or more sites of the fused ring, spiro ring or bridged ring can be linked to other groups by chemical bonds. The chemical bond between the site and other groups can be represented by a straight solid (), a straight dashed bond () or a wavy line (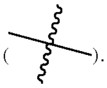).

For example, the straight solid line bond in —$OCH_3$ represents that the oxygen atom in the group is linked to other groups; the straight dotted line bond in

represents that the two ends of the nitrogen atom in the group are linked to other groups; the wavy line in

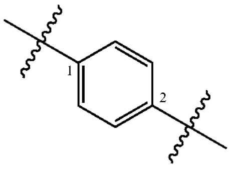 [SMILES: *c1ccc(*)cc1]

represents that it is linked to other groups through the 1 and 2 carbon atoms in the phenyl group;

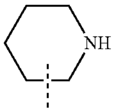

represents that any linkable site on the piperidinyl group can be connected to other groups through a chemical bond, including at least 4 linking methods such as

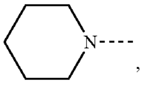, 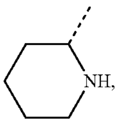 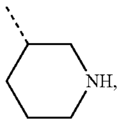

-continued

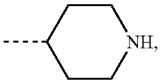

even if the H atom is drawn on —N—, but

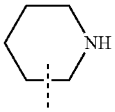

but still includes the group linked in way of

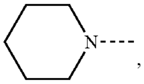, provided that when only a chemical bond is linked the H at this site will be reduced by one correspondingly to become monovalent piperidinyl group;

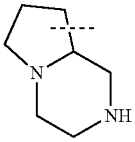

represents that any linkable site on the group can be linked to other groups through a chemical bond, including at least 8 linking methods such as

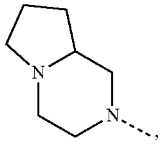 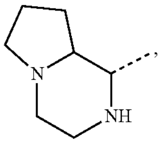

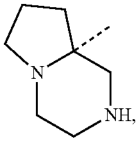 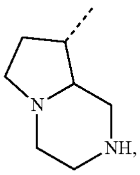

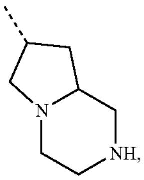 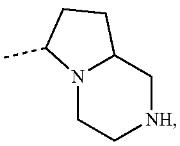

-continued

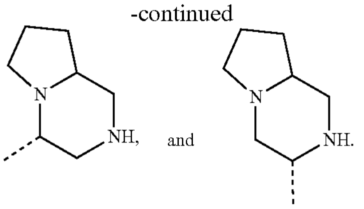

Unless otherwise specified, $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$,$C_{6-12}$,and $C_{9-12}$, etc.; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, etc.

Unless otherwise specified, the term "7- to 9-membered heterocycloalkyl" by itself or in combination with other terms refers to a saturated cyclic group consisting of 7 to 9 ring atoms, respectively, whose 1, 2, 3, or 4 ring atoms are heteroatoms independently selected from O, S, and N, and the rest are carbon atoms, wherein the nitrogen atom is optionally quaternized, and the nitrogen and sulfur heteroatoms can be optionally oxidized (i.e., NO and $S(O)_p$, p is 1 or 2). It includes monocyclic and bicyclic ring systems, wherein bicyclic ring systems include spiro, fused and bridged rings. In addition, with respect to the "7- to 9-membered heterocycloalkyl", a heteroatom may occupy the position where the heterocycloalkyl is linked to the rest of the molecule. The 7- to 9-membered heterocycloalkyl includes 7-membered, 8-membered, and 9-membered heterocycloalkyl. Examples of 7- to 9-membered heterocycloalkyl include, but are not limited to,

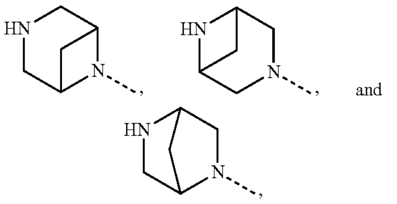

etc.

Unless otherwise specified, "$C_{3-5}$ cycloalkyl" refers to a saturated cyclic hydrocarbon group composed of 3 to 5 carbon atoms, which is a monocyclic ring system, and the $C_{3-5}$ cycloalkyl includes $C_{3-4}$ and $C_{4-5}$ cycloalkyl, etc.; it can be monovalent, divalent or multivalent. Examples of $C_{3-5}$ cycloalkyl include, but are not limited to, cyclopropyl, cyclobutyl, cyclopentyl, etc.

Unless otherwise specified, the terms "5-membered heteroaryl ring" and "5-membered heteroaryl" can be used interchangeably in the present disclosure, and the term "5-membered heteroaryl" refers to a monocyclic group consisting of 5 to 6 ring atoms, which has a conjugated 7c-electron system, wherein 1, 2, 3, or 4 ring atoms are heteroatoms independently selected from O, S, and N, and the rest are carbon atoms. Herein, the nitrogen atom is optionally quaternized, the nitrogen and sulfur heteroatoms can optionally be oxidized (i.e., NO and S(O)p, p is 1 or 2). The 5-membered heteroaryl can be linked to the rest of the molecule through a heteroatom or a carbon atom. Examples of the 5-membered heteroaryl group include, but are not limited to, pyrrolyl (including N-pyrrolyl, 2-pyrrolyl, and 3-pyrrolyl, etc.), pyrazolyl (including 2-pyrazolyl and 3-pyrazolyl, etc.), imidazolyl (including N-imidazolyl, 2-imidazolyl, 4-imidazolyl, and 5-imidazolyl, etc.), oxazolyl (including 2-oxazolyl, 4-oxazolyl, and 5-oxazolyl, etc.), triazolyl (1H-1,2,3-triazolyl, 2H-1,2,3-triazolyl, 1H-1,2,4-triazolyl, and 4H-1,2,4 -triazolyl, etc.), tetrazolyl, isoxazolyl (3-isoxazolyl, 4-isoxazolyl, and 5-isoxazolyl, etc.), thiazolyl (including 2-thiazolyl, 4-thiazolyl, and 5-thiazolyl, etc.), furyl (including 2-furyl and 3-furyl, etc.), thienyl (including 2-thienyl and 3-thienyl, etc.).

Unless otherwise specified, the term "$C_{1-4}$ alkylamino" refers to those alkyl groups containing 1 to 4 carbon atoms linked to the rest of the molecule through an amino group. The $C_{1-4}$ alkylamino includes $C_{1-3}$, $C_{1-2}$, $C_{2-4}$, $C_4$, $C_3$, and $C_2$ alkylamino, etc. Examples of $C_{1-4}$ alkylamino include, but are not limited to, $—NHCH_3$, $—N(CH_3)_2$, $—NHCH_2CH_3$, $—N(CH_3)CH_2CH_3$, $—N(CH_2CH_3)(CH_2CH_3)$, $—NHCH_2CH_2CH_3$, $—NHCH_2(CH_3)_2$, $—NHCH_2CH_2CH_2CH_3$, etc.

Unless otherwise specified, the term "$C_{1-3}$ alkoxy" refers to an alkyl group containing 1 to 3 carbon atoms that are linked to the rest of the molecule through an oxygen atom. The $C_{1-3}$ alkoxy includes $C_{1-2}$, $C_{2-3}$, $C_3$, and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-3}$ alkylthiol" refers to those alkyl groups containing 1 to 3 carbon atoms linked to the rest of the molecule through a sulfur atom. The $C_{1-3}$ alkylthiol includes $C_{1-3}$, $C_{1-2}$, and $C_3$ alkylthiol, etc. Examples of $C_{1-3}$ alkylthiol include, but are not limited to, $—SCH_3$, $—SCH_2CH_3$, $—SCH_2CH_2CH_3$, $—SCH_2(CH_3)_2$, etc.

Unless otherwise specified, the term "$C_{1-4}$ alkyl" refers to a linear or branched saturated hydrocarbon group containing 1 to 4 carbon atoms. The $C_{1-4}$ alkyl includes $C_{1-2}$, $C_{1-3}$ and $C_{2-3}$ alkyl groups and the like. It can be monovalent (such as methyl), divalent (such as methylene) or multivalent (such as methine). Examples of $C_{1-4}$ alkyl include, but are not limited to, methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include, but are not limited to methyl (Me), ethyl (Et), propyl (including n-propyl and isopropyl), etc.

Unless otherwise specified, "$C_{2-3}$ alkynyl" is used to denote a straight or branched chain hydrocarbon group consisting of 2 to 3 carbon atoms containing at least one carbon-carbon triple bond, which may at any position in the group. It may be monovalent, divalent or polyvalent. The $C_{2-3}$ alkynyl includes $C_3$ and $C_2$ alkynyl. Examples of $C_{2-3}$ alkynyl include, but are not limited to, ethynyl, propynyl, etc.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the present disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvents used in the present disclosure are commercially available.

TECHNICAL EFFECT

Figure 1:
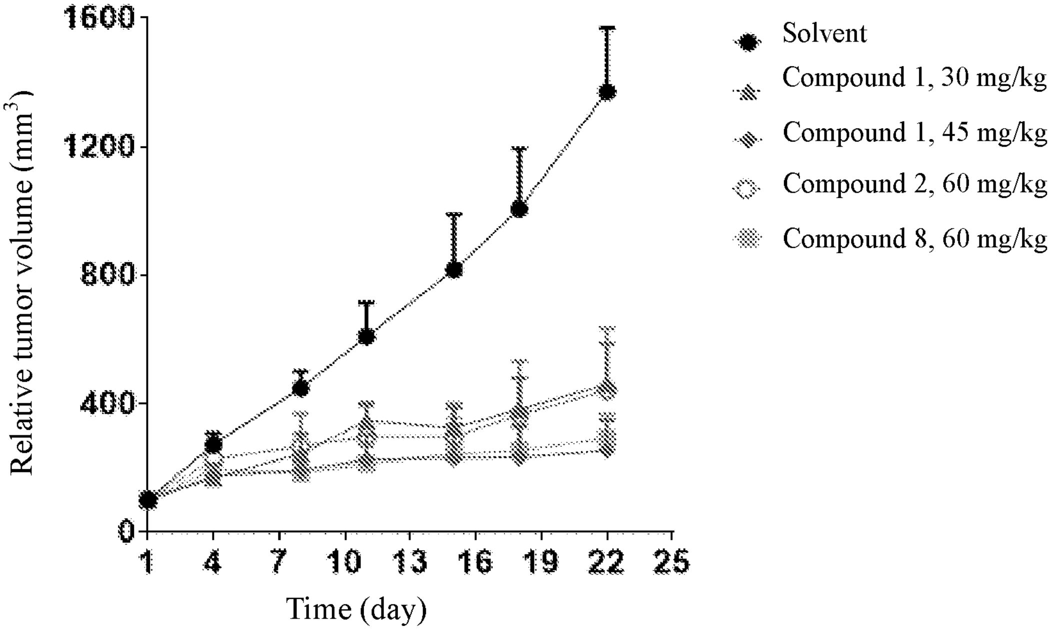
FIG. 1. Tumor volume diagram of in vivo pharmacodynamic study of human colon cancer HCT-116 cell subcutaneous xenograft tumor model.

The compound of the present disclosure has a better inhibitory effect on PLK1, and can selectively inhibit PLK1, and exhibits better inhibitory activity against cell proliferation and a significant anti-tumor effect in in vivo pharmacodynamic studies, and a good animal tolerance. The compound of the present disclosure has good pharmacokinetic properties.

DETAILED DESCRIPTION OF THE PREFERRED EMBODIMENT

The present disclosure will be specifically described below by way of examples, but the scope of the present disclosure is not limited thereto. The present disclosure has been described in detail herein, wherein specific embodiments thereof are also disclosed. For those skilled in the art, it is obvious that various changes and improvements can be made to the specific embodiments of the present disclosure without departing from the spirit and scope of the present disclosure.

Example 1

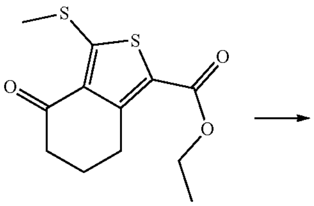

1-1

-continued

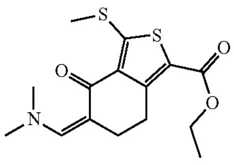

1-2

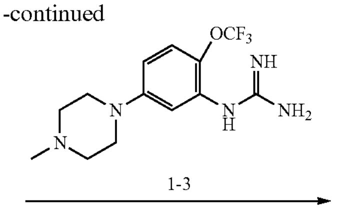

1-3

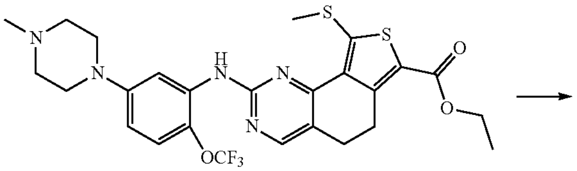

1-4

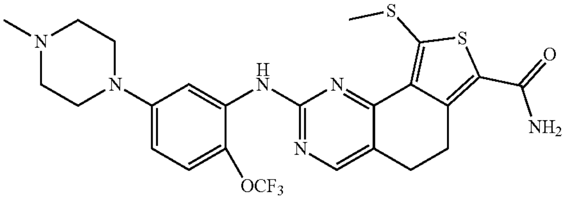

1

Step 1: Synthesis of Compound 1-2

Compound 1-1 (500 mg, 1.85 mmol, 1 eq) was dissolved in tetrahydrofuran (5 mL), and tert-butoxy bis(dimethylamino)methane (966.93 mg, 5.55 mol, 3 eq) was added thereto at 20° C. After the addition, the temperature was raised to 90° C. and the reaction was carried out for 12 hours. When the disappearance of the raw materials was detected by LCMS, the temperature was lowered to 20° C., and the solvent was removed by concentration under reduced pressure with an oil pump to obtain compound 1-2, and the crude product was directly used in the next reaction.

Characterization of Compound 1-2

$^1$H NMR (400 MHz, $CDCl_3$) δ: 1.30 (t, J=7.04 Hz, 3 H), 2.51 (s, 3 H), 2.78-2.82 (m, 2 H), 3.05 (s, 6 H), 3.07-3.11 (m, 2 H), 4.25 (q, J=7.04 Hz, 2 H), 7.52 (s, 1 H).

Step 2: Synthesis of Compound 1-4

Compound 1-2 (180 mg, 553.09 μmol, 1 eq) and compound 1-3 (193.05 mg, 608.40 μmol, 1.1 eq) were dissolved in N,N-dimethylformamide (4 mL) sequentially, the temperature was raised to 110° C. and the reaction was carried out for 20 hours. When the disappearance of the raw material compound 1-2 was detected by LCMS, water (20 mL) was added to dilute the system, and the mixture was extracted with ethyl acetate (20 mL*3). The phases were separated, and the organic phase was combined, washed with saturated brine (50 mL) and dried over anhydrous sodium sulfate. The filtrate was filtered, concentrated under reduced pressure to obtain the crude product, which was separated by thin-layer chromatography (developing agent: dichloromethane: methanol=20:1) to obtain compound 1-4.

Characterization of Compound 1-4

LCMS: m/z (ESI)=580.17 $[M+H]^+$.

$^1H$ NMR (400 MHz, $CDCl_3$) δ: 1.46-1.50 (m, 3 H), 2.30 (s, 3 H), 2.53 (s, 4 H), 2.58-2.62 (m, 3 H), 2.66-2.70 (m, 2 H), 3.09-3.32 (m, 6 H), 4.25-4.29 (m, 2 H), 6.35-6.45 (m, 1 H), 7.03-7.07 (m, 1 H), 7.24 (s, 1 H), 8.21 (s, 1 H), 8.32-8.36 (m, 1 H).

Step 3: Synthesis of Compound 1

Compound 1-4 (90 mg, 155.26 μmol, 1 eq) was dissolved in tetrahydrofuran (1 mL), cooled to 0° C., and ammonium chloride (49.83 mg, 931.59 μmol, 6.0 eq) and a solution of lithium bis(trimethylsilyl)amide in tetrahydrofuran at a concentration of 1 M (1.55 mL, 10 eq) were added thereto. After the addition was completed, the temperature was raised to 25° C., and the reaction was carried out at this temperature for 2 hours. Ethanol (2 mL) was added to quench the reaction, and the reaction mixture was concentrated under reduced pressure to remove the solvent to obtain the crude product, which is purified by HPLC preparative chromatography (HPLC preparation method: Phenomenex preparative chromatograph; chromatographic column: C18 80*40 mm*3 μm; mobile phase A: aqueous solution containing 0.05% ammonia water, mobile phase B: acetonitrile; running gradient: B %: 38% to 68%, run for 8 min) to obtain compound 1.

Characterization of Compound 1

LCMS: m/z (ESI)=551.15 $[M+H]^+$.

$^1H$ NMR (400 MHz, $CDCl_3$) δ: 2.22 (s, 3 H), 2.43-2.46 (m, 4 H), 2.54 (s, 3 H), 2.72 -2.76 (m, 2 H), 3.08-3.18 (m, 6 H), 6.68-6.73 (m, 1 H), 7.15-7.21 (m, 1 H), 7.44 (s, 2 H), 7.48-7.54 (m, 1 H), 8.33 (s, 1 H), 8.48 (s, 1 H).

Example 2

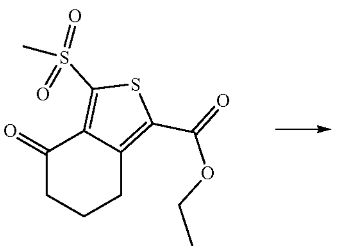

2-1

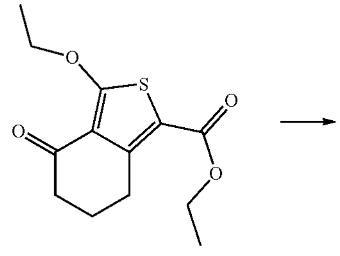

2-2

-continued

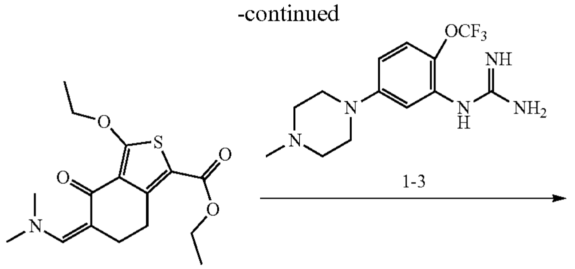

1-3

2-3

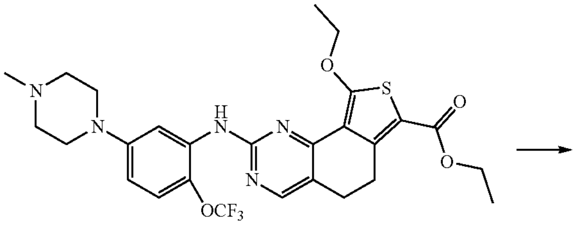

2-4

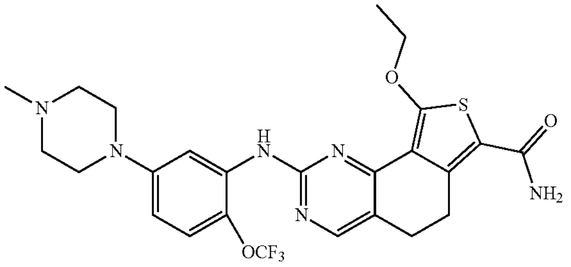

2

Step 1: Synthesis of Compound 2-2

Sodium tert-butoxide (127.13 mg, 1.32 mmol, 2 eq) was dissolved in tetrahydrofuran (1.6 mL), and ethanol (154 μL, 1.32 mmol, 1.9 eq) was added thereto at 20° C. The mixture was stirred for 30 minutes, then the system was cooled down to 0° C., and compound 2-1 (200 mg, 661.45 μmol, 1 eq) was added thereto. After the addition was completed, the reaction was continued for 1 hour, and water (20 mL) was added to quench the reaction after the reaction was completed. The reaction mixture was extracted with ethyl acetate (30 mL*3), and the organic phase was combined, then washed with saturated brine (50 mL), dried over anhydrous sodium sulfate, filtered, and the filtrate was concentrated under reduced pressure to obtain the crude product. The crude product was purified by silica gel column chromatography (eluent: petroleum ether:ethyl acetate=4:1) to obtain compound 2-2.

Characterization of Compound 2-2

$^1H$ NMR (400 MHz, $CDCl_3$) δ: 1.38-1.42 (m, 3 H), 1.62-1.67 (m, 3 H), 2.02-2.14 (m, 2 H), 2.49-2.60 (m, 2 H), 3.20-3.27 (m, 2 H), 4.34-4.38 (m, 4 H).

Step 2: Synthesis of Compound 2-3

Compound 2-2 (80 mg, 298.14 μmol, 1 eq) was dissolved in tetrahydrofuran (0.5 mL), tert-butoxy bis(dimethylamino) methane (156.4 mg, 894.10 μmol, 3 eq) was added thereto, and the temperature was raised to 90° C. and the reaction was carried out for 12 hours. After the reaction was completed, the temperature was lowered to 20° C., and the solvent was removed by concentration under reduced pressure with an oil pump to obtain compound 2-3, which was directly used in the next reaction.

Characterization of Compound 2-3

$^1H$ NMR (400 MHz, $CDCl_3$) δ: 1.26-1.32 (m, 3 H), 1.45-1.52 (m, 3 H), 2.73-2.76 (m, 2 H), 3.00-3.07 (m, 8 H), 4.19-4.25 (m, 4 H), 7.51 (s, 1 H).

Step 3: Synthesis of Compound 2-4

Compound 2-3 (10 mg, 30.92 μmol, 1 eq) and compound 1-3 (8.33 mg, 26.26 μmol, 0.849 eq) were dissolved in N,N-dimethylformamide (0.5 mL) sequentially, the temperature was raised to 110° C. and the reaction was carried out for 12 hours. After the reaction was completed, water (2 mL) was added to dilute the system, and the reaction mixture was extracted with ethyl acetate (2 mL*3). The organic phases were combined, washed with saturated brine (3 mL), dried over anhydrous sodium sulfate, filtered, and the filtrate was concentrated under reduced pressure to obtain the crude product, which was separated by thin-layer chromatography (developing agent: dichloromethane:methanol=20:1) to obtain compound 2-4.

Characterization of Compound 2-4

LCMS: m/z (ESI)=578.20 $[M+H]^+$.

$^1H$ NMR (400 MHz, $CDCl_3$) δ: 1.30-1.33 (m, 3 H), 1.45-1.50 (m, 3 H), 2.30 (s, 3 H), 2.53 (s, 4 H), 2.68-2.72 (m, 2 H), 3.15-3.25 (m, 6 H), 4.25-4.29 (m, 4 H), 4.36-4.43 (m, 1 H), 7.01-7.08 (m, 1 H), 7.24 (s, 1 H), 8.21 (s, 1 H), 8.30-8.37 (m, 1 H).

Step 4: Synthesis of Compound 2

Compound 2-4 (80 mg, 138.50 μmol, 1 eq) was dissolved in tetrahydrofuran (0.5 mL), and after adding ammonium chloride (45 mg, 831.00 μmol, 6 eq), the system was cooled to 0° C., and a solution of lithium bis(trimethylsilyl)amide in tetrahydrofuran at the concentration of 1 M (1.39 mL, 1.39 mmol, 10 eq) was slowly added dropwise thereto. The temperature was raised to 20° C. slowly after the addition, and the reaction was carried out at this temperature for 2 hours, then ethanol (3 mL) was added to quench the reaction, the solvent was removed by concentrating under reduced pressure to obtain the crude product, and the crude product was purified by HPLC preparative chromatography (HPLC preparation method: Phenomenex preparative chromatograph; chromatographic column: C18 80*40 mm*3 μm; mobile phase A: aqueous solution containing 0.05% ammonia water, mobile phase B: acetonitrile; running gradient: B %: 36% to 66%, run for 8 min) to obtain compound 2.

Characterization of Compound 2

LCMS: m/z (ESI)=549.19 $[M+H]^+$.

$^1H$ NMR (400 MHz, $CDCl_3$) δ: 1.27-1.37 (m, 3 H), 2.22 (s, 3 H), 2.34 (s, 3 H), 2.68 (s, 2 H), 3.04-3.20 (m, 7 H), 4.19-4.26 (m, 2 H), 6.67 (s, 1 H), 7.17 (s, 1 H), 7.35 (s, 2 H), 7.84 (s, 1 H), 8.16-8.24 (m, 1 H), 8.32 (s, 1 H).

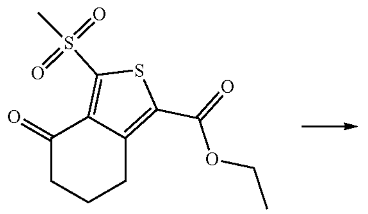

2-1

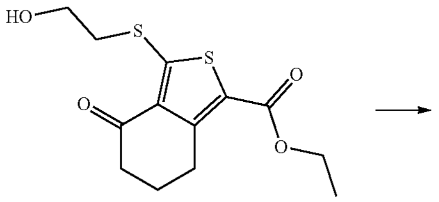

3-2

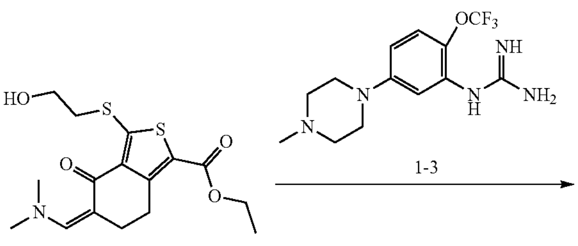

3-3

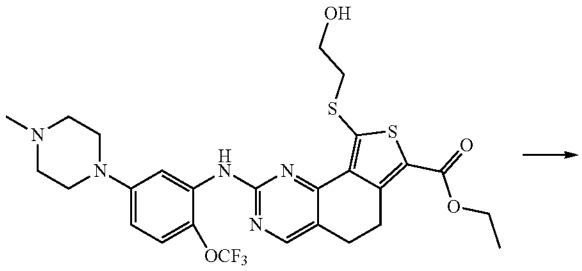

3-4

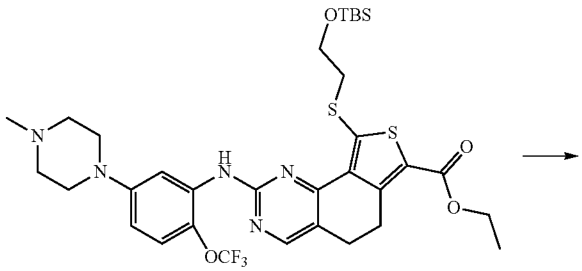

3-5

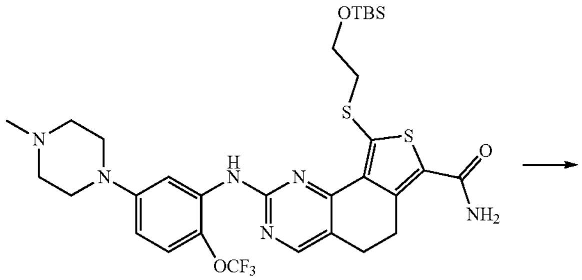

3-6

-continued

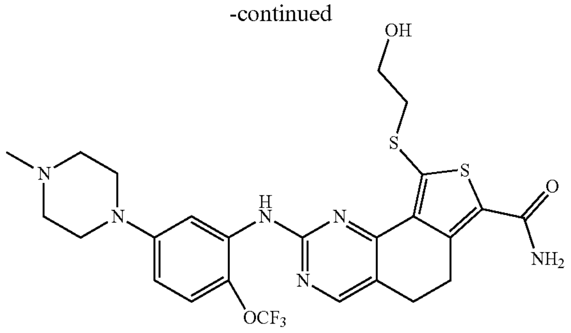

3

Step 1: Synthesis of Compound 3-2

Compound 2-1 (450 mg, 1.49 mmol, 1 eq) was dissolved in ethanol (5 mL), 2-mercaptoethanol (151.17 mg, 1.93 mmol, 134.97 1.3 eq) and triethylamine (301.19 mg, 2.98 mmol, 414.29 2 eq) were added thereto, and the reaction mixture was stirred at 20° C. for 2 hours. Water (10 mL) was added to the reaction system to dilute, then the reaction mixture was extracted with ethyl acetate (10 mL*3), and the phases were separated. The organic phases were combined, dried over anhydrous sodium sulfate, filtered, and the filtrate was concentrated to dryness under reduced pressure to obtain the crude product. The crude product was purified by silica gel column chromatography (gradient elution: petroleum ether/ethyl acetate=100:0 to 70:30) to obtain compound 3-2.

Characterization of Compound 3-2

LCMS: m/z (ESI)=301.0 $[M+H]^+$.

$^1$H NMR (400 MHz, $CDCl_3$) δ: 4.30-4.39 (m, 2 H), 3.99-4.05 (m, 2 H), 3.26-3.34 (m, 2 H), 3.17-3.24 (m, 2 H), 2.53-2.61 (m, 2 H), 2.06-2.11 (m, 2 H), 1.34-1.42 (m, 3 H).

Step 2: Synthesis of Compound 3-3

Compound 3-2 (260 mg, 865.53 μmol, 1 eq) was dissolved in tetrahydrofuran (5 mL), tert-butoxy bis(dimethylamino)methane (452.54 mg, 2.60 mmol, 536.18 3 eq) was added thereto, and the reaction mixture was stirred at 80° C. for 16 hours. The reaction system was cooled to 20° C., then water (20 mL) was added to the reaction system to dilute, then ethyl acetate (10 mL) was added thereto, and the reaction mixture was stirred, filtered. The filter cake was slurried with ethanol (10 mL) for 0.5 hours, filtered, and the filter cake was concentrated under reduced pressure with an oil pump to remove the residue to obtain compound 3-3.

Characterization of Compound 3-3

$^1$H NMR(400 MHz, $CDCl_3$) δ: 7.65 (s, 1 H), 4.28-4.37 (m, 2 H), 3.88-3.98 (m, 2 H), 3.21-3.28 (m, 2 H), 3.15-3.20 (m, 2 H), 3.14 (s, 6 H), 2.82-2.91 (m, 2 H), 1.32-1.43 (m, 3 H).

Step 3: Synthesis of Compound 3-4

Compound 3-3 (300 mg, 843.95 μmol, 1 eq) was dissolved in N,N-dimethylaminoformamide (5 mL), compound 1-3 (267.79 mg, 843.95 μmol, 1 eq) was added thereto, and the reaction mixture was stirred at 110° C. for 16 hours. Saturated brine (15 mL) was added to the reaction system, the reaction mixture was extracted with ethyl acetate (5 mL*3), and the phases were separated. The organic phases were combined, dried over anhydrous sodium sulfate, filtered, and concentrated to dryness under reduced pressure to obtain the crude product. The crude product was purified by silica gel column chromatography (gradient elution: dichloromethane/methanol=100:0 to 90:10) to obtain compound 3-4.

Characterization of Compound 3-4

LCMS: m/z (ESI)=610.20 $[M+H]^+$.

$^1$H NMR (400 MHz, $CD_3OD$) δ: 8.29 (s, 1 H), 7.88-7.93 (m, 1 H), 7.15-7.22 (m, 1 H), 6.66-6.76 (m, 1 H), 4.29-4.36 (m, 2 H), 3.79-3.89 (m, 2 H), 3.26-3.30 (m, 6 H), 3.21-3.25 (m, 4 H), 2.78-2.85 (m, 2 H), 2.69 (s, 3 H), 2.39-2.44 (m, 2 H), 1.33-1.39 (m, 3 H).

Step 4: Synthesis of Compound 3-5

Compound 3-4 (100 mg, 164.02 μmol, 1 eq) was dissolved in dichloromethane (2 mL), and triethylamine (24.90 mg, 246.03 μmol, 34.24 μL, 1.5 eq) and 4-dimethylaminopyridine (2.00 mg, 16.40 μmol, 0.1 eq) were added thereto, then tert-butyldimethylsilyl chloride (29.67 mg, 196.82 μmol, 24.12 μL, 1.2 eq) was added thereto, and the reaction mixture was stirred at 20° C. for 20 hours. The reaction mixture was concentrated to dryness under reduced pressure to obtain the crude product, which was purified by thin-layer chromatography (developing agent: dichloromethane/methanol=10:1) to obtain compound 3-5.

Characterization of Compound 3-5

LCMS: m/z (ESI)=724.30 $[M+H]^+$.

$^1$H NMR (400 MHz, $CD_3OD$) δ: 8.29 (s, 1 H), 7.94-8.00 (m, 1 H), 7.12-7.20 (m, 1 H), 6.65-6.73 (m, 1 H), 4.27-4.36 (m, 2 H), 3.91-3.99 (m, 2 H), 3.25-3.29 (m, 6 H), 3.21-3.25 (m, 2 H), 2.78-2.87 (m, 2 H), 2.60-2.70 (m, 4 H), 2.37 (s, 3 H), 1.32-1.40 (m, 3 H), 0.84 (s, 9 H), −0.01 (s, 6 H).

Step 5: Synthesis of Compound 3-6

Compound 3-5 (70 mg, 96.69 μmol, 1 eq) was dissolved in tetrahydrofuran (1 mL), ammonium chloride (31.03 mg, 580.16 μmol, 6 eq) was added, then the temperature was lowered to 0° C., and a solution of lithium bis(trimethylsilyl) amide in tetrahydrofuran at the concentration of 1 M (966.93 μL, 10 eq) was added thereto, the temperature was raised to 20° C. and the reaction mixture was stirred for 4 hours. Water (5 mL) was added to the reaction system, then the reaction system was extracted by adding ethyl acetate (5 mL*3). The phases were separated, and the organic phases were combined, dried over anhydrous sodium sulfate, filtered, and concentrated under reduced pressure to remove the solvent to obtain compound 3-6.

Characterization of Compound 3-6

LCMS: m/z (ESI)=695.20 $[M+H]^+$.

$^1$H NMR (400 MHz, $CD_3OD$) δ: 8.29 (s, 1 H), 7.99-8.03 (m, 1 H), 7.14-7.21 (m, 1 H), 6.64-6.71 (m, 1 H), 3.90-3.96 (m, 2 H), 3.24-3.29 (m, 6 H), 3.21-3.24 (m, 2 H), 2.79-2.86 (m, 2 H), 2.58-2.65 (m, 4 H), 2.37 (s, 3 H), 0.84 (s, 9 H), -0.02 (s, 6 H).

Step 6: Synthesis of Compound 3

Compound 3-6 (60 mg, 86.34 μmol, 1 eq) was dissolved in tetrahydrofuran (0.5 mL) solution, and then a solution (172.69 μL, 2 eq) of tetrabutylammonium fluoride in tetrahydrofuran at a concentration of 1 M was added thereto, and the resulting reaction mixture was stirred at 20° C. for 2 hours. Water (10 mL) was added to the reaction system to wash, then ethyl acetate (10 mL*3) was added thereto for extraction, and the phases were separated. The organic phases were combined, dried over anhydrous sodium sulfate, filtered, and concentrated under reduced pressure to obtain the crude product. The crude product was purified by HPLC preparative chromatography (HPLC preparation method: Waters Xbridge BEH preparative chromatograph; chromatographic column: C18 100*30 mm*10 μm; mobile phase A: 10 mM ammonium bicarbonate aqueous solution (containing 0.05% ammonia water), mobile phase B: acetonitrile; running gradient: B %: 25% to 55%, run for 8 min) to obtain compound 3.

Characterization of Compound 3

LCMS: m/z (ESI)=581.30 $[M+H]^+$.

$^1H$ NMR (400 MHz, DMSO-$d_6$) δ: 8.43 (s, 1 H), 8.32 (s, 1 H), 7.40-7.48 (m, 3 H), 7.13-7.20 (m, 1 H), 6.68-6.75 (m, 1 H), 5.02-5.09 (m, 1 H), 3.63-3.71 (m, 2 H), 3.12 -3.17 (m, 4 H), 3.04-3.11 (m, 4 H), 2.71-2.76 (m, 2 H), 2.42- 2.46 (m, 4 H), 2.07 (s, 3 H).

Example 4

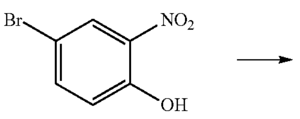

4-1

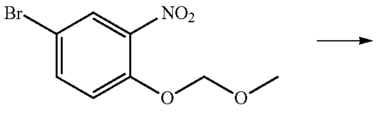

4-2

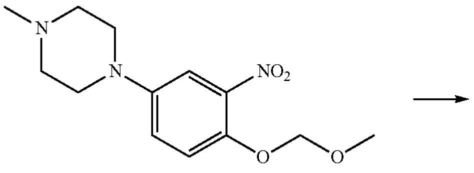

4-3

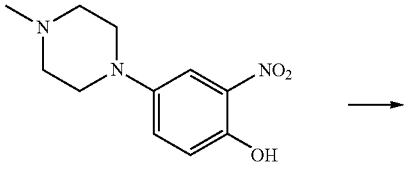

4-4

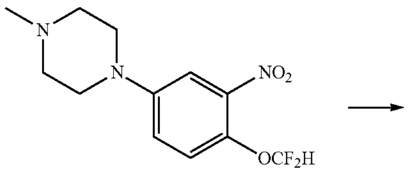

4-5

-continued

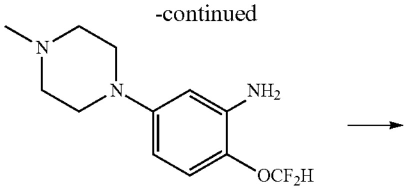

4-6

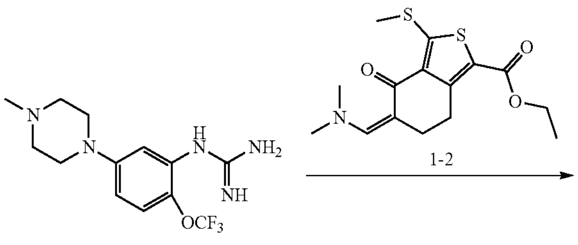

1-2

4-7

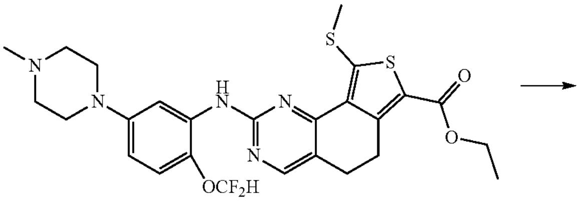

4-8

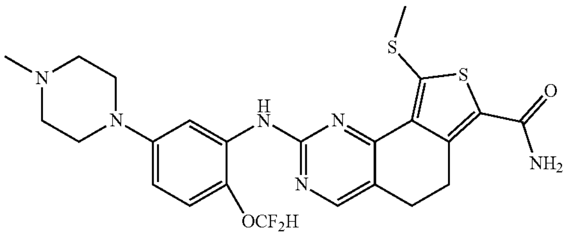

4

Step 1: Synthesis of Compound 4-2

Compound 4-1 (10 g, 45.87 mmol, 1 eq) was dissolved in dichloromethane (300 mL), N,N-diisopropylethylamine (8.90 g, 68.89 mmol, 12.00 mL, 1.50 eq) and chloromethyl methyl ether (4.47 g, 55.52 mmol, 4.22 mL, 1.21 eq) were added thereto, the reaction mixture was stirred at 20° C. for 4 hours. After the reaction mixture was concentrated to dryness under reduced pressure, water (150 mL) and dichloromethane (150 mL) were added to the crude product. The phases were separated, the organic phase was dried over anhydrous sodium sulfate, filtered, and the solvent was concentrated to dryness under reduced pressure to obtain the crude product. The crude product was purified by silica gel column chromatography (gradient elution: petroleum ether/ethyl acetate=100:0 to 90:10) to obtain compound 4-2.

Characterization of Compound 4-2

$^1H$ NMR (400 MHz, $CDCl_3$) δ: 3.53 (s, 3 H), 5.29 (s, 2 H), 7.20 — 7.28 (m, 1 H), 7.61 (s, 1 H), 7.92-7.99 (m, 1 H).

Step 2: Synthesis of Compound 4-3

Compound 4-2 (2 g, 7.63 mmol, 1 eq) was dissolved in toluene (12 mL) and dimethyl sulfoxide (4 mL), then N-methylmorpholine (1.15 g, 11.45 mmol, 1.27 mL, 1.5 eq), cesium carbonate (7.46 g, 22.90 mmol, 3 eq), tris(dibenzylideneacetone)dipalladium (139.77 mg, 152.64 μmol, 0.02 eq), (S)-(−)-2,2-bis(di-p-tolylphosphine)-1,1-binaphthyl (207.22 mg, 305.28 μmol, 0.04 eq) were added thereto sequentially, and the mixture was stirred at 90° C. for 16 hours under nitrogen atmosphere. The reaction mixture was filtered through a funnel covered with diatomite, and the filter cake was rinsed with ethyl acetate (150 mL). After the filtrate was concentrated to dryness under reduced pressure, ethyl acetate (50 mL) and saturated brine (50 mL) were added to the crude product. The phases were separated, and the organic phase was dried over anhydrous sodium sulfate, filtered, and the solvent was concentrated to dryness under reduced pressure to obtain the crude product. The crude product was purified by silica gel column chromatography (gradient elution: dichloromethane/methanol=100:0 to 98:2) to obtain compound 4-3.

Characterization of Compound 4-3

LCMS: m/z (ESI)=282.0 $[M+H]^+$.

$^1$H NMR (400 MHz, $CDCl_3$) δ: 2.37 (s, 3 H), 2.55-2.61 (m, 4 H), 3.14-3.24 (m, 4 H), 3.53 (s, 3 H), 5.20 (s, 2 H), 7.09 (s, 1 H), 7.22-7.26 (m, 1 H), 7.30 -7.36 (m, 1 H).

Step 3: Synthesis of Compound 4-4

Compound 4-3 (950 mg, 3.38 mmol, 1 eq) was dissolved in dichloromethane (10 mL), then methanol (8.4 mL) and concentrated hydrochloric acid (1.6 mL, 5.69 eq) at a concentration of 12 M were added, and the mixture was stirred at 15° C. for 16 hours. The temperature was raised to 35° C. and the mixture was stirred for 8 hours. The solvent was concentrated to dryness under reduced pressure to obtain the hydrochloride of compound 4-4.

Characterization of the hydrochloride of compound 4-4

LCMS: m/z (ESI)=238.1 $[M+H]^+$.

Step 4: Synthesis of Compound 4-5

The hydrochloride of compound 4-4 (400 mg, 1.46 mmol, 1 eq) was dissolved in dichloromethane (8 mL), and after cooling to 0° C. in an ice bath, a mixture of potassium hydroxide (491.95 mg, 8.77 mmol, 6 eq) and water (2.4 mL) was added thereto, and (bromodifluoromethyl)trimethylsilane (605.72 mg, 2.92 mmol, 2 eq) was added thereto at 0° C., and the mixture was stirred at 20° C. for 16 hours. Dichloromethane (5 mL) and water (5 mL) were added to the reaction mixture for extraction, then the phases were separated. The organic phase was dried over anhydrous sodium sulfate, filtered, and the solvent was concentrated to dryness under reduced pressure to obtain the crude product. The crude product was separated by thin-layer chromatography (developing agent: dichloromethane/methanol=10:1) to obtain compound 4-5.

Characterization of Compound 4-5

$^1$H NMR (400 MHz, $CDCl_3$) δ: 2.44-2.54 (m, 3 H), 2.67-2.84 (m, 4 H), 3.37 (s, 4 H), 6.26-6.75 (m, 1 H), 7.06-7.10 (m, 1 H), 7.26 (s, 1 H), 7.30- 7.40 (m, 1 H).

Step 5: Synthesis of Compound 4-6

Wet palladium carbon (50 mg) with purity of 10%, methanol (5 mL) and compound 4-5 (30 mg, 104.43 μmol, 1 eq) were added thereto sequentially under micron argon flow environment, and the reaction mixture was reacted under hydrogen (15 psi) conditions at 15° C. for 2 hours. The reaction mixture was directly filtered, and the solvent of the filtrate was concentrated to dryness under reduced pressure to obtain compound 4-6.

Characterization of Compound 4-6

$^1$H NMR (400 MHz, $CD_3OD$) δ: 2.92 (s, 3 H), 3.05-3.71 (m, 8 H), 6.26 -6.32 (m, 1 H), 6.36-6.78 (m, 2 H), 6.91 -6.95 (m, 1 H).

Step 6: Synthesis of Compound 4-7

Compound 4-6 (18 mg, 69.96 μmol, 1 eq) was dissolved in a 6 M hydrochloric acid aqueous solution (180.00 μL, 15.44 eq), then aminonitrile (61.92 mg, 1.40 mmol, 61.92 μL, 20 eq) was added thereto, and the mixture was stirred at 60° C. for 1 hour. Water (5 mL) and dichloromethane (5 mL) were added to the reaction mixture, then the phases were separated, and solid sodium hydroxide was added to the aqueous phase to adjust the pH of the aqueous phase to greater than 12, then ethyl acetate (5 mL*2) was added for extraction. The phases were separated, and the organic phases were combined, dried over anhydrous sodium sulfate, filtered, and the solvent was concentrated to dryness under reduced pressure to obtain compound 4-7.

Characterization of Compound 4-7

LCMS: m/z (ESI)=300.1 $[M+H]^+$.

Step 7: Synthesis of Compound 4-8

Compound 1-2 (20 mg, 44.68 μmol, 2.4 eq) was dissolved in N,N-dimethylformamide (0.5 mL), then compound 4-7 (6.26 mg, 18.62 μmol, 1 eq) was added thereto, and the reaction mixture was stirred at 110° C. for 12 hours. Saturated brine (5 mL) and water (5 mL) were added to the reaction mixture, then the reaction mixture was extracted with ethyl acetate (5 mL*6). The phases were separated, and the organic phases were combined, washed with saturated brine (5 mL*6), dried over anhydrous sodium sulfate, and filtered, and the solvent was concentrated to dryness under reduced pressure to obtain the crude product. The crude product was purified by HPLC preparative chromatography (HPLC preparation method: Phenomenex preparative chromatograph; chromatographic column: C18 75*30 mm*3 μm; mobile phase A: 0.1% ammonium bicarbonate aqueous solution, mobile phase B: acetonitrile; running gradient: B %: 55% to 85%, run for 12 min) to obtain compound 4-8.

Characterization of Compound 4-8

LCMS: m/z (ESI)=562.2 $[M+H]^+$.

$^1$H NMR (400 MHz, $CD_3OD$) δ: 1.20- 1.28 (m, 3 H), 2.36 (s, 3 H), 2.58-2.65 (m, 7 H), 2.80 -2.86 (m, 2 H), 3.19-3.26 (m, 4 H), 3.25 -3.30 (m, 2 H), 4.30 -4.36 (m, 2 H), 6.69 -6.73 (m, 2 H), 7.04-7.13 (m, 1 H), 8.00 -8.05 (m, 1 H), 8.28 (s, 1 H).

Step 8: Synthesis of Compound 4

Compound 4-8 (2 mg, 3.56 μmol, 1 eq) was dissolved in anhydrous tetrahydrofuran (1 mL), then ammonium chloride (38.09 mg, 712.17 μmol, 200 eq) and a solution (1.42 mL, 400 eq) of lithium bis(trimethylsilyl)amide in tetrahydrofuran at a concentration of 1 M were added thereto, and the mixture was stirred at 20° C. for 3 hours. The reaction was quenched by adding methanol (5 mL), and the solvent was concentrated to dryness under reduced pressure to obtain the crude product. The crude product was purified by HPLC preparative chromatography (HPLC preparation method: Waters Xbridge BEH preparative chromatograph; chromatographic column: C18 100*25 mm*5 μm; mobile phase A: 0.1% ammonium bicarbonate aqueous solution, mobile phase B: acetonitrile; running gradient: B %: 20% to 55%, run for 10 min) to obtain compound 4.

Characterization of Compound 4

LCMS: m/z (ESI)=533.2 $[M+H]^+$.

$^1H$ NMR (400 MHz, $CD_3OD$) δ: 2.36 (s, 3 H), 2.59-2.69 (m, 5 H), 2.82 -2.86 (m, 2 H), 3.11-3.27 (m, 8 H), 6.50-6.93 (m, 2 H), 7.05-7.25 (m, 1 H), 8.03 (d, J=2.86 Hz, 1 H), 8.29 (s, 1 H).

Example 5

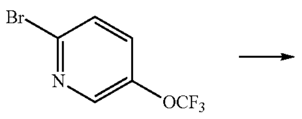

5-1

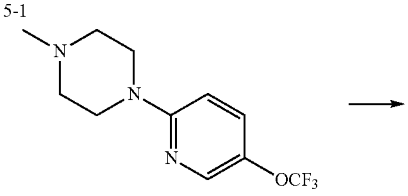

5-2

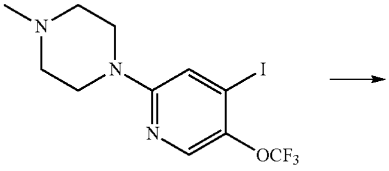

5-3

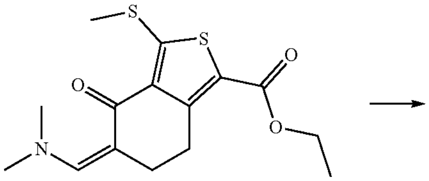

1-2

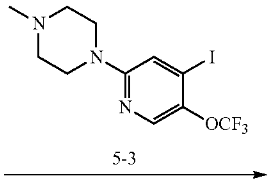

5-3

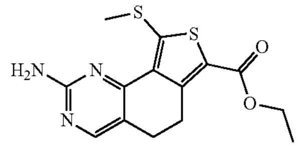

5-4

-continued

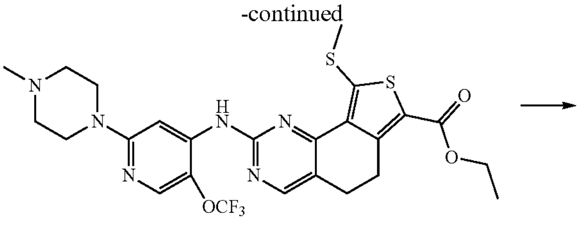

5-5

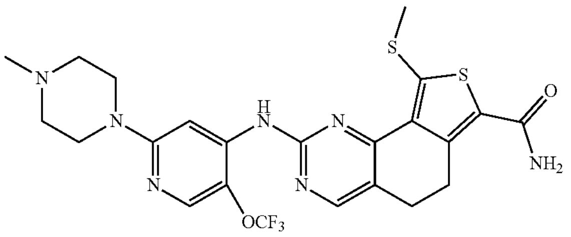

5

Step 1: Synthesis of Compound 5-2

Compound 5-1 (2 g, 8.26 mmol, 1 eq) was dissolved in toluene (20 mL), then N-methylpiperazine (827.81 mg, 8.26 mmol, 916.73 μL, 1.00 eq), sodium tert-butoxide (1.19 g, 12.40 mmol, 1.5 eq), tris(dibenzylideneacetone)dipalladium (378.41 mg, 413.23 μmol, 0.05 eq) and (R)-(+)-2,2-bis (diphenylphosphino)-1,1-binaphthyl (257.31 mg, 413.23 μmol, 0.05 eq) were added thereto, and the mixture was stirred at 80° C. for 16 hours under nitrogen atmosphere. Water (5 mL) was added to the reaction mixture to quench the reaction, and the reaction mixture was extracted with ethyl acetate (5 mL*3). The phases were separated, and the organic phases were combined, and concentrated under reduced pressure to obtain the crude product. The crude product was purified by silica gel column chromatography (gradient elution: dichloromethane/methanol=100:0 to 95:5) to obtain compound 5-2.

Characterization of Compound 5-2

LCMS: m/z (ESI)=262.30 $[M+H]^+$.

$^1H$ NMR (400 MHz, $CDCl_3$) δ: 8.07-8.14 (m, 1 H), 7.32-7.39 (dd, J=9.2 Hz, 1 H), 6.57-6.67 (d, J=9.2 Hz, 1 H), 3.52-3.61 (t, J=5.2 Hz, 4 H), 2.46-2.58 (t, J=5.2 Hz, 4 H), 2.36 (s, 3 H).

Step 2: Synthesis of Compound 5-3

Under nitrogen atmosphere at −78° C., compound 5-2 (500 mg, 1.91 mmol, 1 eq) was dissolved in tetrahydrofuran (5 mL) solution, and a 2 M solution (1.44 mL, 1.5 eq) of lithium diisopropylamide in tetrahydrofuran was added thereto, and the resulting reaction mixture was stirred at −78° C. for 2 hours, then a solution of iodine (728.65 mg, 2.87 mmol, 1.5 eq) in anhydrous THF (2 mL) was added thereto. The reaction mixture was stirred at −78° C. for 2, hours, and then the reaction system was heated to 80° C. and stirred for 16 hours. Water (10 mL) was added to the reaction system to quench the reaction, and the reaction mixture was extracted with ethyl acetate (15 mL*3). The phases were separated, and the organic phases were combined, dried over anhydrous sodium sulfate, filtered, and the filtrate was concentrated to dryness under reduced pressure to obtain the crude product. The crude product was purified by silica gel column chromatography (gradient elution: dichloromethane/methanol=100:0 to 95:5) to obtain compound 5-3.

Characterization of Compound 5-3

LCMS: m/z (ESI)=388.00 $[M+H]^+$.

$^1H$ NMR (400 MHz, $CDCl_3$) δ: 7.99-8.06 (m, 1 H), 7.09 (s, 1 H), 3.55-3.67 (m, 4 H), 2.48-2.65 (m, 4 H), 2.40 (s, 3 H).

Step 3: Synthesis of Compound 5-4

Compound 1-2 (300 mg, 921.81 μmol, 1 eq) was dissolved in N,N-dimethylformamide (5 mL), and guanidine carbonate (415.20 mg, 2.30 mmol, 2.5 eq) was added thereto, and the mixture was stirred at 110° C. for 3 hours. Water (10 mL) was added to the reaction mixture, and the reaction mixture was stirred for 0.5 hours, filtered. The filter cake was rinsed with methanol (10 mL), and the residue was removed under reduced pressure with an oil pump to obtain compound 5-4.

Characterization of Compound 5-4

LCMS: m/z (ESI)=321.90 $[M+H]^+$.

$^1H$ NMR (400 MHz, DMSO-$d_6$) δ: 8.13 (s, 1 H), 6.31-6.39 (m, 2 H), 4.22-4.31 (m, 2 H), 3.14-3.21 (m, 2 H), 2.65-2.72 (m, 2 H), 2.61 (s, 3 H), 1.25-1.33 (m, 3 H).

Step 4: Synthesis of Compound 5-5

Compound 5-4 (49.81 mg, 154.98 μmol, 1 eq) was dissolved in 1,4-dioxane (2 mL), and tris(dibenzylideneacetone)dipalladium (14.19 mg, 15.50 μmol, 0.1 eq), 4,5-bis (diphenylphosphino)-9,9-dimethylxanthene (8.97 mg, 15.50 μmol, 0.1 eq), cesium carbonate (100.99 mg, 309.97 μmol, 2 eq), and compound 5-3 (60 mg, 154.98 μmol, 1 eq) were added thereto, and the mixture was stirred at 100° C. for 3 hours. Water (10 mL) was added to the reaction mixture to quench the reaction, then the reaction mixture was extracted with ethyl acetate (10 mL*3). The phases were separated, and the organic phases were combined, dried over anhydrous sodium sulfate, filtered, and the filtrate was concentrated under reduced pressure to obtain the crude product. The crude product was purified by silica gel column chromatography (gradient elution: dichloromethane/methanol=100:0 to 95:5) to obtain compound 5-5.

Characterization of Compound 5-5

LCMS: m/z (ESI)=581.20 $[M+H]^+$.

$^1H$ NMR (400 MHz, $CDCl_3$) δ: 1.40 -1.46 (m, 3 H), 2.38 (3 H), 2.53-2.65 (m, 4 H), 2.67 (s, 3 H), 2.83 -2.86 (m, 2 H), 3.23-3.37 (m, 6 H), 4.35 -4.39 (m, 2 H), 6.50-6.55 (m, 1 H), 7.12 -7.16 (m, 1 H), 8.24 -8.30 (m, 1 H), 8.30 (s, 1 H).

Step 5: Synthesis of Compound 5

Compound 5-5 (90 mg, 155.00 μmol, 1 eq) was dissolved in tetrahydrofuran (2 mL), ammonium chloride (49.75 mg, 930.00 μmol, 6 eq) was added thereto, and a solution (3.10 mL, 20 eq) of lithium bis(trimethylsilyl)amide in tetrahydrofuran at a concentration of 1 M was added at 0° C. under nitrogen atmosphere, and the mixture was stirred at 20° C. for 3 hours. Water (10 mL) was added to the reaction system to quench the reaction, then ethyl acetate (15 mL*3) was added for extraction. The phases were separated, and the organic phases were combined and concentrated under reduced pressure to obtain the crude product, which is purified by HPLC preparative chromatography (high performance liquid phase preparation method: Waters Xbridge BEH Preparative Chromatography; chromatographic column: C18 100*30 mm*10 μm; mobile phase A: 10 mM ammonium bicarbonate aqueous solution (containing 0.05% ammonia), mobile phase B: acetonitrile; running gradient: B %: 30% to 60%, run for 8 min) to obtain compound 5.

Characterization of Compound 5

LCMS: m/z (ESI)=552.20 $[M+H]^+$.

$^1H$ NMR (400 MHz, DMSO-$d_6$) δ: 8.77 (s, 1 H), 8.48 (s, 1 H), 8.02-8.06 (m, 1 H), 7.70 (s, 1 H), 7.47 (s, 2 H), 3.45-3.53 (m, 4 H), 3.10-3.19 (m, 2 H), 2.77-2.84 (m, 2 H), 2.61 (s, 3 H), 2.36-2.41 (m, 4 H), 2.20 (s, 3 H).

Example 6

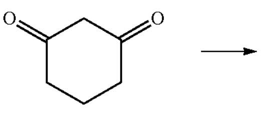

6-1

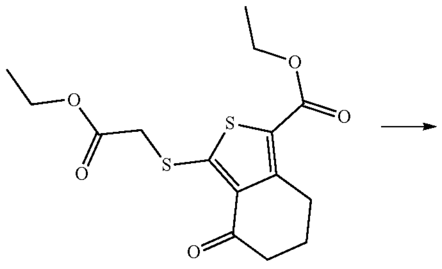

6-2

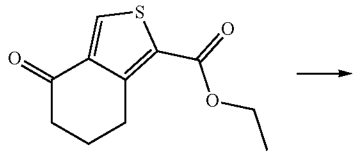

6-3

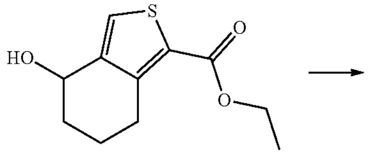

6-4

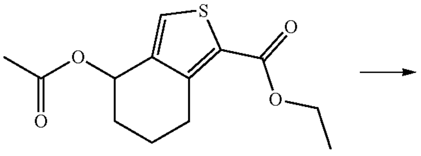

6-5

-continued

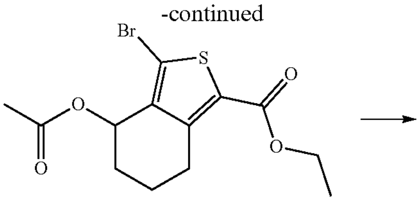

6-6

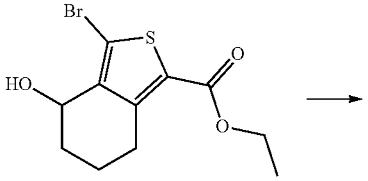

6-7

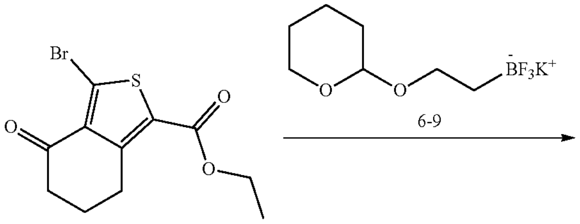

6-9

6-8

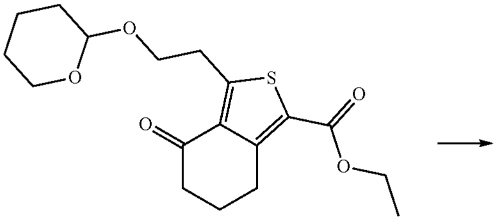

6-10

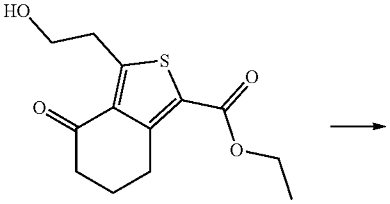

6-11

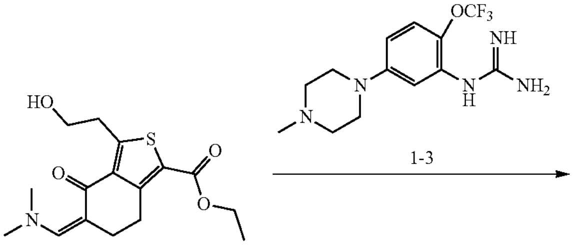

1-3

6-12

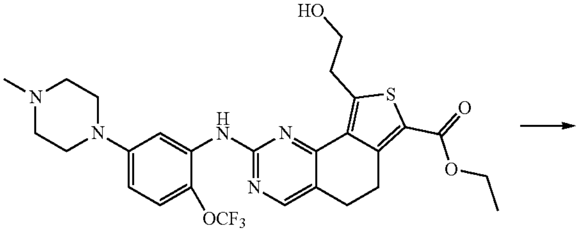

6-13

-continued

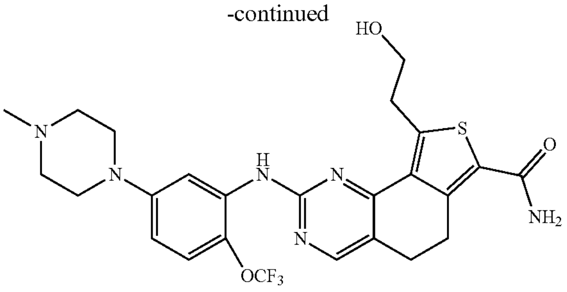

6

Step 1: Synthesis of Compound 6-2

Potassium carbonate (51.77 g, 374.58 mmol, 2 eq) was dissolved in dimethyl sulfoxide (200 mL), then compound 6-1 (21 g, 187.29 mmol, 1 eq) was added thereto, and the mixture was stirred at 20° C. for 10 minutes, then carbon disulfide (15.69 g, 206.02 mmol, 12.45 mL, 1.1 eq) was added thereto, and the mixture was stirred at 20° C. for 10 minutes. Then a mixture of ethyl bromoacetate (31.28 g, 187.29 mmol, 20.71 mL, 1 eq) and methyl iodide (26.58 g, 187.29 mmol, 11.66 mL, 1 eq) was added thereto at 0° C., and the temperature was controlled at 15 to 20° C. After the dropwise addition, the mixture was stirred at 20° C. for 1 hour. Water (500 mL) and saturated brine (300 mL) were added to the reaction mixture, and the reaction mixture was extracted with ethyl acetate (500 mL*3), and the phases were separated. The organic phases was combined and washed with saturated brine (500 mL), and the phases were separated. The organic phase was dried over anhydrous sodium sulfate, filtered, and the solvent was concentrated to dryness under reduced pressure to obtain the crude product, which was purified by silica gel column chromatography (gradient elution: petroleum ether/ethyl acetate=100:0 to 90:10) to obtain the product. Then the product was slurried with methyl tert-butyl ether (15 mL) for 1 hour, filtered, and the filter cake was collected to obtain compound 6-2.

Characterization of Compound 6-2

LCMS: m/z (ESI)=343.0 $[M+H]^+$.

$^1H$ NMR (400 MHz, $CDCl_3$) δ: 1.28-1.34 (m, 3 H), 1.34-1.42 (m, 3 H), 1.92-2.16 (m, 2 H), 2.48-2.68 (m, 2 H), 3.18-3.26 (m, 2 H), 3.86 (s, 2 H), 4.18-4.44 (m, 4 H).

Step 2: Synthesis of Compound 6-3

Raney nickel (5.20 g, 60.70 mmol, 4.00 eq) and ethanol (150 mL) were added under a micron argon flow, and then compound 6-2 (5.2 g, 15.19 mmol, 1 eq) was added thereto, and the reaction mixture was reacted under hydrogen (50 psi) at 30° C. for 48 hours. The reaction mixture was filtered a funnel covered with diatomite, and the filter cake was rinsed with ethanol (800 mL). The filtrate was concentrated to dryness under reduced pressure to obtain the crude product, which was purified by silica gel column chromatography (gradient elution: petroleum ether/ethyl acetate=100:0 to 90:10) to obtain the product, and the product was dissolved in methyl tert-butyl ether (20 mL) and then petroleum ether (30 mL) was added thereto. The mixture was slurried for 1 hour and filtered, and the filter cake was collected to obtain compound 6-3.

Characterization of Compound 6-3

$^1$H NMR (400 MHz, $CDCl_3$) δ: 1.40 -1.50 (m, 3 H), 1.96-2.24 (m, 2 H), 2.41-2.75 (m, 2 H), 3.23 -3.26 (m, 2 H), 4.34-4.40 (m, 2 H), 8.29 (s, 1 H).

Step 3: Synthesis of Compound 6-4

Compound 6-3 ((1 g, 4.46 mmol, 1 eq) was dissolved in anhydrous ethanol (20 mL), sodium borohydride (280 mg, 7.40 mmol, 1.66 eq) was added thereto, and the mixture was stirred at 20° C. for 2 hours. After water (10 mL) was added to the reaction mixture, the pH value was adjusted to 6 with 1 M dilute hydrochloric acid aqueous solution, the reaction mixture was concentrated under reduced pressure until the solvent was no longer reduced. Water (10 mL) and saturated saline (10 mL) were added to the crude product, and the mixture was extracted with ethyl acetate (40 mL*2). The phases were separated, the organic phases were combined, dried over anhydrous sodium sulfate, filtered, and the solvent was concentrated to dryness under reduced pressure. The crude product was purified by silica gel column chromatography (gradient elution:petroleum ether/ethyl acetate=100:0 to 90:10) to obtain compound 6-4.

Characterization of Compound 6-4

LCMS: m/z (ESI)=209.1 [M−17]$^+$.

$^1$H NMR (400 MHz, $CDCl_3$) δ: 1.34-1.40 (m, 3 H), 1.54-1.83 (m, 3 H), 1.92-2.12 (m, 2 H), 3.03-3.09 (m, 2 H), 4.33 -4.38 (m, 2 H), 4.74-4.87 (m, 1 H), 7.53 (s, 1 H).

Step 4: Synthesis of Compound 6-5

Compound 6-4 (8 g, 35.35 mmol, 1 eq) was dissolved in dichloromethane (110 mL), and then acetyl chloride (11.10 g, 141.41 mmol, 10.09 mL, 4 eq) and 4-dimethylaminopyridine (431.90 mg, 3.54 mmol, 0.1 eq), pyridine (13.98 g, 176.76 mmol, 14.27 mL, 5 eq) were added thereto, the mixture was stirred at 20° C. for 2 hours. The solvent of the reaction mixture was concentrated under reduced pressure to ⅓ of the original volume, and then water (30 mL) was added thereto. The phases were separated, and the organic phase was washed with water (30 mL), then the phases were separated. The organic phase was dried over anhydrous sodium sulfate, filtered, and the solvent was concentrated to dryness under reduced pressure to obtain the crude product, which was purified by silica gel column chromatography (gradient elution: petroleum ether/ethyl acetate=100:0 to 85:15) to obtain compound 6-5.

Characterization of Compound 6-5

LCMS: m/z (ESI)=209.0 [M−59]$^+$.

$^1$H NMR (400 MHz, $CDCl_3$) δ: 1.37 -1.40 (m, 3 H), 1.78-2.01 (m, 4 H), 2.08 (s, 3 H), 2.76-3.30 (m, 2 H), 4.33 -4.38 (m, 2 H), 5.93 -6.00 (m, 1 H), 7.52 (s, 1 H).

Step 5: Synthesis of Compound 6-6

Compound 6-5 (3.1 g, 11.55 mmol, 1 eq) was dissolved in N,N-dimethylformamide (31 mL), and then N-bromosuccinimide (6.37 g, 35.81 mmol, 3.1 eq) was added thereto, and the mixture was stirred at 50° C. for 16 hours. Ethyl acetate (50 mL) and saturated brine (50 mL) were added to the reaction mixture, and the phases were separated. The organic phase was dried over anhydrous sodium sulfate and filtered, and the solvent was concentrated to dryness under reduced pressure to obtain the crude product, which was purified by silica gel column chromatography (gradient elution: petroleum ether/ethyl acetate=100:0 to 95:5) to obtain compound 6-6.

Characterization of Compound 6-6

LCMS: m/z (ESI)=286.9,288.9 [M−59]$^+$.

$^1$H NMR(400 MHz, $CDCl_3$) δ: 1.31-1.40 (m, 3 H), 1.71-1.89 (m, 3 H), 2.09 (s, 3 H), 2.19 (s, 1 H), 2.64-2.79 (m, 1 H), 3.29-3.49 (m, 1 H), 4.32 -4. 39 (m, 2 H), 5.86-6.20 (m, 1 H).

Step 6: Synthesis of Compound 6-7

Compound 6-6 (3.7 g, 10.66 mmol, 1 eq) was dissolved in ethanol (37 mL), then potassium carbonate (1.47 g, 10.66 mmol, 1 eq) was added, and the mixture was stirred at 40° C. for 16 hours, then heated to 60° C. and stirred for 4 hours. After the reaction mixture was filtered, the filter cake was rinsed with ethanol (500 mL), and the filtrate was collected and the solvent was concentrated to dryness under reduced pressure to obtain the crude product, which was purified by silica gel column chromatography (gradient elution: petroleum ether/ethyl acetate=100:0 to 90:10) to obtain compound 6-7.

Characterization of Compound 6-7

LCMS: m/z (ESI)=286.9,288.8 [M−17]$^+$.

$^1$H NMR (400 MHz, $CDCl_3$) δ: 1.36 -1.42 (m, 3 H), 1.77-1.80 (m, 4 H), 2.02-2.20 (m, 1 H), 2.61-2.81 (m, 1 H), 3.24-3.44 (m, 1 H), 4.32 -4.40 (m, 2 H), 4.88 -4.93 (m, 1 H).

Step 7: Synthesis of Compound 6-8

Compound 6-7 (1.76 g, 5.77 mmol, 1 eq) was dissolved in dichloromethane (30 mL), and then pyridinium chlorochromate (3.73 g, 17.30 mmol, 3 eq) and sodium acetate (1.42 g, 17.30 mmol, 3 eq) were added thereto, and the mixture was stirred at 20° C. for 2 hours. The reaction mixture was filtered through a funnel covered with diatomite, rinsed with ethyl acetate (50 mL) and dichloromethane (50 mL), and the solvent was concentrated to dryness under reduced pressure to obtain the crude product, which was purified by silica gel column chromatography (gradient elution: petroleum ether/ethyl acetate=100:0 to 80:20) to obtain compound 6-8.

Characterization of Compound 6-8

LCMS: m/z (ESI)=302.9,304.9 [M+H]$^+$.

$^1$H NMR (400 MHz, $CDCl_3$) δ: 1.38-1.42 (m, 3 H), 2.10 -2.15 (m, 2 H), 2.59-2.65 (m, 2 H), 3.27 -3.30 (m, 2 H), 4.35-4.40 (m, 2 H).

Step 8: Synthesis of Compound 6-10

Compound 6-8 (203 mg, 669.59 μmol, 1 eq), compound 6-9 (332.79 mg, 1.34 mmol, 2 eq), 2-dicyclohexylphosphino-2',6'-diisopropoxybiphenyl (62.49 mg, 133.92 μmol, 0.2 eq), bis(acetonitrile)palladium(II) chloride (17.37 mg, 66.96 μmol, 0.1 eq), cesium carbonate (654.49 mg, 2.01 mmol, 3 eq) were added to a reaction flask, then a mixture of water (1 mL) and tert-butanol (1 mL) was added thereto, and the mixture was stirred at 100° C. for 16 hours under nitrogen atmosphere. Ethyl acetate (100 mL), saturated brine (50 mL) and water (50 mL) were added to the reaction mixture, and the phases were separated. The organic phase was dried over anhydrous sodium sulfate, filtered, and the solvent was concentrated to dryness under reduced pressure to obtain the crude product, which was purified by silica gel column chromatography (gradient elution: petroleum ether/ethyl acetate=100:0 to 90:10) to obtain compound 6-10.

Characterization of Compound 6-10

LCMS: m/z (ESI)=375.0 $[M+Na]^{30}$ .

$^1$H NMR (400 MHz, $CDCl_3$) δ: 1.38-1.43 (m, 3 H), 1.54-1.57 (m, 6 H), 2.07-2.10 (m, 2 H), 2.47-2.62 (m, 2 H), 3.23-3.30 (m, 2 H), 3.59-3.62 (m, 6 H), 4.34-4.37 (m, 2 H), 4.66-4.70 (m, 1 H).

Step 9: Synthesis of Compound 6-11

Compound 6-10 (283 mg, 802.96 μmol, 1 eq) was dissolved in ethanol (10 mL), p-toluenesulfonic acid monohydrate (158.48 mg, 833.15 μmol, 1.04 eq) was added thereto, and the mixture was stirred at 20° C. for 1 hour. The solvent of the reaction mixture was concentrated to dryness under reduced pressure to obtain the crude product, which was purified by silica gel column chromatography (gradient elution: petroleum ether/ethyl acetate=100:0 to 80:20) to obtain compound 6-11.

Characterization of Compound 6-11

LCMS: m/z (ESI)=268.9 $[M+H]^+$.

$^1$H NMR (400 MHz, $CDCl_3$) δ: 1.38-1.41 (m, 3 H), 1.80 (s, 1 H), 2.01-2.17 (m, 2 H), 2.49-2.63 (m, 2 H), 3.24 -3.30 (m, 2 H), 3.51 -3.56 (m, 2 H), 3.95 -4.06 (m, 2 H), 4.34 -4.38 (m, 2 H).

Step 10: Synthesis of Compound 6-12

Compound 6-11 (50 mg, 186.34 μmol, 1 eq) was dissolved in anhydrous tetrahydrofuran (7.5 mL), and then tert-butoxy bis(dimethylamino)methane (162.38 mg, 931.70 μmol, 192.39 μL, 5 eq) was added thereto, and the mixture was stirred at 80° C. for 12 hours. The solvent was concentrated to dryness under reduced pressure to obtain compound 6-12.

Characterization of Compound 6-12

LCMS: m/z (ESI)=297.0 $[M-26]^+$.

Step 11: Synthesis of Compound 6-13

Compound 6-12 (60 mg, 185.53 μmol, 1 eq) was dissolved in N,N-dimethylformamide (1.2 mL), then compound 1-3 (58.87 mg, 185.53 μmol, 1 eq) was added, and the mixture was stirred at 110° C. for 12 hours. Ethyl acetate (10 mL), water (5 mL) and saturated brine (5 mL) were added to the reaction mixture, and the phases were separated. The organic phase was dried over anhydrous sodium sulfate, filtered, and the solvent was concentrated to dryness under reduced pressure, and the crude product was purified by silica gel column chromatography (gradient elution: dichloromethane:methanol=100:0 to 90:10) to obtain compound 6-13.

Characterization of Compound 6-13

LCMS: m/z (ESI)=578.1 $[M+H]^+$.

Step 12: Synthesis of Compound 6

Compound 6-13 (8 mg, 13.85 μmol, 1 eq) was dissolved in tetrahydrofuran (0.8 mL), and then ammonium chloride (30 mg, 560.84 μmol, 40.49 eq) and a solution of lithium bis(trimethylsilyl)amide in tetrahydrofuran at a concentration of 1 M (567.85 μL, 41 eq) were added thereto, and the mixture was stirred at 20° C. for 1 hour. After the reaction was quenched by adding methanol (5 mL) to the reaction mixture, the solvent was concentrated to dryness under reduced pressure, and the crude product was purified by HPLC preparative chromatography (HPLC preparation method: Waters Xbridge BEH preparative chromatograph; chromatographic column: Prep sunfire C18 100*30 mm*10 μm; mobile phase A: 10 mM ammonium bicarbonate aqueous solution, mobile phase B: acetonitrile; running gradient: B %: 35% to 50%, run for 8 min) to obtain compound 6.

Characterization of Compound 6

LCMS: m/z (ESI)=549.3 $[M+H]^+$.

1H NMR (400 MHz, DMSO-$d_6$) δ: 2.18-2.26 (m, 3 H), 2.29-2.38 (m, 4 H), 2.40 -2.46 (m, 4 H), 2.68-2.81 (m, 4 H), 3.02-3.17 (m, 4 H), 4.55-4.70 (m, 1 H), 6.66-6.87 (m, 1 H), 7.11-7.27 (m, 2 H), 7.32-7.51 (m, 2 H), 8.27-8.37 (m, 1 H), 8.62-8.74 (m, 1 H).

Example 7

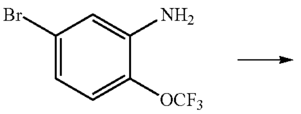

7-1

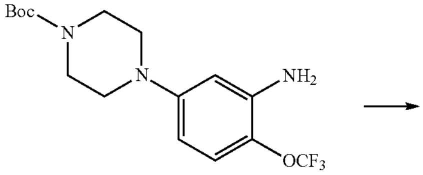

7-2

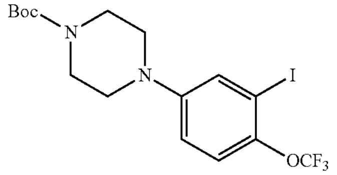

7-3

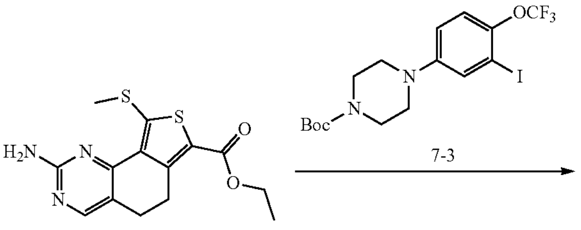

5-4

-continued

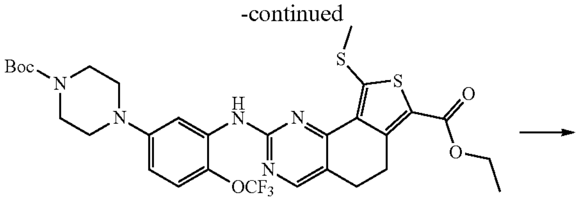

7-4

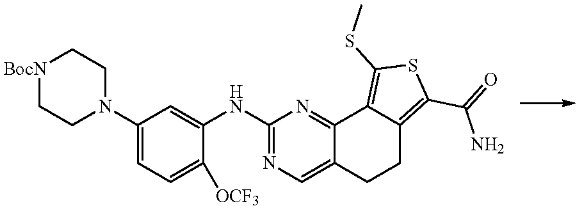

7-5

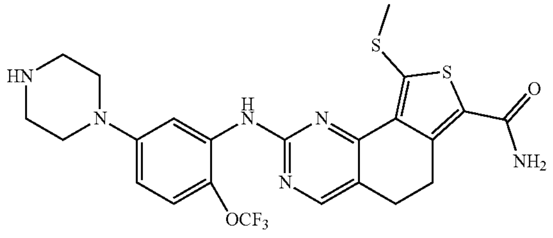

7

Step 1: Synthesis of Compound 7-2

Compound 7-1 (4 g, 15.62 mmol, 1 eq) was dissolved in tetrahydrofuran (40 mL), and 2-dicyclohexylphosphine-2-(N,N-dimethylamine)-biphenyl (491.90 mg, 1.25 mmol, 0.08 eq), tris(dibenzylideneacetone)dipalladium (1.14 g, 1.25 mmol, 0.08 eq) were added thereto, and a solution of lithium bis(trimethylsilyl)amide in tetrahydrofuran at a concentration of 1 M (37.50 mL, 2.4 eq) and 1-Boc-piperazine (4.36 g, 23.44 mmol, 1.5 eq) were added thereto under nitrogen atmosphere, and the resulting reaction mixture was stirred at 80° C. under nitrogen atmosphere for 3 hours. The reaction system was quenched by adding water (60 mL), extracted with dichloromethane (50 mL*3), and the phases were separated, and the organic phases were combined and dried over anhydrous sodium sulfate, filtered, and the filtrate was concentrated to dryness under reduced pressure to obtain the crude product. The crude product was purified by silica gel column chromatography (gradient elution: dichloromethane: methanol=100:0 to 98:2) to obtain compound 7-2.

Characterization of Compound 7-2

LCMS: m/z (ESI)=362.10 $[M+H]^+$.

$^1$H NMR (400 MHz, $CDCl_3$) δ: 7.00-7.06 (m, 1 H), 6.26-6.35 (m, 2 H), 3.78-3.86 (m, 2 H), 3.53-3.58 (m, 4 H), 3.02-3.14 (m, 4 H), 1.49 (s, 9 H).

Step 2: Synthesis of Compound 7-3

Compound 7-2 (2 g, 5.53 mmol, 1 eq) was dissolved in dimethyl sulfoxide (60 mL) solution, sodium nitrite (1.53 g, 22.14 mmol, 4 eq) was added thereto, and 45% hydroiodic acid aqueous solution (3.78 g, 13.28 mmol, 2.22 mL, 2.4 eq) was added dropwise thereto at 20° C., then the reaction temperature was raised to 35° C. and the reaction mixture was stirred for 16 hours. Water (60 mL) was added to the reaction system to dilute the reaction, then ethyl acetate (50 mL*3) was added for extraction, and the phases were separated, and the organic phases were combined, dried over anhydrous sodium sulfate, filtered, and concentrated under reduced pressure to obtain the crude product. The crude product was purified by silica gel column chromatography (gradient elution: petroleum ether/ethyl acetate=100:0 to 80:20) to obtain compound 7-3.

Characterization of Compound 7-3

LCMS: m/z (ESI)=473.00 $[M+H]^+$.

$^1$H NMR (400 MHz, $CDCl_3$) δ: 7.32-7.34 (m, 1 H), 7.11-7.16 (m, 1 H), 6.85-6.91 (m, 1 H), 3.55-3.61 (m, 4 H), 3.09-3.16 (m, 4 H), 1.49 (s, 9 H).

Step 3: Synthesis of Compound 7-4

Compound 5-4 (180.36 mg, 561.16 μmol, 1 eq) was dissolved in 1,4-dioxane (8 mL) solution, and tris(dibenzylideneacetone)dipalladium (51.39 mg, 56.12 μmol, 0.1 eq), 4,5-bis(diphenylphosphino)-9,9-dimethylxanthene (32.47 mg, 56.12 μmol, 0.1 eq) and cesium carbonate (365.67 mg, 1.12 mmol, 2 eq) were added thereto under nitrogen atmosphere. After the system was replaced with nitrogen three times, compound 7-3 (265 mg, 561.16 μmol, 1 eq) was added thereto, and the resulting reaction mixture was stirred at 100° C. for 5 hours. Water (20 mL) was added to the reaction system to quench the reaction, then ethyl acetate (20 mL*3) was added for extraction, and the phases were separated, and the organic phases were combined, dried over anhydrous sodium sulfate, filtered, and the filtrate was concentrated under reduced pressure to obtain the crude product. The crude product was purified by silica gel column chromatography (gradient elution: petroleum ether/ethyl acetate=100:0 to 80:20) to obtain compound 7-4.

Characterization of Compound 7-4

LCMS: m/z (ESI)=666.20 $[M+H]^+$.

$^1$H NMR (400 MHz, $CDCl_3$) δ: 8.31 (s, 1 H), 8.27-8.30 (m, 1 H), 7.09-7.19 (m, 1 H), 6.48-6.56 (m, 1 H), 5.28-5.35 (m, 1 H), 4.32-4.42 (m, 2 H), 3.53-3.63 (m, 4 H), 3.28 -3.37 (m, 2 H), 3.12-3.24 (m, 4 H), 2.83 (t, J=7.2 Hz, 2 H), 2.66 (s, 3 H), 1.49 (s, 9 H), 1.38 -1.43 (m, 3 H).

Step 4: Synthesis of Compound 7-5

Compound 7-4 (300 mg, 450.62 μmol, 1 eq) was dissolved in anhydrous tetrahydrofuran (10 mL), then ammonium chloride (144.63 mg, 2.70 mmol, 6 eq) was added thereto, and the reaction temperature was lowered to 0° C. under nitrogen atmosphere and a solution of lithium bis (trimethylsilyl)amide in tetrahydrofuran at a concentration of 1 M (9.01 mL, 20 eq) was added, and the resulting reaction mixture was stirred at 20° C. for 3 hours. Water (15 mL) was added to the reaction system to quench the reaction, and the reaction mixture was extracted with ethyl acetate (20 mL*3), then the phases were separated, and the organic phases were combined and concentrated to dryness under reduced pressure. The crude product was separated by thin-layer chromatography (developing agent: dichloromethane/methanol=10:1) to obtain compound 7-5.

Characterization of Compound 7-5

LCMS: m/z (ESI)=637.20 $[M+H]^+$.

$^1H$ NMR (400 MHz, $CDCl_3$) δ: 8.25-8.31 (m, 1 H), 8.14-8.24 (m, 1 H), 7.13-7.21 (m, 1 H), 6.52-6.63 (m, 1 H), 5.50-5.59 (m, 2 H), 3.54-3.65 (m, 4 H), 3.25-3.33 (m, 2 H), 3.13-3.25 (m, 4 H), 2.81-2.90 (m, 2 H), 2.64 (s, 3 H), 1.49 (s, 9 H).

Step 5: Synthesis of Compound 7

Compound 7-5 (100 mg, 157.06 μmol, 1 eq) was dissolved in dichloromethane (5 mL) solution, and trifluoroacetic acid (3.85 g, 33.77 mmol, 2.50 mL, 214.99 eq) was added thereto, and the mixture was stirred at 20° C. for 2 hours. After the reaction system was directly concentrated to dryness under reduced pressure, the crude product was purified by HPLC preparative chromatography (HPLC preparation method: Waters Xbridge Prep OBD preparative chromatograph; chromatographic column: C18 150*40 mm*10 μm; mobile phase A: 10 mM ammonium bicarbonate aqueous solution (0.05% ammonia water), mobile phase B: acetonitrile; running gradient: B %: 20% to 50%, run for 8 min) to obtain compound 7.

Characterization of Compound 7

LCMS: m/z (ESI)=537.10 $[M+H]^+$.

$^1H$ NMR (400 MHz, DMSO-$d_6$) δ: 8.46 (s, 1 H), 8.32 (s, 1 H), 7.47-7.51 (m, 1 H), 7.41-7.46 (m, 2 H), 7.13-7.20 (m, 1 H), 6.66-6.71 (m, 1 H), 3.08-3.15 (m, 2 H), 2.95 -3.05 (m, 4 H), 2.79-2.84 (m, 4 H), 2.71-2.76 (m, 2 H), 2.54 (s, 3 H).

Example 8

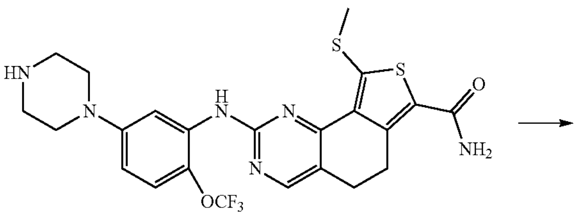

7

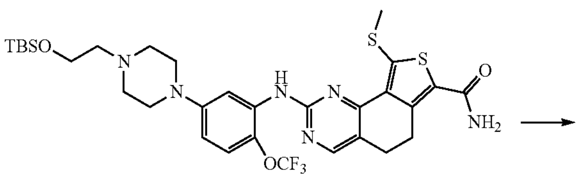

8-1

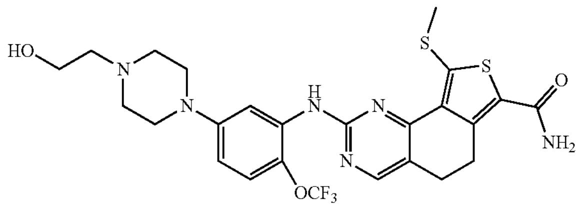

8

Step 1: Synthesis of Compound 8-1

Compound 7 (80 mg, 149.09 μmol, 1 eq) was dissolved in a mixture of anhydrous tetrahydrofuran (5 mL) and dimethyl sulfoxide (2.5 mL), and triethylamine (15.09 mg, 149.09 μmol, 20.75 μL, 1 eq) was added to adjust the pH of the mixture to 7 to 8, then the pH was adjusted to 5 to 6 with acetic acid (35.81 mg, 596.36 μmol, 34.11 μL, 4 eq), and (tert-butyldimethylsilyloxy)acetaldehyde (64.97 mg, 372.72 μmol, 71.01 μL, 2.5 eq) was added thereto at 0° C. and the mixture was stirred for 0.5 hours, then sodium triacetoxyborohydride (69.52 mg, 328.00 μmol, 2.2 eq) was added thereto at 0° C., and the resulting reaction mixture was stirred at 20° C. for 2 hours. Water (3 mL) was added to the reaction system, and the reaction mixture was extracted with ethyl acetate (5 mL*3), then the phases were separated, and the organic phases were combined, dried over anhydrous sodium sulfate, filtered, and concentrated under reduced pressure to obtain the crude product. The crude product was purified by thin-layer chromatography (developing agent: dichloromethane/methanol=10:1) to obtain compound 8-1.

Characterization of Compound 8-1

LCMS: m/z (ESI)=695.20 $[M+H]^+$.

$^1H$ NMR (400 MHz, $CDCl_3$) δ: 8.31 (s, 1 H), 8.20-8.27 (m, 1 H), 7.32-7.38 (m, 1 H), 7.12-7.20 (m, 1 H), 6.47-6.56 (m, 1 H), 5.65-5.75 (m, 2 H), 3.86-4.01 (m, 2 H), 3.37-3.44 (m, 2 H), 3.21-3.35 (m, 4 H), 2.81-2.99 (m, 6 H), 2.66 (s, 3 H), 1.24-1.29 (m, 2 H), 0.90 (s, 9 H), 0.09 (s, 6 H).

Step 2: Synthesis of Compound 8

Compound 8-1 (100 mg, 143.90 μmol, 1 eq) was dissolved in anhydrous tetrahydrofuran (0.5 mL) solution, and 1 M tetrabutylammonium fluoride tetrahydrofuran solution (287.81 μL, 2 eq) was added, and the mixture was stirred at 20° C. for 16 hours. Water (20 mL) was added to the reaction system for washing, and the reaction mixture was extracted with ethyl acetate (25 mL*3), then the phases were separated, and the organic phases were combined, dried over anhydrous sodium sulfate, filtered, and concentrated under reduced pressure to obtain the crude product, which was purified by high performance liquid phase preparative chromatography (HPLC preparation method: Waters Xbridge Prep OBD preparative chromatograph; chromatographic column: C18 150*40 mm*10 μm; mobile phase A: 10 mM ammonium bicarbonate aqueous solution (containing 0.05% ammonia water), mobile phase B: acetonitrile; running gradient: B %: 20% to 50%, run for 8 min) to obtain compound 8.

Characterization of Compound 8

LCMS: m/z (ESI)=581.20 $[M+H]^+$.

$^1H$ NMR (400 MHz, DMSO-$d_6$) δ: 8.44-8.48 (m, 1 H), 8.31 (s, 1 H), 7.49-7.52 (m, 1 H), 7.40-7.46 (m, 2 H), 7.13-7.19 (m, 1 H), 6.68-6.72 (m, 1 H), 4.39-4.45 (m, 1 H), 3.49-3.56 (m, 2 H), 3.29 (s, 3 H), 3.09-3.17 (m, 6 H), 2.71-2.77 (m, 2 H), 2.52 -2.60 (m, 4 H), 2.40-2.46 (m, 2 H).

Example 9

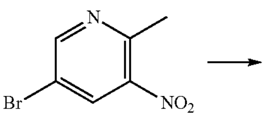

9-1

-continued

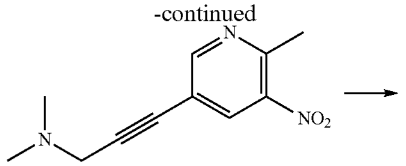

9-2

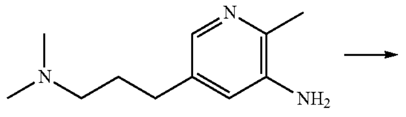

9-3

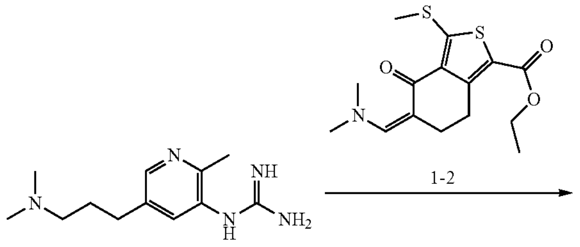

9-4

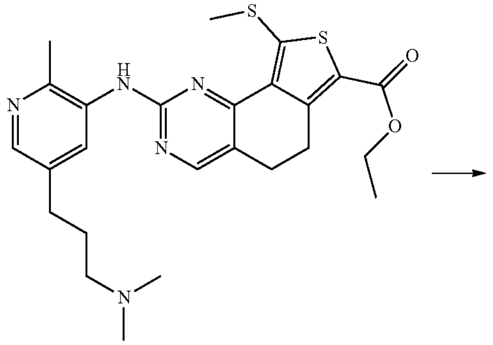

9-5

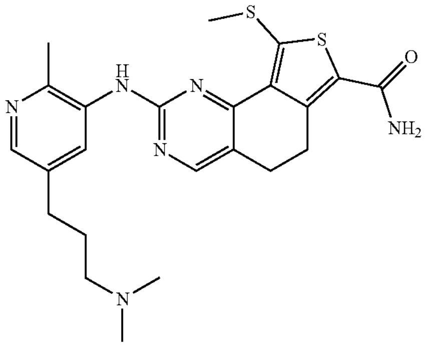

9

Step 1: Synthesis of Compound 9-2

Compound 9-1 (2.4 g, 11.06 mmol, 1 eq), dichlorobis (triphenylphosphine)palladium (II) (194.06 mg, 276.47 μmol, 0.025 eq), cuprous iodide (105.31 mg, 552.94 μmol, 0.05 eq) were added to a reaction flask, then diethylamine (25 mL) and 1-dimethylamino-2-propyne (1.15 g, 13.82 mmol, 1.47 mL, 1.25 eq) were added thereto, and the reaction mixture was stirred at 60° C. under nitrogen atmosphere for 3 hours. After the reaction was completed, the temperature was lowered to 20° C., and the reaction mixture was concentrated to dryness under reduced pressure. The crude product was purified by silica gel column chromatography (gradient elution: petroleum ether: ethyl acetate=100:0 to 0:100) to obtain compound 9-2.

Characterization of Compound 9-2

LCMS: m/z (ESI)=220.0 $[M+H]^+$.

$^1H$ NMR (400 MHz, $CDCl_3$) δ: 2.38 (s, 6 H), 2.84 (s, 3 H), 3.51 (s, 2 H), 8.24 -8.26 (m, 1 H), 8.69 -8.75 (m, 1 H).

Step 2: Synthesis of Compound 9-3

Raney nickel (1.4 g, 16.34 mmol, 2.56 eq), ethanol (50 mL) and compound 9-2 (1.4 g, 6.39 mmol, 1 eq) were added under a micron argon flow, and the reaction mixture was stirred at 25° C. for 4 hours under hydrogen (15 psi) conditions. The reaction mixture was filtered and the solvent was concentrated to dryness under reduced pressure. The crude product was purified by silica gel column chromatography (gradient elution: dichloromethane/methanol=100:0 to 95:5) to obtain compound 9-3.

Characterization of Compound 9-3

LCMS: m/z (ESI)=194.1 $[M+H]^+$.

Step 3: Synthesis of Compound 9-4

Compound 9-3 was dissolved in 6 M hydrochloric acid aqueous solution (517.36 μL 6 eq), then aminonitrile (174.00 mg, 4.14 mmol, 174.00 8 eq) was added thereto, and the mixture was stirred at 60° C. for 1 hour. Water (5 mL) and dichloromethane (5 mL) were added to the reaction mixture, and the phases were separated, and solid sodium hydroxide was added to the aqueous phase to adjust the pH of the aqueous phase to greater than 12, and the solvent was concentrated to dryness under reduced pressure to obtain the crude product. The crude product was purified by HPLC preparative chromatography (HPLC preparation method: Waters Xbridge Prep OBD preparative chromatograph; chromatographic column: C18 150*40 mm*10 μm; mobile phase A: 10 mM ammonium bicarbonate aqueous solution (containing 0.05% ammonia), mobile phase B: acetonitrile; running gradient: B %: 1% to 15%, run for 8 min) to obtain compound 9-4.

Characterization of Compound 9-4

LCMS: m/z (ESI)=236.3 $[M+H]^+$.

$^1H$ NMR (400 MHz, DMSO-$d_6$) δ: 1.56-1.63 (m, 2 H), 2.08 (s, 6 H), 2.10 -2.18 (m, 5 H), 2.40 -2.47 (m, 2 H), 5.08 (s, 4 H), 6.77 (s, 1 H), 7.82 (s, 1 H).

Step 4: Synthesis of Compound 9-5

Compound 9-4 (40 mg, 169.98 μmol, 1 eq) was dissolved in N,N-dimethylformamide (1 mL), then compound 1-2 (76.09 mg, 169.98 μmol, 1 eq) was added thereto, and the mixture was stirred at 110° C. for 12 hours. Ethyl acetate (10 mL), saturated brine (5 mL) and water (5 mL) were added to the reaction mixture, and the phases were separated, and the organic phases were combined, dried over anhydrous sodium sulfate, and filtered, and the solvent was concentrated to dryness under reduced pressure to obtain the crude product. The crude product was purified by HPLC preparative chromatography (HPLC preparation method: Waters Xbridge BEH preparative chromatograph; chromatographic column: C18 100*30 mm*10 μm; mobile phase A: 0.04% hydrochloric acid aqueous solution, mobile phase B: acetonitrile; running gradient: B %: 30% to 50%, run for 8 min) to obtain compound 9-5.

Characterization of Compound 9-5

LCMS: m/z (ESI)=498.2 $[M+H]^+$.

$^1H$ NMR (400 MHz, DMSO-$d_6$) δ: 1.09-1.23 (m, 3 H), 1.92-2.07 (m, 2 H), 2.33 -2.36 (m, 3 H), 2.54-2.57 (m, 3 H), 2.59-2.67 (m, 2 H), 2.68-2.72 (m, 6 H), 2.73-2.81 (m, 2 H), 2.95-3.02 (m, 2 H), 3.04-3.13 (m, 2 H), 4.02-4.17 (m, 2 H), 8.01-8.14 (m, 1 H), 8.24 -8.36 (m, 1 H), 8.43-8.55 (m, 1 H).

Step 5: Synthesis of Compound 9

Compound 9-5 (24 mg, 48.22 μmol, 1 eq) was dissolved in a solution (964.49 μL, 20 eq) of lithium bis(trimethylsilyl) amide in tetrahydrofuran at a concentration of 1 M, and then ammonium chloride (25.80 mg, 482.24 μmol, 10 eq) was added thereto, the mixture was stirred at 20° C. under nitrogen atmosphere for 16 hours. After methanol (5 mL) was added to quench the reaction, the solvent was concentrated to dryness under reduced pressure to obtain the crude product. The crude product was purified by HPLC preparative chromatography (HPLC preparation method: Waters Xbridge BEH preparative chromatograph; chromatographic column: C18 100*30 mm*10 μm; mobile phase A: 0.1% ammonium bicarbonate aqueous solution, mobile phase B: acetonitrile; running gradient: B %: 15% to 45%, run for 8 min) to obtain compound 9.

Characterization of Compound 9

LCMS: m/z (ESI)=469.1 $[M+H]^+$.

$^1H$ NMR (400 MHz, $CDCl_3$) δ: 1.76-1.84 (m, 2 H), 2.24 (s, 6 H), 2.33-2.37 (m, 2 H), 2.49 (s, 3 H), 2.55 (s, 3 H), 2.58 -2.63 (m, 2 H), 2.70-2.80 (m, 2 H), 3.15 -3.23 (m, 2 H), 5.49 (s, 2 H), 6.72 (s, 1 H), 8.00 (s, 1 H), 8.20 (s, 1 H), 8.29 (s, 1 H).

Example 10

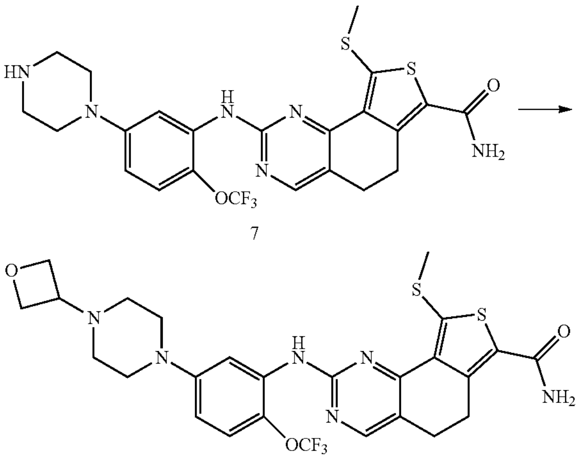

7

10

Step 1: Synthesis of Compound 10

After compound 7 (10 mg, 18.64 μmol, 1 eq) was dissolved in dichloroethane (0.5 mL), 3-oxetanone (1.48 mg, 20.50 μmol, 1.1 eq) was added thereto, and then tetraethoxytitanium (4.25 mg, 18.64 μmol, 3.86 μL, 1 eq) were added thereto, and the resulting reaction mixture was stirred at 20° C. for 1 hour, then sodium triacetoxyborohydride (4.34 mg, 20.50 μmol, 1.1 eq) was added thereto, and the mixture was stirred at 20° C. for 12 hours. Water (5 mL) was added to the reaction system, and a large amount of white flocs precipitated, then ethyl acetate (5 mL*5) was added for extraction, and the phases were separated, and the organic phases were combined and dried over anhydrous sodium sulfate, filtered, and concentrated to dryness under reduced pressure to obtain the crude product. The crude product was purified by HPLC preparative chromatography (HPLC preparation method: Waters Xbridge BEH preparative chromatograph; chromatographic column: Prep sunfire C18 100*30 mm*10 μm; mobile phase A: 0.1% ammonium bicarbonate aqueous solution, mobile phase B: acetonitrile; running gradient: B %: 35% to 50%, run for 8 min) to obtain compound 10.

Characterization of Compound 10

LCMS: m/z (ESI)=593.20 $[M+H]^+$.

$^1H$ NMR (400 MHz, $CD_3OD$) δ: 8.29 (s, 1 H), 7.95-7.99 (m, 1 H), 7.16-7.21 (m, 1 H), 6.66-6.72 (m, 1 H), 4.70-4.75 (m, 2 H), 4.62-4.66 (m, 2 H), 3.53-3.59 (m, 1 H), 3.27-3.30 (m, 4 H), 3.21 (t, J=7.20 Hz, 2 H), 2.80-2.85 (m, 2 H), 2.60-2.65 (m, 3 H), 2.49-2.55 (m, 4 H).

Example 11

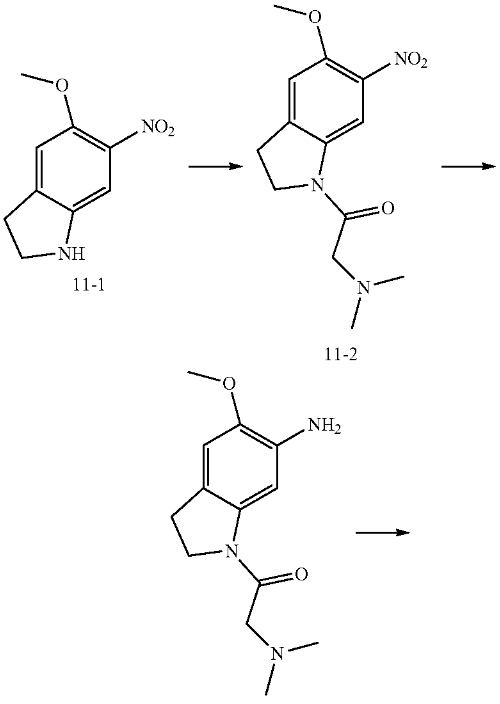

11-1

11-2

11-3

-continued

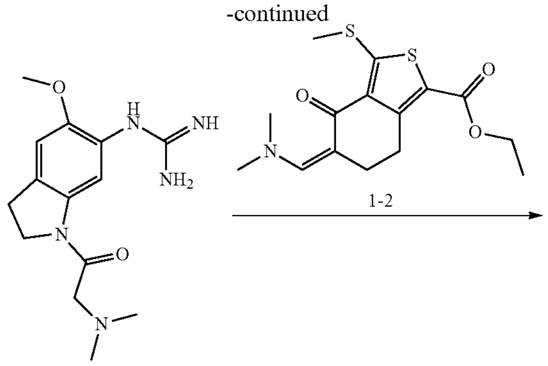

11-4

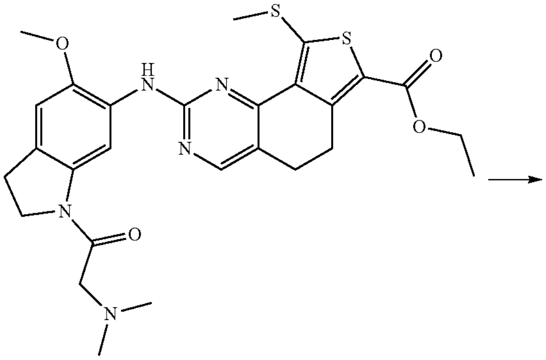

11-5

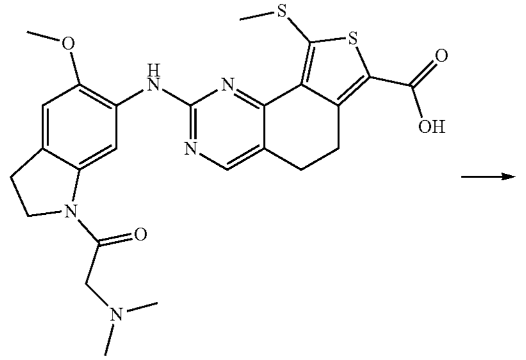

11-6

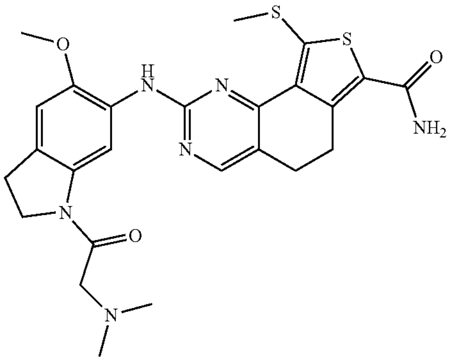

11

Step 1: Synthesis of Compound 11-2

Compound 11-1 (2 g, 10.30 mmol, 1 eq) and potassium carbonate (2.85 g, 20.60 mmol, 2 eq) were dissolved in tetrahydrofuran (20 mL), and the reaction mixture was cooled to 0° C. under nitrogen atmosphere, and then bromoacetyl bromide (3.12 g, 15.45 mmol, 1.34 mL, 1.5 eq) was added thereto, and the mixture was stirred at 0° C. for 10 minutes, then 40% aqueous dimethylamine (3.48 g, 30.90 mmol, 3.91 mL, 3 eq) was added thereto at 0° C., and the mixture was stirred at 0° C. for 10 minutes. The reaction mixture was slowly poured into ice water (200 mL) to quench the reaction, and extracted with ethyl acetate (100 mL*3), and the phases were separated, and the organic phases were combined, washed with saturated brine (100 mL*3), dried over anhydrous sodium sulfate and filtered, and the filtrate was concentrated under reduced pressure to obtain the crude product. The crude product was purified by silica gel column chromatography (gradient elution: dichloromethane/methanol=100:0 to 95:5) to obtain compound 11-2.

Characterization of Compound 11-2

$^1$H NMR (400 MHz, $CDCl_3$) δ: 8.67 (s, 1 H), 6.92 (s, 1 H), 4.26 (t, J=8.60 Hz, 2 H), 3.92 (s, 3 H), 3.16-3.32 (m, 4 H), 2.41 (s, 6 H).

Step 2: Synthesis of Compound 11-3

10% wet palladium carbon (1 g) was added under micron argon flow, then anhydrous methanol (2 mL) and compound 11-2 (1 g, 3.58 mmol, 1 eq) were added sequentially, and the reaction mixture was stirred at 40° C. for 12 hours under hydrogen (15 psi) condition. The reaction mixture was filtered through a funnel covered with diatomite, the filter cake was rinsed with methanol (50 mL*2), the filtrate was collected, and the filtrate was concentrated under reduced pressure to obtain the crude product. The crude product was purified by silica gel column chromatography (gradient elution: petroleum ether/ethyl acetate+0.5% ammonia water=100:0 to 0:100) to obtain compound 11-3.

Characterization of Compound 11-3

$^1$H NMR (400 MHz, DMSO-$d_6$) δ: 7.55 (s, 1 H), 6.70 (s, 1 H), 4.63 (s, 2 H), 3.95 -4.19 (m, 2 H), 3.65-3.71 (m, 3 H), 3.13 (s, 2 H), 2.87-3.04 (m, 2 H), 2.25 (s, 6 H).

Step 3: Synthesis of Compound 11-4

Compound 11-3 (200 mg, 802.22 μmol, 1 eq) was dissolved in 6 M hydrochloric acid aqueous solution (802.22 μL, 6 eq), then aminonitrile (269.80 mg, 6.42 mmol, 269.80 μL, 8 eq) was added thereto, and the temperature was raised to 100° C. and the mixture was stirred for 2 hours, then aminonitrile (134.90 mg, 3.21 mmol, 134.90 μL, 4 eq) was additionally added, and the reaction mixture was stirred at 100° C. for 12 hours. Water (10 mL) and dichloromethane (10 mL) were added to the reaction mixture for extraction. The phases were separated, and the aqueous phase was collected, and the pH of the aqueous phase was adjusted to 11 with saturated sodium hydroxide aqueous solution, and the aqueous phase was concentrated under reduced pressure to obtain the crude product. The crude product was purified by HPLC preparative chromatography (HPLC preparation method: Waters 2767/QDa preparative chromatograph; chromatographic column: Waters Xbridge BEH C18 100*25mm*5 μm; mobile phase A: 0.1% ammonium bicarbonate aqueous solution, mobile phase B: acetonitrile; running gradient: B %: 1% to 25%, run for 10 min) to obtain compound 11-4.

Characterization of Compound 11-4

$^1$H NMR (400 MHz, DMSO-$d_6$) δ: 7.61 (s, 1 H), 6.84 (s, 1 H), 5.50 (s, 3 H), 4.12 (t, J=8.40 Hz, 2 H), 3.67 (s, 3 H), 3.14 (s, 2 H), 3.05 (t, J=8.40 Hz, 2 H), 2.25 (s, 6 H).

Step 4: Synthesis of Compound 11-5

Compound 1-2 (67.02 mg, 205.94 μmol, 1 eq) was dissolved in N,N-dimethylformamide (2 mL), and compound 11-4 (60 mg, 205.94 μmol, 1 eq) was added thereto, and the mixture was stirred at 110° C. for 16 hours. The reaction mixture was poured into water (30 mL) to quench the reaction, then extracted with ethyl acetate (15 mL*3), and the phases were separated, and the organic phases were combined, washed with saturated brine (15 mL*3), dried over anhydrous sodium sulfate, filtered, and concentrated under reduced pressure to obtain the crude product. The crude product was purified by thin-layer chromatography (developing agent: dichloromethane/methanol=10:1) to obtain compound 11-5.

Characterization of Compound 11-5

$^1$H NMR (400 MHz, $CDCl_3$) δ: 9.25 (s, 1 H), 8.32 (s, 1 H), 6.76 (s, 1 H), 4.35 (q, J=7.20 Hz, 2 H), 4.18 (t, J=8.20 Hz, 2 H), 3.82-3.95 (m, 3 H), 3.60 (s, 1 H), 3.25-3.36 (m, 2 H), 3.16-3.25 (m, 2 H), 3.09-3.16 (m, 1 H), 2.98-3.09 (m, 1 H), 2.73-2.89 (m, 2 H), 2.65 (s, 3 H), 2.39 (s, 6 H), 1.40 (t, J=7.20 Hz, 3 H).

Step 5: Synthesis of Compound 11-6

Compound 11-5 (50 mg, 90.30 μmol, 1 eq) was dissolved in anhydrous tetrahydrofuran (4 mL) and anhydrous ethanol (1 mL), and lithium hydroxide monohydrate (18.95 mg, 451.51 μmol, 5 eq) was dissolved in water (1 mL) and then added to the reaction mixture, and the mixture was stirred at 40° C. for 5 hours. The pH of the reaction mixture was adjusted to 7 with 1 M dilute hydrochloric acid, and then the reaction mixture was freeze-dried to obtain compound 11-6.

Characterization of Compound 11-6

$^1$H NMR (400 MHz, DMSO-$d_6$) δ: 10.35 (s, 1 H), 8.82 (s, 1 H), 8.54 (s, 1 H), 8.34 (s, 1 H), 7.07 (s, 1 H), 4.45 (d, J=4.40 Hz, 2 H), 4.10 (t, J=8.20 Hz, 2 H), 3.80 (s, 3 H), 3.17-3.24 (m, 4 H), 2.88 (d, J=4.40 Hz, 6 H), 2.79 (t, J=7.00 Hz, 2 H), 2.56 (s, 3 H).

Step 6: Synthesis of Compound 11

Compound 11-6 (110 mg, 209.27 μmol, 1 eq) was dissolved in N,N-dimethylformamide (2 mL), and then N,N-diisopropylethylamine (81.14 mg, 627.80 μmol, 109.35 μL, 3 eq), 0-(7-azabenzotriazol-1-yl)-N,N,N,N-tetramethyluronium hexafluorophosphate (103.44 mg, 272.05 μmol, 1.3 eq), ammonium bicarbonate (49.63 mg, 627.80 μmol, 51.70 μL, 3 eq) were added thereto sequentially, and the mixture was stirred at 20° C. for 2 hours under nitrogen atmosphere. The reaction mixture was directly filtered, and the filtrate was collected, purified by HPLC preparative chromatography (HPLC preparation method: Waters 2767/QDa preparative chromatograph; chromatographic column: Phenomenex C18 80*40 mm*3 μm; mobile phase A: 0.1% ammonium bicarbonate aqueous solution, mobile phase B: acetonitrile; running gradient: B %: 30% to 60%, run for 8 min) to obtain compound 11.

Characterization of Compound 11

LCMS: m/z (ESI)=525.30 [M+H]$^+$.

$^1$H NMR (400 MHz, DMSO-$d_6$) δ: 8.67 (s, 1 H), 8.29 (s, 1 H), 7.84 (s, 1 H), 7.42 (s, 2 H), 6.96 (s, 1 H), 4.16 (t, J=8.20 Hz, 2 H), 3.79 (s, 3 H), 3.17 (s, 2 H), 3.11 (t, J=7.20 Hz, 4 H), 2.70-2.77 (m, 2 H), 2.53 (s, 3 H), 2.26 (s, 6 H).

Example 12

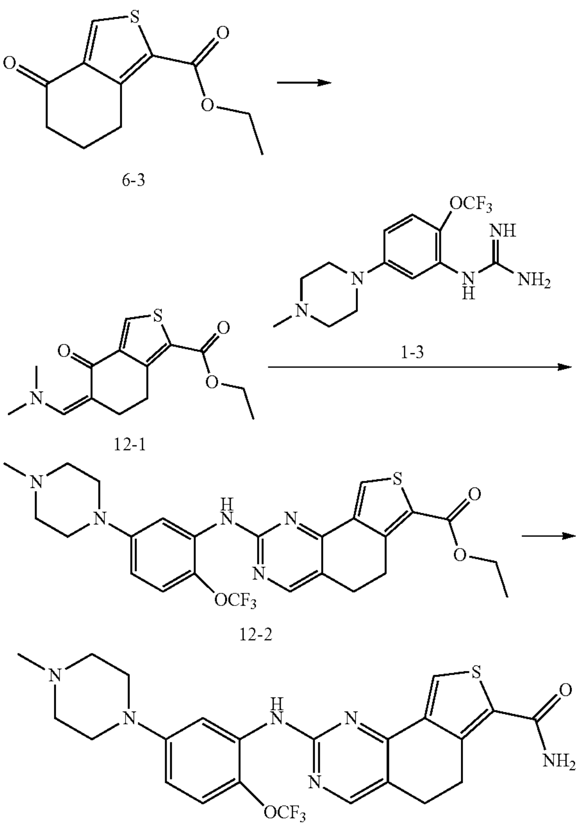

6-3

1-3

12-1

12-2

12

Step 1: Synthesis of Compound 12-1

Compound 6-3 (200 mg, 891.76 μmol, 1 eq) was dissolved in anhydrous tetrahydrofuran (4 mL), and then tert-butoxy bis(dimethylamino)methane (466.25 mg, 2.68 mmol, 552.43 μL, 3 eq) was added thereto, and the mixture was stirred at 80° C. for 2 hours under nitrogen atmosphere. The solvent was concentrated to dryness under reduced pressure to obtain compound 12-1.

Characterization of Compound 12-1

LCMS: m/z (ESI)=253.2 [M−26]$^+$.

Step 2: Synthesis of Compound 12-2

Compound 12-1 (100 mg, 357.97 μmol, 1 eq) was dissolved in N,N-dimethylformamide (2 mL), then compound 1-3 (113.59 mg, 357.97 μmol, 1 eq) was added thereto, and the mixture was stirred at 110° C. for 16 hours. Ethyl acetate (20 mL), water (10 mL) and saturated brine (10 mL) were added to the reaction mixture, then the phases were separated, and the organic phase was dried over anhydrous sodium sulfate and filtered, and the solvent was concentrated to dryness under reduced pressure to obtain the crude product. The crude product was purified by silica gel column chromatography (gradient elution: dichloromethane/methanol=100:0 to 98:2) to obtain compound 12-2.

Characterization of Compound 12-2

LCMS: m/z (ESI)=534.3 $[M+H]^+$.

$^1$H NMR (400 MHz, $CDCl_3$) δ: 1.42 (t, J=7.2 Hz, 3 H), 2.39 (s, 3 H), 2.62 (s, 4 H), 2.89 (t, J=7.2 Hz, 2 H), 3.26-3.43 (m, 6 H), 4.39 (q, J=7.2 Hz, 2 H), 6.50 -6.55 (m, 1 H), 7.15-7.20 (m, 1 H), 7.35 (s, 1 H), 8.25 (s, 1 H), 8.37 (s, 1 H), 8.40 -8.46 (m, 1 H).

Step 3: Synthesis of Compound 12

Compound 12-2 (135 mg, 253.02 μmol, 1 eq) was dissolved in a solution (2 mL, 7.90 eq) of lithium bis(trimethylsilyl)amide in tetrahydrofuran at a concentration of 1 M, and then ammonium chloride (54.14 mg, 1.01 mmol, 4 eq) was added thereto, and the mixture was stirred at 20° C. for 1 hour. The reaction mixture was directly concentrated to dryness under reduced pressure, then methanol (2 mL) was added thereto, and the solvent was continuously concentrated to dryness under reduced pressure to obtain the crude product. The crude product was purified by HPLC preparative chromatography (HPLC preparation method: Waters 2767/QDa preparative chromatograph; chromatographic column: Phenomenex C18 80*40 mm*3 μm; mobile phase A: 0.1% ammonium bicarbonate aqueous solution, mobile phase B: acetonitrile; running gradient: B %: 25% to 55%, run for 8 min) to obtain compound 12.

Characterization of Compound 12

LCMS: m/z (ESI)=505.1 $[M+H]^+$.

$^1$H NMR (400 MHz, $CDCl_3$) δ: 2.39 (s, 3 H), 2.57-2.69 (m, 4 H), 2.90 (t, J=7.15 Hz, 2 H), 3.26-3.38 (m, 6 H), 5.65 (d, J=5.77 Hz, 2 H), 6.55 (dd, J=9.03, 3.01 Hz, 1 H), 7.16 (dd, J=8.91, 1.51 Hz, 1 H), 7.36 (s, 1 H), 8.18 (s, 1 H), 8.37 (s, 1 H), 8.41 (d, J=2.89 Hz, 1 H).

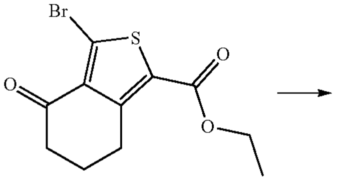

6-8

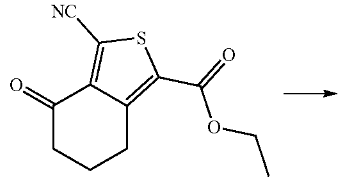

13-1

-continued

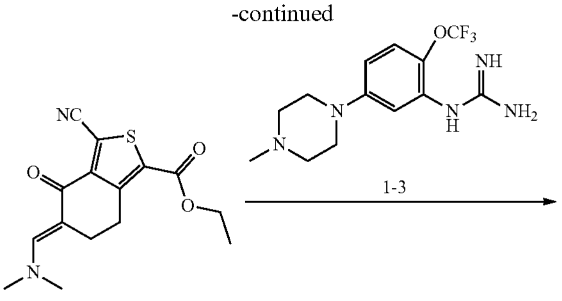

13-2

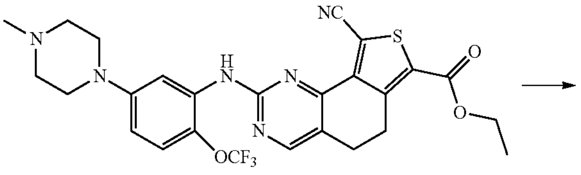

13-3

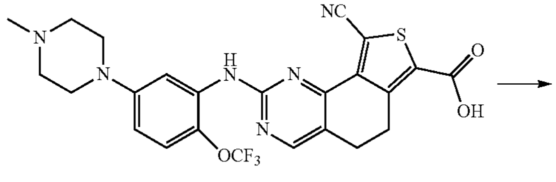

13-4

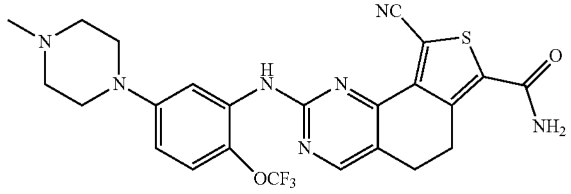

13

Example 13

Step 1: Synthesis of Compound 13-1

Compound 6-8 (300 mg, 989.54 μmol, 1 eq) was dissolved in N,N-dimethylformamide (4.5 mL), then cuprous cyanide (265.88 mg, 2.97 mmol, 648.49 μL, 3 eq) and potassium iodide (32.85 mg, 197.91 μmol, 0.2 eq) were added thereto, and the mixture was stirred at 140° C. for 0.5 hours under nitrogen atmosphere. Ethyl acetate (20 mL) and water (20 mL) were added to the reaction mixture, and then the reaction mixture was filtered. The phases of the filtrate were separated, and the organic phase was dried over anhydrous sodium sulfate, filtered, and the solvent was concentrated to dryness under reduced pressure to obtain the crude product. The crude product was purified by silica gel column chromatography (gradient elution: petroleum ether/ethyl acetate=100:0 to 90:10) to obtain compound 13-1.

Characterization of Compound 13-1

LCMS: m/z (ESI)=250.2 $[M+1]^+$.

$^1$H NMR (400 MHz, $CDCl_3$) δ: 1.41 (t, J=7.2 Hz, 3 H), 2.15 (t, J=6.8 Hz, 2 H), 2.59 -2.77 (m, 2 H), 3.27 (t, J=6.8 Hz, 2 H), 4.41 (q, J=7.2 Hz, 2 H).

Step 2: Synthesis of Compound 13-2

Compound 13-1 (145 mg, 581.66 μmol, 1 eq) was dissolved in anhydrous tetrahydrofuran (6 mL), and then tert-butoxy bis(dimethylamino)methane (304.12 mg, 1.74 mmol, 360.33 μL, 3 eq) was added thereto, and the mixture was stirred at 80° C. for 3 hours. The reaction mixture was directly concentrated to dryness under reduced pressure to obtain compound 13-2.

Characterization of Compound 13-2

LCMS: m/z (ESI)=305.2 $[M+H]^+$.

Step 3: Synthesis of Compound 13-3

Compound 13-2 (177 mg, 581.54 μmol, 1 eq) was dissolved in DMF (4.5 mL), then compound 1-3 (184.53 mg, 581.54 μmol, 1 eq) was added thereto, and the mixture was stirred at 110° C. for 16 hours. Ethyl acetate (20 mL), water (10 mL) and saturated brine (10 mL) were added to the reaction mixture, the phases were separated, and the organic phase was dried over anhydrous sodium sulfate and filtered, and the solvent was concentrated to dryness under reduced pressure to obtain the crude product. The crude product was purified by silica gel column chromatography (gradient elution: dichloromethane/methanol=100:0 to 90:10) to obtain compound 13-3.

Characterization of Compound 13-3

LCMS: m/z (ESI)=559.3 $[M+H]^+$.

$^1$H NMR (400 MHz, $CDCl_3$) δ: 1.43 (t, J=7.2 Hz, 3 H), 2.38 (s, 3 H), 2.62 (s, 4 H), 2.89 (t, J=7.2 Hz, 2 H), 3.17-3.44 (m, 6 H), 4.42 (q, J=6.8 Hz, 2 H), 6.51 -6.62 (m, 1 H), 7.10 -7.19 (m, 1 H), 7.39 (s, 1 H), 8.15 (d, J=2.8 Hz, 1 H), 8.46 (s, 1 H).

Step 4: Synthesis of Compound 13-4

Compound 13-3 (200 mg, 358.05 μmol, 1 eq) was dissolved in anhydrous tetrahydrofuran (5 mL), then lithium hydroxide monohydrate (45.07 mg, 1.07 mmol, 3 eq) and water (1 mL) were added thereto, and the mixture was stirred at 40° C. for 1 hour, then the reaction mixture was directly concentrated to dryness to obtain compound 13-4.

Characterization of Compound 13-4

LCMS: m/z (ESI)=531.1 $[M+1]^+$.

Step 5: Synthesis of Compound 13

Compound 13-4 (200 mg, 376.99 μmol, 1 eq) was dissolved in N,N-dimethylformamide (2 mL), and then N,N-diisopropylethylamine (146.17 mg, 1.13 mmol, 196.99 μL, 3 eq), 0-(7-azabenzotriazol-1-yl)-N,N,N,N-tetramethyluronium hexafluorophosphate (215.01 mg, 565.48 μmol, 1.5 eq), ammonium bicarbonate (89.41 mg, 1.13 mmol, 93.13 μL, 3 eq) were added thereto, and the mixture was stirred at 20° C. for 5 hours. Ethyl acetate (10 mL), water (5 mL) and saturated brine (5 mL) were added to the reaction mixture, the phases were separated, and the organic phase was dried over anhydrous sodium sulfate and filtered, and the solvent was concentrated to dryness under reduced pressure to obtain the crude product. The crude product was purified by HPLC preparative chromatography (HPLC preparation method: Waters 2767/QDa preparative chromatograph; chromatographic column: Phenomenex C18 75*30 mm*3 μm; mobile phase A: 0.1% ammonium bicarbonate aqueous solution, mobile phase B: acetonitrile; running gradient: B %: 25% to 55%, run for 8 min) to obtain compound 13.

Characterization of Compound 13

LCMS: m/z (ESI)=530.1 $[M+1]^+$.

$^1$H NMR (400 MHz, $CDCl_3$) δ: 2.35 (s, 3 H), 2.52-2.70 (m, 4 H), 2.85 -2.92 (m, 2 H), 3.12-3.43 (m, 6 H), 5.81 (s, 2 H), 6.49-6.61 (m, 1 H), 7.10-7.20 (m, 1 H), 7.46 (s, 1 H), 8.05-8.19 (m, 1 H). 8.47 (s, 1 H).

Example 14

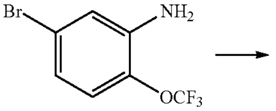

14-1

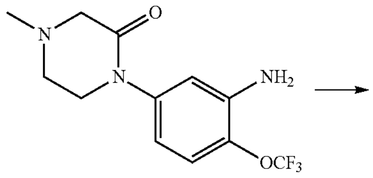

14-2

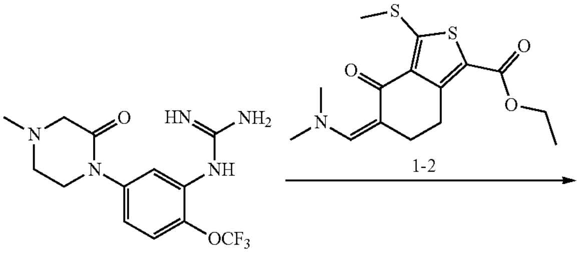

14-3

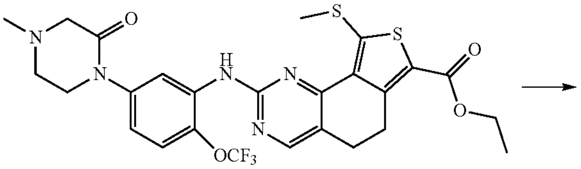

14-4

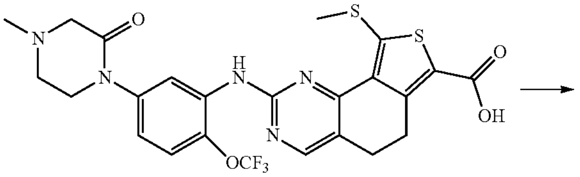

14-5

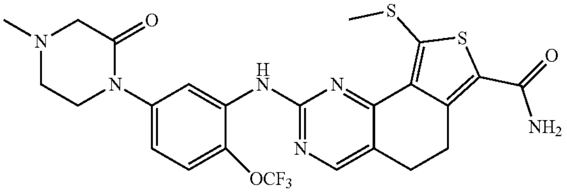

14

Step 1: Synthesis of Compound 14-2

Compound 14-1 (2 g, 7.81 mmol, 1.1 eq) was dissolved in 1,4-dioxane (30 mL), and then 1-methyl-3-oxopiperazine (810.63 mg, 7.10 mmol, 1 eq) was added thereto, then the system was replaced with nitrogen three times. Cesium carbonate (4.63 g, 14.20 mmol, 2 eq) was added thereto, and the system was replaced with nitrogen again, then N,N-dimethylethylenediamine (626.02 mg, 7.10 mmol, 775.73 μL, 1 eq) was added thereto. Finally, the system was finally replaced with nitrogen again and copper iodide (676.26 mg, 3.55 mmol, 0.5 eq) was added thereto, and the reaction mixture was stirred at 120° C. for 16 hours. Additional 1-methyl-3-oxopiperazine (810.63 mg, 7.10 mmol, 1 eq) and cuprous iodide (676.26 mg, 3.55 mmol, 0.5 eq) were added, and stirring was continued at 120° C. for 24 hours. Water (50 mL) was added to the reaction system, the phases were separated, the aqueous phase was extracted with ethyl acetate (70 mL*3), then the phases were separated, and the organic phases was combined and dried over anhydrous sodium sulfate, filtered, and the filtrate was concentrated under reduced pressure to obtain the crude product. The crude product was purified by silica gel column chromatography (gradient elution: dichloromethane/methanol=100:0 to 90:10) to obtain compound 14-2.

Characterization of Compound 14-2

LCMS: m/z (ESI)=290.0 $[M+H]^+$.

$^1$H NMR(400 MHz, $CDCl_3$) δ: 2.41 (s, 3 H), 2.71-2.85 (m, 2 H), 3.23-3.32 (m, 2 H), 3.62-3.72 (t, J=5.20 Hz, 2 H), 3.94 (s, 2 H), 6.58-6.66 (dd, J=8.8, 2.4 Hz, 1 H), 6.73 -6.80 (d, J=2.4 Hz, 1 H), 7.10-7.15 (dd, J=8.8, 1.2 Hz, 1 H).

Step 2: Synthesis of Compound 14-3

6 M hydrochloric acid aqueous solution (1.20 mL, 6.94 eq) was added to compound 14-2 (300 mg, 1.04 mmol, 1 eq), then aminonitrile (348.82 mg, 8.30 mmol, 348.82 μL, 8 eq) was added thereto, and the mixture was stirred at 60° C. for 16 hours. The reaction system was diluted by adding water (2 mL), extracted with ethyl acetate (5 mL*2), and the phases were separated. The pH of the aqueous phase was adjusted to 13 with 1 M potassium hydroxide aqueous solution, then the aqueous phase was extracted with ethyl acetate (5 mL*3). The phases were separated, and the organic phase was dried over anhydrous sodium sulfate and filtered, and the filtrate was concentrated under reduced pressure to obtain compound 14-3.

Characterization of Compound 14-3

LCMS: m/z (ESI)=332.0 $[M+H]^+$.

$^1$H NMR (400 MHz, DMSO-$d_6$) δ: 2.26 (s, 3 H), 2.65-2.73 (m, 2 H), 3.08 (s, 2 H), 3.60-3.67 (t, J=5.20 Hz, 2 H), 5.27-5.34 (m, 2 H), 5.36-5.45 (m, 2 H), 6.81-6.89 (m, 2 H), 7.14-7.20 (m, 1 H).

Step 3: Synthesis of Compound 14-4

Compound 1-2 (200 mg, 603.70 μmol, 1 eq) was added to compound 14-3 (196.47 mg, 603.70 μmol, 1 eq) in N,N-dimethylformamide (2 mL), and the mixture was stirred at 110° C. for 16 hours. The reaction system was washed by adding water (5 mL), then extracted by adding ethyl acetate (5 mL*3). The phasesphases were separated, and the organic phase was dried over anhydrous sodium sulfate, filtered, and the filtrate was concentrated under reduced pressure to obtain the crude product. The crude product was separated by thin-layer preparative plate (developing agent: dichloromethane/methanol=10:1) to obtain compound 14-4.

Characterization of Compound 14-4

LCMS: m/z (ESI)=594.1 $[M+H]^+$.

$^1$H NMR (400 MHz, DMSO-$d_6$) δ: 1.26-1.33 (m, 3 H), 2.28 (s, 3 H), 2.59 (s, 3 H), 2.60-2.70 (m, 2 H), 2.76-2.82 (m, 2 H), 3.11 (s, 2 H), 3.22 (t, J=7.2 Hz, 2 H), 3.63-3.69 (t, J=5.2 Hz, 2 H), 4.18-4.28 (q, J=7.2 Hz, 2 H), 7.07-7.14 (d, J=8.4 Hz, 1 H), 7.35-7.42 (d, J=8.4 Hz, 1 H), 8.12-8.20 (m, 1 H), 8.39 (s, 1 H), 8.82 (s, 1 H).

Step 4: Synthesis of Compound 14-5

Compound 14-4 (80 mg, 134.76 μmol, 1 eq) was dissolved in anhydrous tetrahydrofuran (1.6 mL) solution, then anhydrous ethanol (0.4 mL) and water (0.4 mL) were added thereto, and then lithium hydroxide monohydrate (28.28 mg, 673.81 μmol, 5 eq) were added. Nitrogen was degassed under reduced pressure three times, and after the addition, the temperature was raised to 45° C. and the reaction mixture was stirred for 5 hours. The pH of the reaction system was adjusted to 7 with 1 M hydrochloric acid aqueous solution, and then the organic solvent in the system was evaporated to dryness by rotary evaporation with a water pump, and the remaining aqueous solution was freeze-dried to obtain the crude product. Methanol (5 mL) was added to the crude product, and the mixture was sonicated for five minutes and filtered, and the filter cake was dried over a water pump to obtain compound 14-5.

Characterization of Compound 14-5

LCMS: m/z (ESI)=566.0 $[M+H]^+$.

$^1$H NMR(400 MHz, DMSO-$d_6$) δ: 2.55 (s, 3 H), 2.67 (s, 3 H), 2.75-2.80 (m, 4 H), 3.14 (s, 2 H), 3.20 (t, J=7.2 Hz, 2 H), 3.77-3.85 (m, 2 H), 7.08-7.15 (m, 1 H), 7.40-7.48 (m, 1 H), 8.05-8.13 (m, 1 H), 8.37 (s, 1 H).

Step 5: Synthesis of Compound 14-6

Compound 14-5 (30 mg, 53.04 μmol, 1 eq) was dissolved in anhydrous tetrahydrofuran (0.5 mL), oxalyl chloride (53.86 mg, 424.34 μmol, 37.14 μL, 8 eq) was added at 0° C., the system was replaced with nitrogen three times, and then N,N-dimethylformamide (387.71 μg, 5.30 μmol, 4.08e-1 μL, 0.1 eq) was added thereto, and the mixture was stirred at 0° C. for 0.5 hours. The reaction system was poured into 25% ammonia water (5 mL) and stirred for 0.5 hours at 20 ° C. Ethyl acetate (15 mL*4) was added to the reaction system for extraction, the phases were separated, the organic phase was dried over anhydrous sodium sulfate, filtered, and the filtrate was concentrated under reduced pressure to obtain the crude product. The crude product was purified by HPLC preparative chromatography (HPLC preparation method: Waters Xbridge BEH preparative chromatograph; chromatographic column: Phenomenex C18 100*30 mm*10 μm; mobile phase A: 10 mM ammonium bicarbonate aqueous solution, mobile phase B: acetonitrile; running gradient B %: 20% to 55%, 10 min) to obtain compound 14.

Characterization of Compound 14
LCMS: m/z (ESI)=565.1 $[M+H]^+$.
$^1H$ NMR(400 MHz, DMSO-$d_6$) δ: 2.29 (s, 3 H), 2.56 (s, 3 H), 2.69-2.79 (m, 4 H), 3.07-3.16 (m, 4 H), 3.63-3.70 (t, J=5.2 Hz, 2H), 7.06-7.12 (m, 1 H), 7.36-7.42 (m, 1 H), 7.42-7.49 (m, 2 H), 8.19-8.24 (d, J=2.4 Hz, 1 H), 8.38 (s, 1 H), 8.75 (s, 1 H).
Example 15
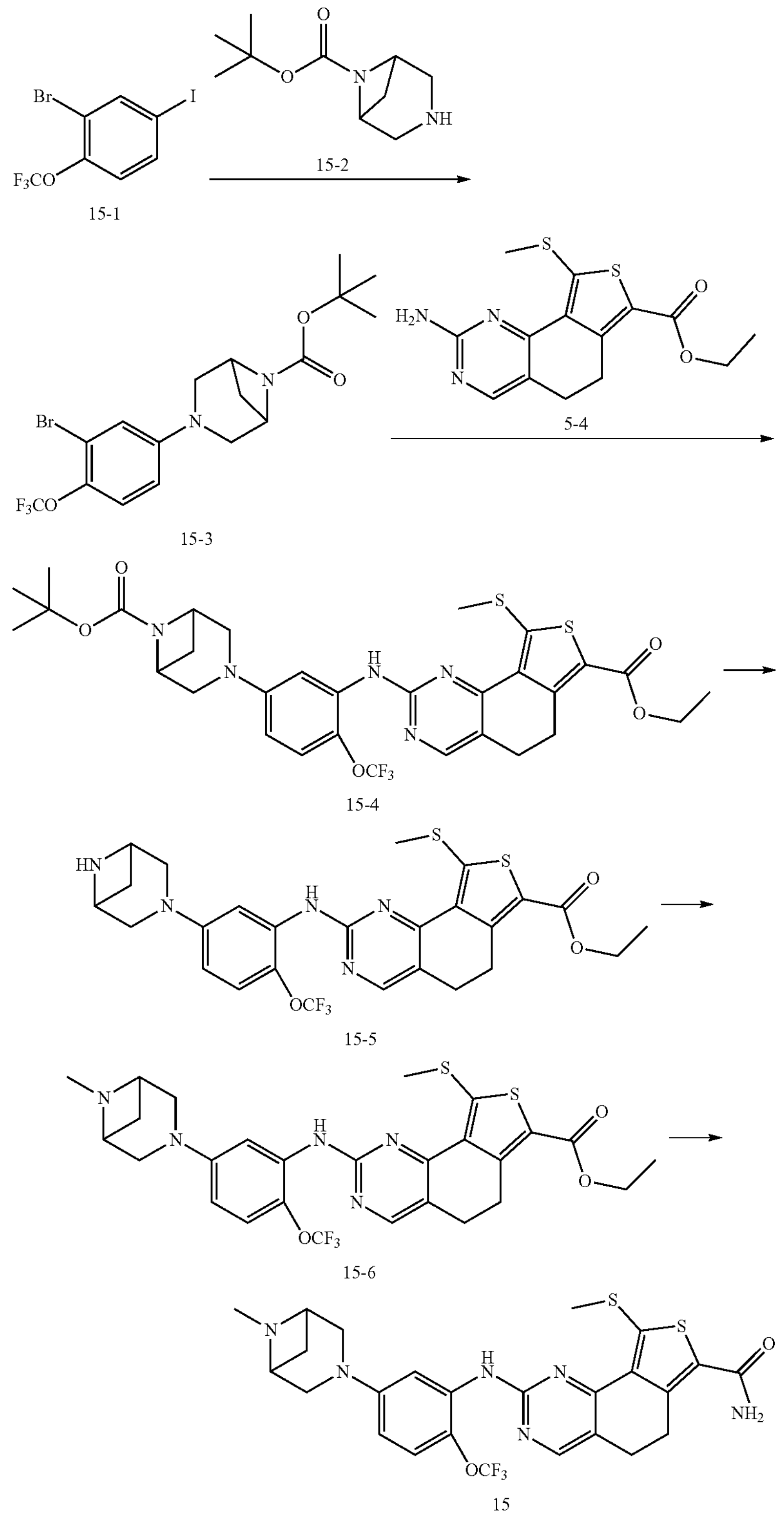

Step 1: Synthesis of Compound 15-3

Compound 15-1 (1 g, 2.73 mmol, 1 eq), compound 15-2 (540.37 mg, 2.73 mmol, 1 eq), 4,5-bis(diphenylphosphine)-9,9-dimethyl xanthene (157.70 mg, 272.55 μmol, 0.1 eq), tris(dibenzylideneacetone)dipalladium (249.58 mg, 272.55 μmol, 0.1 eq), sodium tert-butoxide (785.80 mg, 8.18 mmol, 3 eq) were dissolved in anhydrous toluene (20 mL), and the reaction mixture was stirred at 60° C. for 16 hours under nitrogen atmosphere. After the reaction was completed, the reaction mixture was concentrated under reduced pressure to obtain the crude product. The crude product was purified by silica gel column chromatography (gradient elution: petroleum ether/ethyl acetate=100:0 to 90:10) to obtain compound 15-3.

Characterization of Compound 15-3

LCMS: m/z (ESI)=381.0, 383.0 $[M-55]^+$.

$^1$H NMR (400 MHz, $CDCl_3$) δ: 7.18-7.22 (m, 1 H), 6.92 (d, J=3.0 Hz, 1 H), 6.62 -6.66 (m, 1 H), 4.31 (d, J=5.0 Hz, 2 H), 3.67-4.04 (m, 2 H), 3.27 (d, J=10.4 Hz, 2 H), 2.68 -2.72 (m, 1 H), 1.48 (d, J=8.7 Hz, 1 H), 1.39 (s, 9 H).

Step 2: Synthesis of Compound 15-4

Compound 5-4 (240 mg, 746.69 μmol, 1 eq), compound 15-3 (391.79 mg, 896.03 μmol, 1.2 eq), palladium acetate (8.38 mg, 37.33 μmol, 0.05 eq), 4,5-bis(diphenylphosphino)-9,9-dimethylxanthene (21.60 mg, 37.33 μmol, 0.05 eq), cesium carbonate (729.86 mg, 2.24 mmol, 3 eq) were dissolved in 1,4-dioxane (12 mL), and the mixture was stirred at 110° C. for 40 hours under nitrogen atmosphere. Ethyl acetate (10 mL), water (5 mL) and saturated brine (5 mL) were added to the reaction mixture, the phases were separated, the organic phase was dried over anhydrous sodium sulfate and filtered, and the filtrate was concentrated under reduced pressure to obtain the crude product to obtain compound 15-4.

Characterization of Compound 15-4

LCMS: m/z (ESI)=678.2 $[M+H]^+$.

$^1$H NMR (400 MHz, $CDCl_3$) δ: 8.30 (s, 1 H), 7.92 (s, 1 H), 7.30-7.41 (m, 1 H), 7.15-7.19 (m, 1 H), 6.32 -6.44 (m, 1 H), 4.19-4.46 (m, 4 H), 3.71-4.14 (m, 2 H), 3.21-3.47 (m, 4 H), 2.83 (t, J=7.2 Hz, 2 H), 2.65 (s, 4 H), 1.49 (d, J=8.4 Hz, 1 H), 1.36-1.43 (m, 12 H).

Step 3: Synthesis of Compound 15-5

Compound 15-4 (150 mg, 221.32 μmol, 1 eq) was dissolved in dichloromethane (5 mL), then trifluoroacetic acid (770.00 mg, 6.75 mmol, 0.5 mL, 30.51 eq) was added thereto, and the mixture was stirred at 20° C. for 16 hours. The solvent was concentrated to dryness under reduced pressure. Water (10 mL) and ethyl acetate (10 mL) were added to the crude product, then the pH was adjusted to greater than 8 with saturated sodium bicarbonate aqueous solution, and the phases were separated, the organic phase was dried over anhydrous sodium sulfate, filtered, and the solvent was concentrated to dryness under reduced pressure to obtain compound 15-5.

Characterization of Compound 15-5

LCMS: m/z (ESI)=578.2 $[M+H]^+$.

$^1$H NMR (400 MHz, $CDCl_3$) δ: 8.31 (s, 1 H), 7.93 (d, J=3.0 Hz, 1 H), 7.26 (s, 1 H), 7.18-7.22 (m, 1 H), 6.33 -6.35 (m, 1 H), 5.31 (s, 1 H), 4.36 -4.40 (m, 2 H), 3.92 (d, J=5.8 Hz, 2 H), 3.51-3.73 (m, 4 H), 3.33 (t, J=7.2 Hz, 2 H), 2.83 (t, J=7.2 Hz, 3 H), 2.64 (s, 3 H), 1.60 -1.65 (m, 1 H), 1.40 (t, J=7.2 Hz, 3 H).

Step 4: Synthesis of Compound 15-6

Compound 15-5 (120 mg, 207.74 μmol, 1 eq) was dissolved in anhydrous tetrahydrofuran (6.5 mL), and formaldehyde aqueous solution (238.46 mg, 2.94 mmol, 218.77 μL, 14.14 eq) with purity of 37% was added thereto, then acetic acid (229.45 mg, 830.97 μmol, 218.52 μL, 4 eq) was added thereto, and the mixture was stirred at 25° C. for 15 minutes, then sodium acetate borohydride (176.12 mg, 830.97 μmol, 4 eq) was added thereto, and the mixture was stirred at 25° C. for 45 minutes under nitrogen atmosphere. Ethyl acetate (10 mL), water (5 mL) and saturated sodium bicarbonate aqueous solution (5 mL) were added to the reaction mixture, the phases was separated, and the organic phase was dried over anhydrous sodium sulfate and filtered to obtain the crude product. The crude product was purified by silica gel column chromatography (gradient elution: dichloromethane/methanol=100:0 to 90:10) to obtain compound 15-6.

Characterization of Compound 15-6

LCMS: m/z (ESI)=592.2 $[M+H]^+$.

$^1$H NMR (400 MHz, $CDCl_3$) δ: 8.32 (s, 1 H), 8.03 (d, J=2.9 Hz, 1 H), 7.30 (s, 1 H), 7.20 -7.22 (m, 1 H), 6.34 -6.40 (m, 1 H), 4.36-4.40 (m, 2 H), 4.04 (d, J=4.1 Hz, 2 H), 3.54 -3.74 (m, 4 H), 3.33 (t, J=7.2 Hz, 2 H), 2.84 (t, J=7.2 Hz, 2 H), 2.64 (s, 3 H), 2.34 (s, 3 H), 1.76 (d, J=9.2 Hz, 1 H), 1.40 (t, J=7.2 Hz, 3 H).

Step 5: Synthesis of Compound 15

Compound 15-6 (90 mg, 152.11 μmol, 1 eq) and ammonium chloride (48.82 mg, 912.68 μmol, 6 eq) were dissolved in 1 M solution (1.52 mL, 10 eq) of lithium bis(trimethylsilyl)amide in n-hexane, and the mixture was stirred at 20° C. for 2 hours under nitrogen atmosphere. Methanol (3 mL) was added to the reaction mixture to quench the reaction, and then the solvent was concentrated to dryness under reduced pressure. The crude product was purified by HPLC preparative chromatography (HPLC preparation method: Waters Xbridge BEH preparative chromatograph; chromatographic column: Phenomenex C18 100*30 mm*10 μm; mobile phase A: 10 mM ammonium bicarbonate aqueous solution, mobile phase B: acetonitrile; running gradient: acetonitrile %: 15% to 85%, 8 min) to obtain compound 15.

Characterization of Compound 15

LCMS: m/z (ESI)=563.2 $[M+H]^+$.

1H NMR (400 MHz, $CD_3OD$) δ: 8.30 (s, 1 H), 7.63 (d, J=2.8 Hz, 1 H), 7.21 (d, J=9.0 Hz, 1 H), 6.50 -6.55 (m, 1 H), 3.60-3.80 (m, 4 H), 3.44-3.57 (m, 2 H), 3.23 (t, J=7.2 Hz, 2 H), 2.84 (t, J=7.2 Hz, 2 H), 2.50-2.72 (m, 4 H), 2.19 (s, 3 H), 1.70 (d, J=8.4 Hz, 1 H).

Example 16

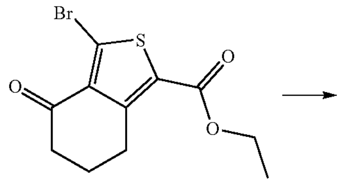

6-8

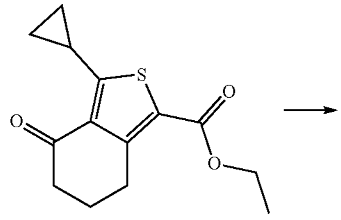

16-1

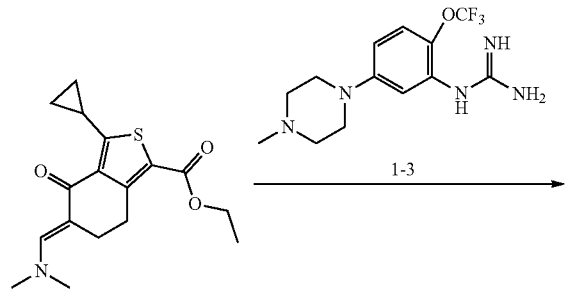

1-3

16-2

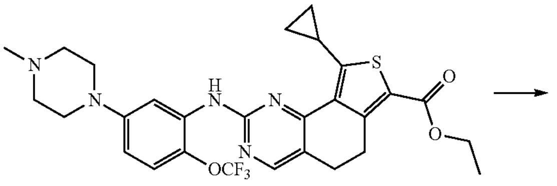

16-3

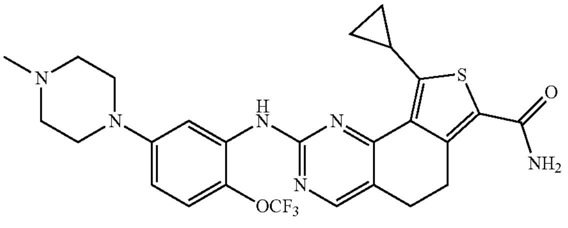

16

Step 1: Synthesis of Compound 16-1

Compound 6-8 (400 mg, 1.32 mmol, 1 eq), cyclopropylboronic acid (147.33 mg, 1.72 mmol, 1.3 eq), potassium phosphate (1.01 g, 4.75 mmol, 3.6 eq), palladium acetate (29.62 mg, 131.94 μmol, 0.1 eq), tricyclohexylphosphine (111.00 mg, 395.82 μmol, 128.32 μL, 0.3 eq) were added to a reaction flask, then anhydrous toluene (12 mL) and water (0.6 mL) were added thereto, and the mixture was stirred at 80° C. for 16 hours after nitrogen was degassed under reduced pressure three times. After the reaction was completed, the reaction mixture was concentrated to dryness under reduced pressure to obtain the crude product. The crude product was purified by silica gel column chromatography (gradient elution: dichloromethane/methanol=100:0 to 90:10) to obtain compound 16-1.

Characterization of Compound 16-1

LCMS: m/z (ESI)=265.1 $[M+H]^+$.

$^1H$ NMR (400 MHz, $CDCl_3$) δ: 4.30 -4.38 (m, 2 H), 3.41 (s, 1 H), 3.21 (t, J=6.2 Hz, 2 H), 2.50-2.65 (m, 2 H), 2.05 (t, J=6.3 Hz, 2 H), 1.37 (t, J=7.2 Hz, 3 H), 1.25-1.32 (m, 2 H), 0.77-0.91 (m, 2 H).

Step 2: Synthesis of Compound 16-2

Compound 16-1 (225 mg, 851.18 μmol, 1 eq) was dissolved in anhydrous tetrahydrofuran (4.5 mL), and then tert-butoxy bis(dimethylamino)methane (445.04 mg, 2.55 mmol, 527.30 3 eq) was added thereto, and the mixture was stirred at 80° C. for 20 hours. After the reaction was completed, the solvent was concentrated to dryness under reduced pressure to obtain the crude compound 16-2, which was directly used in the next step without purification.

Characterization of Compound 16-2

LCMS: m/z (ESI)=293.1 $[M-26]^+$.

Step 3: Synthesis of Compound 16-3

Compound 16-2 (270 mg, 845.29 μmol, 1 eq) was dissolved in N,N-dimethylformamide (3.5 mL), then compound 1-3 (268.22 mg, 845.29 μmol, 1 eq) was added thereto, and the mixture was stirred at 110 ° C. for 20 hours. After the reaction was completed, ethyl acetate (50 mL) and water (50 mL) were added to the reaction mixture, and the phases were separated. The organic phase was dried over anhydrous sodium sulfate and filtered, and the solvent was concentrated to dryness under reduced pressure to obtain the crude product. The crude product was purified by silica gel column chromatography (gradient elution: dichloromethane/methanol=100:0 to 90:10) to obtain compound 16-3.

Characterization of Compound 16-3

LCMS: m/z (ESI)=574.3 $[M+H]^+$.

$^1H$ NMR (400 MHz, $CDCl_3$) δ: 8.35 (s, 1 H), 8.09 (d, J=2.8 Hz, 1 H), 7.11-7.16 (m, 2 H), 6.52-6.54 (m, 1 H), 4.34 (d, J=7.2 Hz, 2 H), 3.55 (s, 1 H), 3.28 -3.30 (m, 6 H), 2.79 -2.82 (m, 2 H), 2.57-2.73 (m, 4 H), 2.42 (s, 3 H), 1.38 (t, J=7.2 Hz, 3 H), 1.17-1.25 (m, 2 H), 0.82-0.90 (m, 2 H).

Step 4: Synthesis of Compound 16

Compound 16-3 (120 mg, 209.19 μmol, 1 eq) and ammonium chloride (67.14 mg, 1.26 mmol, 6 eq) were dissolved in 1 M solution (2.09 mL, 10 eq) of lithium bis(trimethylsilyl)amide in n-hexane, then the mixture was stirred at 20° C. for 1 hour under nitrogen atmosphere. After the reaction was completed, methanol (3 mL) was added to the reaction mixture to quench the reaction, and the solvent was concentrated to dryness under reduced pressure. The crude product was purified by HPLC preparative chromatography (HPLC preparation method: Waters Xbridge BEH preparative chromatograph; chromatographic column: Phenomenex C18 100*30 mm*10 μm; mobile phase A: 10 mM ammonium bicarbonate aqueous solution, mobile phase B: acetonitrile; running gradient B %: 15% to 85%, 8min) to obtain compound 16.

Characterization of Compound 16

LCMS: m/z (ESI)=545.3 $[M+H]^+$.

1H NMR (400 MHz, $CD_3OD$) δ: 8.32 (s, 1 H), 7.60 (m, 1 H), 7.19 -7.23 (m, 1 H), 6.76-6.72 (m, 1 H), 3.39 -3.48 (m, 1 H), 3.25 (s, 4 H), 3.17 (t, J=6.8 Hz, 2 H), 2.80 (t, J=6.8 Hz, 2 H), 2.67 (s, 4 H), 2.40 (s, 3 H), 1.04-1.10 (m, 2 H), 0.75-0.79 (m, 2 H).

Example 17

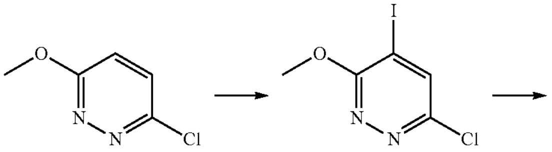

17-1

17-2

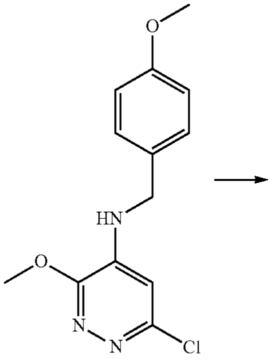

17-3

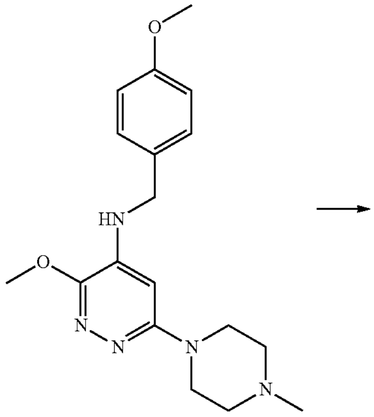

17-4

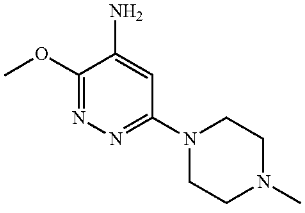

17-5

-continued

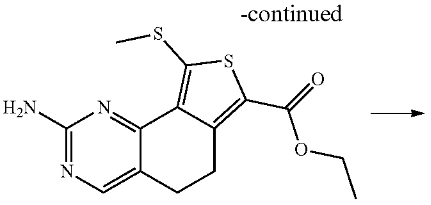

5-4

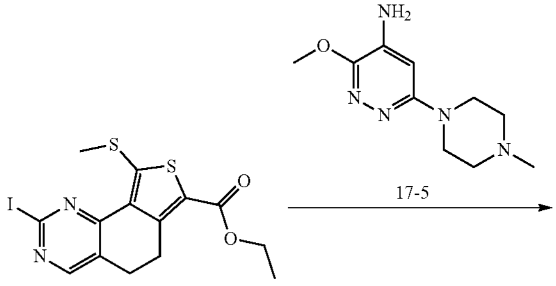

17-6

17-5

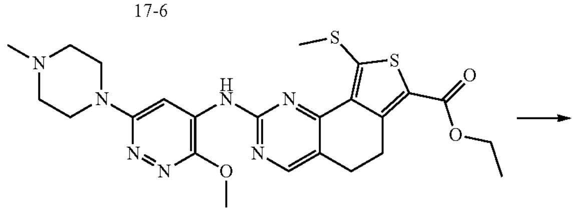

17-7

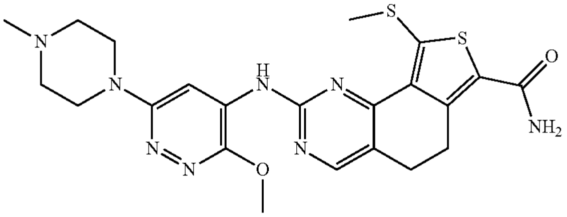

17

Step 1: Synthesis of Compound 17-2

Under nitrogen atmosphere at −75° C., a solution (5 mL) of compound 17-1 (1.25 g, 8.65 mmol, 1 eq) in anhydrous tetrahydrofuran was added to 0.1 M solution (172.94 mL, 2 eq) of lithium 2,2,6,6-tetramethylpiperidine in tetrahydrofuran, and the mixture was stirred for 0.5 hours, then iodine (2.59 g, 10.20 mmol, 2.06 mL, 1.18 eq) was added thereto at −75° C., and the mixture was stirred for 3 hours. Saturated ammonium chloride aqueous solution (150 mL) was added to the reaction system for washing, the phases were separated, extracted with ethyl acetate (100 mL*3), and the organic phases were combined and dried over anhydrous sodium sulfate, filtered, and the filtrate was concentrated under reduced pressure to obtain the crude product. The crude product was purified by silica gel column chromatography (gradient elution: petroleum ether/ethyl acetate=100:0 to 95:5) to obtain compound 17-2.

Characterization of Compound 17-2

LCMS: m/z (ESI)=271.0 $[M+H]^+$.

$^1H$ NMR(400 MHz, DMSO-$d_6$) δ: 4.05 (s, 3 H), 8.44 (s, 1 H).

Step 2: Synthesis of Compound 17-3 p-Methoxybenzylamine (912.99 mg, 6.66 mmol, 861.31 μL, 3 eq), potassium fluoride (386.66 mg, 6.66 mmol, 155.91 3 eq) were added to compound 17-2 (600 mg, 2.22 mmol, 1 eq) in dimethyl sulfoxide (12 mL), and the mixture was stirred at 120° C. for 3 hours. Water (10 mL) was added to the reaction system, and the reaction system was extracted with ethyl acetate (10 mL*3), the phases were separated, and the organic phases were combined and concentrated under reduced pressure, and purified by silica gel column chromatography (gradient elution: petroleum ether/ethyl acetate=100:0 to 60:40) to obtain compound 17-3.

Characterization of Compound 17-3

LCMS: m/z (ESI)=279.9 $[M+H]^+$.

$^1$H NMR (400 MHz, DMSO-$d_6$) δ: 3.71 (s, 3 H), 4.00 (s, 3 H), 4.28-4.38 (d, J=6.4 Hz 2 H), 6.45 (s, 1 H), 6.85-6.92 (d, J=8.8 Hz, 2 H), 7.21-7.29 (d, J=8.8 Hz, 2 H), 7.50 -7.58 (m, 1 H).

Step 3: Synthesis of Compound 17-4

Compound 17-3 (250 mg, 893.75 μmol, 1 eq) was dissolved in 1,4-dioxane (2 mL), and 2-dicyclohexylphosphino-2,6-diisopropoxy-1,1-biphenyl (208.53 mg, 446.87 μmol, 0.5 eq), (2-dicyclohexylphosphino-2,6-diisopropoxy-1,1-biphenyl)[2-(2-amino-1,1-biphenyl)]palladium(II) (373.75 mg, 446.87 μmol, 0.5 eq) were added thereto, and the system was replaced with nitrogen three times, then sodium tert-butoxide (171.78 mg, 1.79 mmol, 2 eq), N-methylpiperazine (179.04 mg, 1.79 mmol, 198.27 μL, 2 eq) were added thereto, and the mixture was stirred at 110° C. for 4 hours. Water (10 mL) was added to the reaction mixture for washing, and then the reaction mixture was extracted with ethyl acetate (10 mL*4). The phases were separated, and the organic phases were dried over anhydrous sodium sulfate and filtered, and the filtrate was concentrated under reduced pressure to obtain the crude product. The crude product was purified by silica gel column chromatography (gradient elution: dichloromethane/methanol=100:0 to 90:10) to obtain compound 17-4.

Characterization of Compound 17-4

LCMS: m/z (ESI)=344.2 $[M+H]^+$.

$^1$H NMR (400 MHz, $CDCl_3$) δ: 2.36 (s, 3 H), 2.49-2.63 (m, 4 H), 3.47-3.50 (m, 4 H), 3.82 (s, 3 H), 4.08 (s, 3 H), 4.23-4.30 (d, J=5.2 Hz, 2 H), 5.93 (s, 1 H), 6.89-6.93 (d, J=8.8 Hz, 2 H), 7.23-7.26 (d, J=8.8 Hz, 2 H).

Step 4: Synthesis of Compound 17-5

Trifluoroacetic acid (6 mL) was added to compound 17-4 (190 mg, 553.25 μmol, 1 eq), and the mixture was stirred at 50° C. for 16 hours. The reaction system was directly concentrated under reduced pressure to obtain the crude product. Water (5 mL*3) was added to the system, then the system was washed with dichloromethane (5 mL*3). The pH of the aqueous phase was adjusted to 14 with 1 M sodium hydroxide aqueous solution, then the aqueous phase extracted with dichloromethane (20 mL*6). The phases were separated, the organic phase was dried over anhydrous sodium sulfate and filtered, and the filtrate was concentrated under reduced pressure to obtain compound 17-5.

Characterization of Compound 17-5

LCMS: m/z (ESI)=224.0 $[M+H]^+$.

$^1$H NMR (400 MHz, $CD_3OD$) δ: 2.35 (s, 3 H), 2.52-2.62 (m, 4 H), 3.40-3.44 (m, 4 H), 3.99 (s, 3 H), 6.30 (s, 1 H).

Step 5: Synthesis of Compound 17-6

Cesium iodide (96.88 mg, 684.47 μmol, 59.43 μL, 1.1 eq), iodine (86.86 mg, 342.23 μmol, 68.94 μL, 0.55 eq), cuprous iodide (37.92 mg, 199.12 μmol, 0.32 eq), isoamyl nitrite (116.63 mg, 995.59 μmol, 134.06 μL, 1.6 eq) were added to compound 5-4 (200 mg, 622.24 μmol, 1 eq) in ethylene glycol dimethyl ether (20 mL), and the mixture was stirred at 70° C. for 18 hours. Ammonia water (10 mL) was added to the reaction system for washing, and then the reaction system was washed with saturated aqueous sodium thiosulfate (20 mL), and the organic phases were combined and dried over anhydrous sodium sulfate, filtered, and the filtrate was concentrated under reduced pressure to obtain the crude product. The crude product was purified by silica gel column chromatography (gradient elution: dichloromethane/methanol=100:0 to 90:10) to obtain compound 17-6.

Characterization of Compound 17-6

LCMS: m/z (ESI)=432.9 $[M+H]^+$.

Step 6: Synthesis of Compound 17-7

Compound 17-5 (50 mg, 223.94 μmol, 1.5 eq) was dissolved in 1,4-dioxane (2 mL), then compound 17-6 (64.54 mg, 149.29 μmol, 1 eq), 4,5-bis(diphenylphosphino)-9,9-dimethylxanthene (3.46 mg, 5.97 μmol, 0.04 eq), cesium carbonate (145.93 mg, 447.88 μmol, 3 eq) were added thereto, the system was replaced with nitrogen three times and then palladium acetate (670.35 μg, 2.99 μmol, 0.02 eq) was added thereto, the system was replaced with nitrogen three times, and the mixture was stirred at 110° C. for 2 hours. Water (5 mL) was added to the reaction system, then ethyl acetate (10 mL*3) was added for extraction. The phases were separated, and the organic phase was directly concentrated under reduced pressure to obtain the crude product. The crude product was purified by thin-layer preparative plate (developing agent: dichloromethane/methanol=10:1) to obtain compound 17-7.

Characterization of Compound 17-7

LCMS: m/z (ESI)=528.1 $[M+H]^+$. $^1$H NMR (400 MHz, DMSO-$d_6$) δ: 1.29-1.32 (m, 3 H), 2.31-2.35 (m, 4 H), 2.41 (s, 3 H), 2.65-2.69 (m, 4 H), 2.71 (s, 3 H), 2.82-2.87 (m, 2 H), 3.24-3.27 (m, 2 H), 4.02 (s, 3 H), 4.27-4.31 (m, 2 H), 8.04-8.13 (m, 1 H), 8.18 (s, 1 H), 8.56 (s, 1 H).

Step 7: Synthesis of Compound 17

Ammonium chloride (21.29 mg, 397.98 μmol, 6 eq) was added to a solution of compound 17-7 (35 mg, 66.33 μmol, 1 eq) in anhydrous tetrahydrofuran (3.5 mL), and then 1 M solution (663.30 10 eq) of lithium bis(trimethylsilyl)amide in tetrahydrofuran was added thereto, and the mixture was stirred at 20° C. for 2 hours. Saturated ammonium chloride aqueous solution (10 mL) was added to the reaction system, then the reaction system was extracted with ethyl acetate (10 mL*3), and the phases were separated, the organic phases were combined, dried over anhydrous sodium sulfate, filtered, and the filtrate was concentrated under reduced pressure to obtain the crude product. The crude product was purified by HPLC preparative chromatography (HPLC preparation method: Waters Xbridge BEH preparative chromatograph; chromatographic column: C18 100*30 mm*10 μm; mobile phase A: 10 mM ammonium bicarbonate aqueous solution, mobile phase B: acetonitrile; running gradient B %: 10% to 40%, 8 min) to obtain compound 17.

Characterization of Compound 17

LCMS: m/z (ESI)=499.2 $[M+H]^+$.

$^1H$ NMR (400 MHz, DMSO-$d_6$) δ: 2.22 (s, 3 H), 2.41-2.45 (m, 4 H), 2.66 (s, 3 H), 2.78-2.85 (m, 2 H), 3.10-3.17 (m, 2 H), 3.41-3.45 (m, 4 H), 4.02 (s, 3 H), 7.49 (s, 2 H), 8.03 (s, 1 H), 8.20 (s, 1 H), 8.53 (s, 1 H).

Example 18

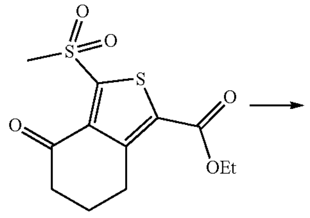

2-1

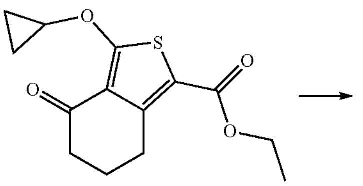

18-1

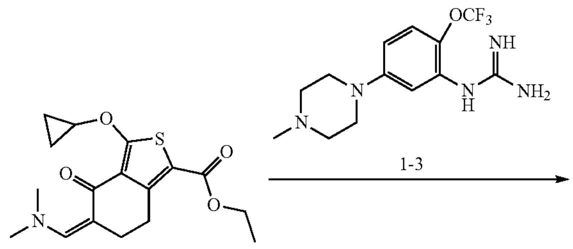

18-2

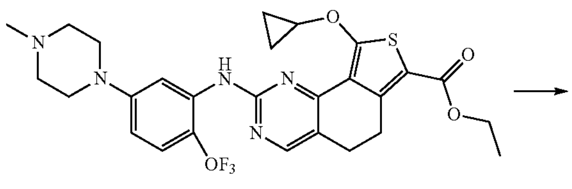

18-3

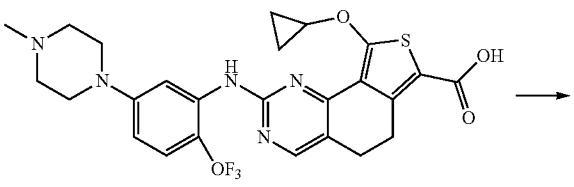

18-4

-continued

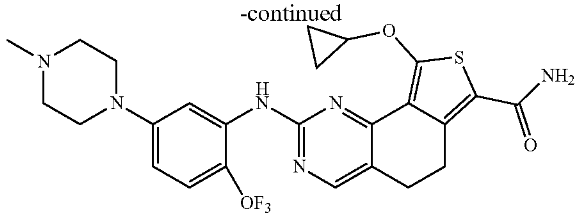

18

Step 1: Synthesis of Compound 18-1

Under nitrogen atmosphere at 0° C., sodium hydride (132.29 mg, 3.31 mmol, 2 eq) with a purity of 60% was added to a solution of cyclopropanol (192.08 mg, 3.31 mmol, 2 eq) in anhydrous tetrahydrofuran (8 mL), and the mixture was stirred at 0° C. for 0.5 hours, then compound 2-1 (500 mg, 1.65 mmol, 1 eq) was added thereto, and the reaction was continued at 0° C. for 1 hour. After the reaction was completed, water (5 mL) was added thereto, and the mixture was extracted with ethyl acetate (10 mL*2). The phases was separated, and the organic phase was dried over anhydrous sodium sulfate, filtered, and the filtrate was concentrated under reduced pressure to obtain the crude product, which was separated by thin-layer chromatography (developing agent: petroleum ether/ethyl acetate=100:0 to 60:40) to obtain compound 18-1.

Characterization of Compound 18-1

LCMS: m/z (ESI)=280.9 $[M+H]^+$.

1H NMR (400 MHz, $CDCl_3$) δ: 0.90-0.97 (m, 2 H), 1.06-1.14 (m, 2 H), 1.33-1.42 (t, J=7.2 Hz, 3 H), 1.96-2.06 (m, 2 H), 2.44-2.53 (t, J=6.0 Hz, 2 H), 3.16-3.23 (t, J=7.2 Hz, 2 H), 4.05-4.12 (m, 1 H), 4.28-4.39 (q, J=7.2 Hz, 2 H).

Step 2: Synthesis of Compound 18-2

Compound 18-1 was dissolved in anhydrous toluene (10 mL), tert-butoxy bis(dimethylamino)methane (1.99 g, 11.41 mmol, 2.36 mL, 20 eq) was added thereto, and the mixture was stirred at 90° C. for 2 hours. After the reaction was completed, water (10 mL) was added to the reaction system, and the mixture was extracted with ethyl acetate (10 mL*3). The phases were separated, and the organic phase was dried over anhydrous sodium sulfate, filtered, and the filtrate was concentrated under reduced pressure to obtain compound 18-2.

Characterization of Compound 18-2

LCMS: m/z (ESI)=308.9 $[M-26]^+$.

Step 3: Synthesis of Compound 18-3

Compound 18-2 (150 mg, 447.20 μmol, 1 eq) was dissolved in N,N-dimethylformamide (2 mL), then compound 1-3 (141.90 mg, 447.20 μmol, 1 eq) was added thereto, and the mixture was stirred at 110° C. for 4 hours. After the reaction was completed, water (5 mL) was added to the reaction system, and the reaction system was extracted with ethyl acetate (10 mL*3). The phases were separated, and the organic phases were combined, dried over anhydrous sodium sulfate, filtered, and the filtrate was concentrated under reduced pressure to obtain the crude product, which was purified by the column chromatography (gradient eluent: dichloromethane/methanol=100:0 to 90:10) to obtain compound 18-3.

Characterization of Compound 18-3

LCMS: m/z (ESI)=590.1 [M+H]$^+$.

$^1$H NMR (400 MHz, $CDCl_3$) δ: 0.88-0.97 (m, 2 H), 1.05-1.14 (m, 2 H), 1.38-1.42 (t, J=7.2 Hz, 3 H), 2.41 (s, 3 H), 2.57-2.71 (m, 4 H), 2.78-2.88 (t, J=7.2 Hz, 2 H), 3.26-3.36 (m, 6 H), 4.14-4.17 (m, 1 H), 4.31-4.39 (m, 2 H), 6.46-6.52 (m, 1 H), 7.11-7.17 (m, 1 H), 7.30 (s, 1 H), 8.28 (s, 1 H), 8.31-8.34 (d, J=2.8 Hz 1 H).

Step 4: Synthesis of Compound 18-4

Compound 18-3 (100 mg, 169.60 μmol, 1 eq) was dissolved in a mixed solvent of anhydrous tetrahydrofuran (4 mL), methanol (1 mL) and water (1 mL), and lithium hydroxide monohydrate (35.58 mg, 847.99 μmol, 5 eq) was added thereto, and the mixture was stirred at 45° C. for 3 hours. After the reaction was completed, the reaction system was concentrated under reduced pressure to remove the organic solvent, and the pH was adjusted to 7 with 2 N $HC_1$ aqueous solution, and the reaction system was directly concentrated under reduced pressure to obtain compound 18-4.

Characterization of Compound 18-4

LCMS: m/z (ESI)=562.1 [M+H]$^+$.

1H NMR (400 MHz, DMSO-$d_6$) δ: 0.71-0.81 (m, 4 H), 2.21 (s, 3 H), 2.44-2.46 (m, 4 H), 2.57-2.63 (m, 2 H), 3.09-3.15 (m, 4 H), 3.17-3.22 (m, 2 H), 3.98-4.07 (m, 1 H), 6.57-6.68 (m, 1 H), 7.10-7.22 (m, 1 H), 7.79-7.86 (d, J=2.8 Hz, 1 H), 7.97 (s, 1 H), 8.22 (s, 1 H).

Step 5: Synthesis of Compound 18

Compound 18-4 (171.77 mg, 1.35 mmol, 118.46 μL, 8 eq) was dissolved in anhydrous tetrahydrofuran (3 mL), oxalyl chloride (171.77 mg, 1.35 mmol, 118.46 μL, 8 eq) was added thereto at 0° C., and the system was replaced with nitrogen three times, then N,N-dimethylformamide (1.24 mg, 16.92 μmol, 1.30 μL, 0.1 eq) was added thereto, and the mixture was stirred at 0° C. for 0.5 hours, and then ammonia water (9 mL) with a purity of 25% was added thereto, and the mixture was stirred at 20° C. for 0.5 hours. After the reaction was completed, the reaction system was extracted with ethyl acetate (10 mL*3), and the phases were separated. The organic phase was dried over anhydrous sodium sulfate, filtered, and the filtrate was concentrated under reduced pressure to obtain the crude product, which was purified by HPLC (HPLC preparation method: Waters Xbridge BEH preparative chromatograph; chromatographic column: C18 75*30 mm*3 μm; mobile phase A: 10 mM ammonium bicarbonate aqueous solution, mobile phase B: acetonitrile; gradient B %: 30% to 70%, 8 min) to obtain compound 18.

Characterization of Compound 18

LCMS: m/z (ESI)=561.2 [M+H]$^+$.

1H NMR (400 MHz, DMSO-$d_6$) δ: 0.79-0.85 (m, 4 H), 2.21 (s, 3 H), 2.43-2.47 (m, 4 H), 2.66-2.70 (t, J=7.2 Hz, 2 H), 3.04-3.09 (t, J=7.2 Hz, 2 H), 3.11-3.15 (m, 4 H), 4.11-4.18 (m, 1 H), 6.65-6.71 (m, 1 H), 7.13-7.19 (d, J=8.8 Hz, 1 H), 7.35 (s, 2 H), 7.65-7.70 (d, J=2.8 Hz, 1 H), 8.20 (s, 1 H), 8.29 (s, 1 H).

Example 19

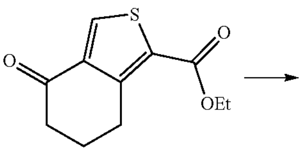

6-3

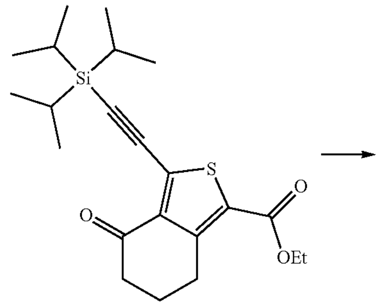

19-1

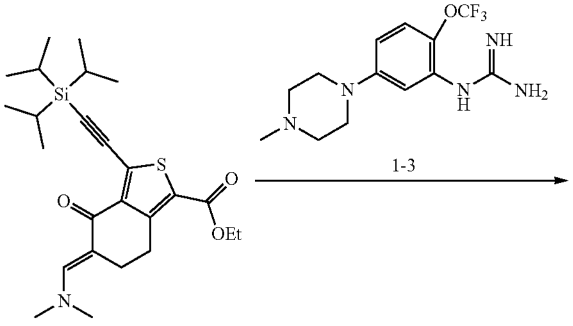

19-2

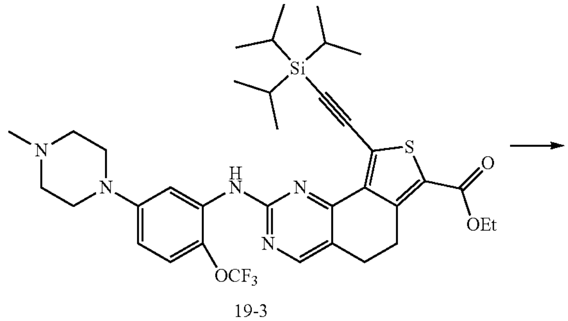

19-3

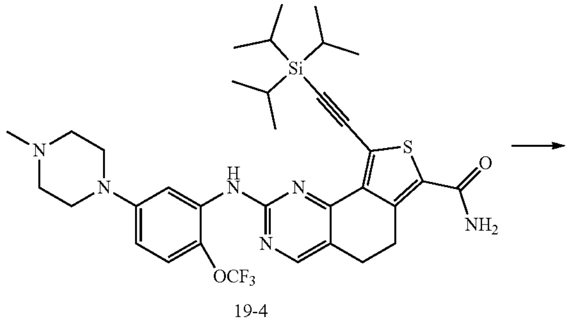

19-4

-continued

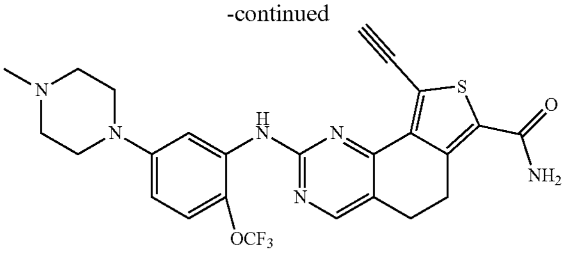

19

Step 1: Synthesis of Compound 19-1

Compound 6-3 (1.2 g, 5.35 mmol, 1 eq), (2-bromoethynyl) triisopropylsilane (1.47 g, 5.62 mmol, 1.05 eq), silver acetate (893.06 mg, 5.35 mmol, 273.95 μL, 1 eq), and palladium acetate (120.13 mg, 535.06 μmol, 0.1 eq) were dissolved in acetonitrile (45 mL), and the mixture was stirred at 80° C. for 72 hours. After the reaction was completed, the temperature was cooled to 20° C., and the reaction mixture was concentrated to dryness under reduced pressure to obtain the crude product, which was purified by silica gel column chromatography (gradient elution: petroleum ether/ethyl acetate=100:0 to 98:2) to obtain compound 19-1.

Characterization of Compound 19-1

LCMS: m/z (ESI)=405.2 $[M+H]^+$.

1H NMR (400 MHz, CDCl3) δ: 4.30-4.39 (m, 2 H), 3.18-3.25 (m, 2 H), 2.51-2.65 (m, 2 H), 1.97-2.14 (m, 2 H), 1.32-1.42 (m, 3 H), 1.17 (s, 21 H).

Step 2: Synthesis of Compound 19-2

Compound 19-1 (155 mg, 383.06 μmol, 1 eq) was dissolved in anhydrous tetrahydrofuran (2.5 mL), and then tert-butoxy bis(dimethylamino)methane (211.00 mg, 1.21 mmol, 0.25 mL, 3.16 eq) was added, and the mixture was stirred at 80° C. for 2 hours after the nitrogen was degassed under reduced pressure. After the reaction was completed, the temperature was cooled to 20° C., and the solvent was concentrated to dryness under reduced pressure to obtain crude compound 19-2, which was directly used in the next reaction.

Characterization of Compound 19-2

LCMS: m/z (ESI)=433.2 $[M-26]^+$.

Step 3: Synthesis of Compound 19-3

Compound 19-2 (170 mg, 369.79 μmol, 1 eq) was dissolved in N,N-dimethylformamide (2 mL), then compound 1-3 (117.34 mg, 369.79 μmol, 1 eq) was added thereto, and the mixture was stirred at 110° C. for 20 hours. After the reaction was completed, water (10 mL) and saturated brine (10 mL) were added to the reaction mixture, and the reaction mixture was extracted with ethyl acetate (20 mL). The phases were separated, and the organic phase was dried over anhydrous sodium sulfate, filtered, and the solvent was concentrated to dryness under reduced pressure to obtain the crude product, which was purified by silica gel column chromatography (gradient elution: dichloromethane/methanol=100:0 to 98:2) to obtain compound 19-3.

Characterization of Compound 19-3

LCMS: m/z (ESI)=714.3 $[M+H]^+$.

$^1$H NMR (400 MHz, $CDCl_3$) δ: 8.38 (s, 1 H), 8.20 (m, 1 H), 7.19 (s, 1 H), 7.14 (m, 1 H), 6.52 (m, 1 H), 4.37 (m, 2 H), 3.19-3.40 (m, 6 H), 2.81 (2 H), 2.53-2.70 (m, 4 H), 2.39 (s, 3 H), 1.40 (t, J=7.2 Hz, 3 H), 1.09-1.19 (m, 21 H).

Step 4: Synthesis of Compound 19-4

Compound 19-3 (60 mg, 84.04 μmol, 1 eq) and ammonium chloride (26.97 mg, 504.25 μmol, 6 eq) were dissolved in 1 M solution (2.09 mL, 10 eq) of lithium bis(trimethylsilyl)amide in n-hexane and the mixture was stirred at 20° C. for 1 hour under nitrogen atmosphere, then methanol (3 mL) was added to the reaction mixture to quench the reaction, and the solvent was concentrated to dryness under reduced pressure to obtain the crude compound 19-4.

Characterization of Compound 19-4

LCMS: m/z (ESI)=685.3 $[M+H]^+$.

Step 5: Synthesis of Compound 19

Compound 19-4 (55 mg, 80.31 μmol, 1 eq) and 1 M solution (1.2 mL, 14.94 eq) of tetrabutylammonium fluoride in tetrahydrofuran were dissolved in anhydrous tetrahydrofuran (2 mL), and the mixture was stirred at 20° C. for 20 hours. Saturated brine (5 mL) and water (5 mL) were added to the reaction mixture, then ethyl acetate (10 mL) was added thereto. After the mixture was filtered, the phases were separated, and the organic phase was dried over anhydrous sodium sulfate, filtered, and the solvent was concentrated to dryness under reduced pressure to obtain the crude product, which was purified by HPLC preparative chromatography (HPLC preparation method: Waters 2767/QDa preparative chromatograph; chromatographic column: C18 75*30 mm*3 μm; mobile phase A: $H_2O$ (with 0.2% formic acid), mobile phase B: acetonitrile; running gradient: B %: 1% to 40%, run for 8 min) to obtain the formate of compound 19.

Characterization of Compound 19

LCMS: m/z (ESI)=529.2 [M+H]+.

1H NMR (400 MHz, $CD_3OD$) δ: 9.01-9.13 (m, 1 H), 8.41-8.55 (m, 1 H), 7.98-8.09 (m, 1 H), 7.69-7.78 (m, 1 H), 7.08-7.24 (m, 1 H), 6.87-6.98 (m, 1 H), 6.66-6.82 (m, 1 H), 4.53-4.64 (m, 1 H), 3.39-3.46 (m, 2 H), 3.28-3.32 (m, 4 H), 3.05-3.12 (m, 2 H), 2.93 -3.02 (m, 4 H), 2.54-2.72 (m, 3 H).

Example 20

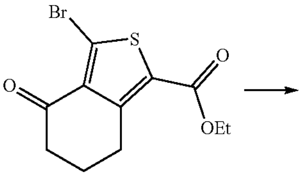

6-8

-continued

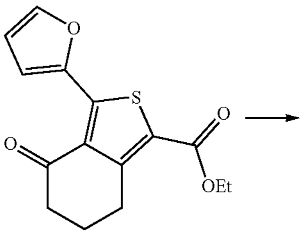

20-1

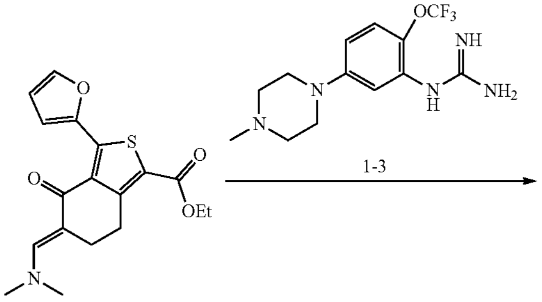

20-2

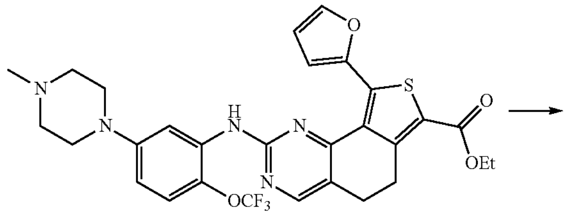

20-3

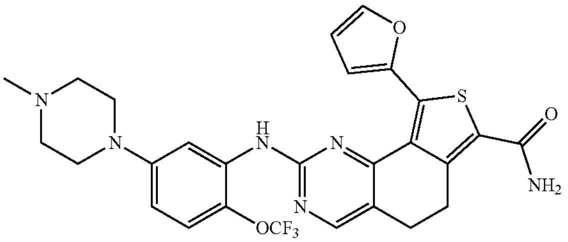

20

Step 1: Synthesis of Compound 20-1

Compound 6-8 (200 mg, 659.69 μmol, 1 eq), 2-(tributylstannyl)furan (235.59 mg, 659.69 μmol, 208.48 μL, 1 eq), [1,1-bis(diphenylphosphino)ferrocene]dichloropalladium (II) (48.27 mg, 65.97 μmol, 0.1 eq) were dissolved in N,N-dimethylformamide (5 mL), and the mixture was stirred at 120° C. for 16 hours. Water (10 mL) and saturated brine (10 mL) were added to the reaction mixture, and the reaction mixture was extracted with ethyl acetate (20 mL). The phases were separated, and the organic phase was dried over anhydrous sodium sulfate, filtered, and the filtrate was concentrated to dryness under reduced pressure to obtain the crude product, which was purified by silica gel column chromatography (gradient eluent: petroleum ether/ethyl acetate=100:0 to 70:30) to obtain compound 20-1.

Characterization of Compound 20-1

LCMS: m/z (ESI)=291.0 $[M+H]^+$.

Step 2: Synthesis of Compound 20-2

Compound 20-1 (145 mg, 499.43 μmol, 1 eq) was dissolved in anhydrous tetrahydrofuran (5 mL), and then tert-butoxy bis(dimethylamino)methane (6.12 g, 35.11 mmol, 7.25 mL, 70.30 eq) was added thereto, and the mixture was stirred at 80° C. for 16 hours under nitrogen atmosphere. After the reaction was completed, the solvent was concentrated to dryness under reduced pressure to obtain compound 20-2.

Characterization of Compound 20-2

LCMS: m/z (ESI)=319.0 $[M-26]^+$.

Step 3: Synthesis of Compound 20-3

Compound 20-2 (170 mg, 492.17 μmol, 1 eq) was dissolved in N,N-dimethylformamide (2 mL), then compound 1-3 (156.17 mg, 492.17 μmol, 1 eq) was added thereto, and the mixture was stirred at 110° C. for 20 hours. After the reaction was completed, the temperature was cooled to 20° C., water (10 mL) and saturated brine (10 mL) were added to the reaction mixture, then the reaction mixture was extracted with ethyl acetate (20 mL). The phases were separated, and the organic phase was dried over anhydrous sodium sulfate, filtered, and the filtrate was concentrated to dryness under reduced pressure to obtain the crude product, which was purified by silica gel column chromatography (gradient elution: dichloromethane/methanol=100:0 to 98:2) to obtain compound 20-3.

Characterization of Compound 20-3

LCMS: m/z (ESI)=600.2 $\mu[M+H]^+$.

$^1H$ NMR (400 MHz, $CDCl_3$) δ: 8.41 (s, 1 H), 8.11-8.13 (m, 1 H), 7.40-7.57 (m, 2 H), 7.23 (s, 1 H), 7.13 -7.16 (m, 1 H), 6.49 -6.52 (m, 1 H), 6.40-6.45 (m, 1 H), 4.39-4.45 (m, 2 H), 3.33 -3.36 (m, 2 H), 3.04-3.16 (m, 4 H), 2.82-2.86 (m, 2 H), 2.44-2.59 (m, 4 H), 2.34 (s, 3 H), 1.42 (t, J=7.2 Hz, 3 H).

Step 4: Synthesis of Compound 20

Compound 20-3 (130 mg, 216.80 μmol, 1 eq) and ammonium chloride (69.58 mg, 1.30 mmol, 6 eq) were dissolved in 1 M solution (1.73 mL, 8 eq) of bis(trimethylsilyl)amino in n-hexane, and the mixture was stirred at 20° C. for 2 hours under nitrogen atmosphere. After methanol (5 mL) was added to the reaction mixture, the solvent was concentrated to dryness under reduced pressure to obtain the crude product, which was purified by HPLC preparative chromatography (HPLC preparation method: Waters 2767/QDa preparative chromatograph; chromatographic column: C18 80*40 mm*3 μm; mobile phase A: 10 mM ammonium bicarbonate aqueous solution, mobile phase B: acetonitrile; running gradient: B %: 25% to 55%, run for 8 min) to obtain compound 20.

Characterization of Compound 20

LCMS: m/z (ESI)=571.2 $[M+H]^+$.

1H NMR (400 MHz, $CDCl_3$) δ: 8.41 (s, 1 H), 8.11 (s, 1 H), 7.45 (s, 2 H), 7.24 (s, 1 H), 7.13 -7.16 (m, 1 H), 6.50 -6.55 (m, 1 H), 6.40 (s, 1 H), 5.66 (s, 2 H), 3.30 -3.36 (m, 2 H), 3.01-3.20 (m, 4 H), 2.82-2.90 (m, 2 H), 2.54-2.60 (m, 4 H), 2.36 (s, 3 H).

Example 21

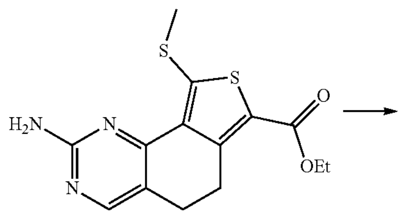

5-4

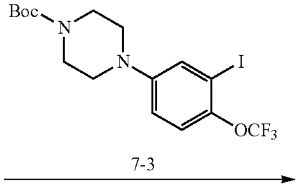

7-3

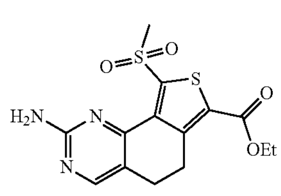

21-1

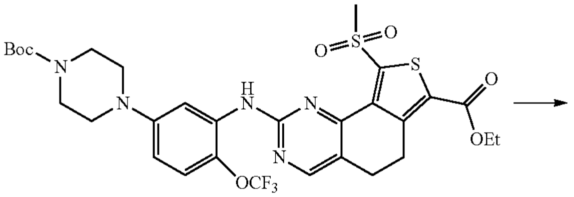

21-2

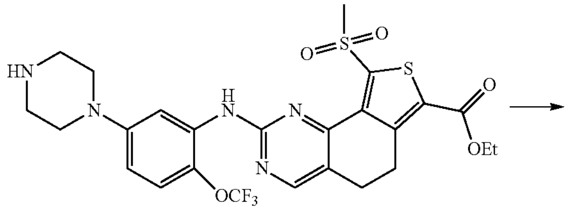

21-3

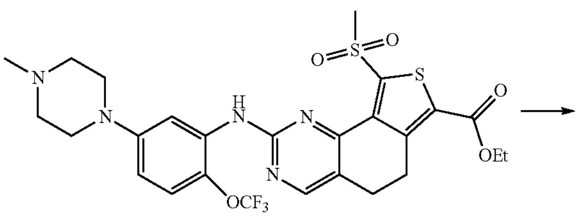

21-4

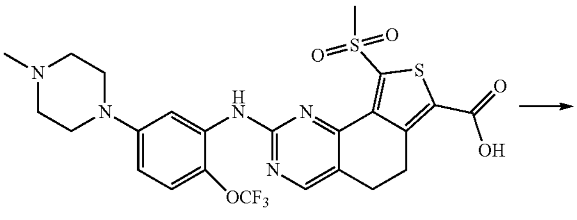

21-5

-continued

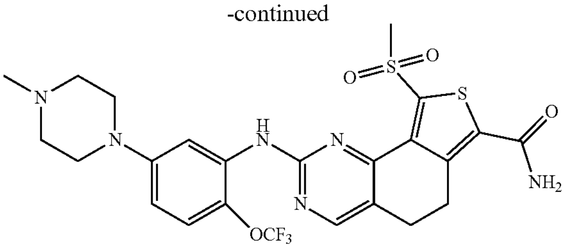

21

Step 1: Synthesis of Compound 21-1

Compound 5-4 (50 mg, 155.56 μmol, 1 eq) was added into anhydrous dichloromethane (2 mL), and the temperature was cooled to 0° C., and then m-chloroperoxybenzoic acid (63.17 mg, 311.12 μmol, 2 eq) with a purity of 85% was added thereto, and the temperature was increased to 25° C. and the mixture was stirred for 12 hours. After the reaction was completed, the reaction mixture was slowly poured into saturated sodium bicarbonate aqueous solution (4 mL), extracted with dichloromethane (4 mL*2), and the organic phases were combined, dried over anhydrous sodium sulfate, filtered, and the filtrate was concentrated under reduced pressure to obtain the crude product, which was purified by silica gel column chromatography (gradient eluent: dichloromethane/methanol=100:0 to 90:10) to obtain compound 21-1.

Characterization of Compound 21-1

LCMS: m/z (ESI)=354.1 $[M+H]^+$.

1H NMR (400 MHz, $CDCl_3$) δ: 8.29 (s, 1H), 5.05 (s, 2H), 4.40 (q, J=7.2 Hz, 2H), 3.76 (s, 3H), 3.33 (t, J=7.2 Hz, 2H), 2.80 (t, J=7.2 Hz, 2H), 1.41 (t, J=7.2 Hz, 3H).

Step 2: Synthesis of Compound 21-2

Compound 21-1 (50 mg, 141.48 μmol, 1 eq) and compound 7-3 (66.81 mg, 141.48 μmol, 1 eq) were added to 1,4-dioxane (2 mL), then tris(dibenzylideneacetone)dipalladium (12.96 mg, 14.15 μmol, 0.1 eq), 4,5-bis(diphenylphosphino)-9,9-dimethylxanthene (8.19 mg, 14.15 μmol, 0.1 eq), and cesium carbonate (92.19 mg, 282.95 μmol, 2 eq) were added thereto, the temperature was raised to 100° C. and the mixture was stirred for 12 hours. After the reaction was completed, the reaction mixture was slowly poured into water (3 mL) to quench, extracted with ethyl acetate (3 mL*3). The organic phases were combined, washed with saturated brine (3 mL*3), dried over anhydrous sodium sulfate, filtered, and the filtrate was concentrated under reduced pressure to obtain the crude product, which was separated by thin-layer chromatography (developing agent: petroleum ether/ethyl acetate=100:100) to obtain compound 21-2.

Characterization of Compound 21-2

LCMS: m/z (ESI)=698.2 $[M+H]^+$.

1H NMR (400 MHz, $CDCl_3$) δ: 8.45 (s, 1H), 7.96-8.04 (m, 1H), 7.14-7.20 (m, 1H), 7.07-7.13 (m, 1H), 6.56-6.65 (m, 1H), 4.34-4.56 (m, 2H), 3.58-3.66 (m, 4H), 3.53-3.57 (m, 3H), 3.32-3.39 (m, 2H), 3.17-3.24 (m, 4H), 2.82-2.90 (m, 2H), 1.47-1.52 (m, 9H), 1.38-1.45 (m, 3H).

Step 3: Synthesis of Trifluoroacetate of Compound 21-3

Compound 21-2 (80 mg, 114.66 μmol, 1 eq) was added to anhydrous dichloromethane (2 mL), then trifluoroacetic acid (273.78 mg, 2.40 mmol, 177.78 μL, 20.94 eq) was added thereto, and the mixture was stirred at 25° C. for 2 hours, and then the reaction mixture was concentrated under reduced pressure to obtain the trifluoroacetate of compound 21-3, and the crude product was directly used in the next step.

Characterization of Compound 21-3

LCMS: m/z (ESI)=598.1 $[M+H]^+$.

Step 4: Synthesis of Compound 21-4

The trifluoroacetate of compound 21-3 (75 mg, 105.39 μmol, 1 eq) was added to anhydrous tetrahydrofuran (1 mL), then triethylamine (10.66 mg, 105.39 μmol, 14.67 μL, 1 eq), formaldehyde aqueous solution (34.21 mg, 421.55 μmol, 31.38 μL, 4 eq) with a purity of 37% and glacial acetic acid (25.32 mg, 421.55 μmol, 24.11 μL, 4 eq) were added thereto, and the mixture was stirred at 25° C. for 0.5 hours, then sodium triacetoxyborohydride (89.34 mg, 421.55 μmol, 4 eq) was added, and the mixture was stirred at 25° C. for 12 hours. Saturated sodium bicarbonate aqueous solution (2 mL) was added to the reaction mixture, and the reaction mixture was extracted with ethyl acetate (2 mL*2), and the phases were separated, dried, filtered, and the filtrate was concentrated under reduced pressure to obtain the crude product, which was purified by thin-layer chromatography (developing agent: dichloromethane/methanol=100:10) to obtain compound 21-4.

Characterization of Compound 21-4

LCMS: m/z (ESI)=612.2 $[M+H]^+$.

1H NMR (400 MHz, $CDCl_3$) δ: 8.41-8.46 (m, 1H), 7.91-7.95 (m, 1H), 7.09-7.18 (m, 2H), 6.55-6.63 (m, 1H), 4.34-4.44 (m, 2H), 3.50-3.56 (m, 3H), 3.30-3.36 (m, 2H), 3.23-3.30 (m, 4H), 2.78-2.89 (m, 2H), 2.59-2.66 (m, 4H), 2.35-2.41 (m, 3H), 1.37-1.43 (m, 3H).

Step 5: Synthesis of Compound 21-5

Compound 21-4 (60 mg, 98.09 μmol, 1 eq) was added to anhydrous tetrahydrofuran (1 mL) and water (1 mL), and then lithium hydroxide monohydrate (12.35 mg, 294.28 μmol, 3 eq) was added thereto, and the mixture was stirred at 25° C. for 12 hours. The reaction mixture was concentrated directly after the reaction was completed, the pH was adjusted to 6 to 7 with 2 N hydrochloric acid, then the mixture was extracted with dichloromethane (3*3 mL). The phases were separated, and the organic phases were combined, dried over anhydrous sodium sulfate, filtered and concentrated to obtain compound 21-5.

Characterization of Compound 21-5

LCMS: m/z (ESI)=584.2 $[M+H]^+$.

Step 6: Synthesis of Compound 21

Compound 21-5 (50 mg, 85.67 μmol, 1 eq) was added to anhydrous N,N-dimethylformamide (0.5 mL), then ammonium bicarbonate (8.80 mg, 111.38 μmol, 9.17 μL, 1.3 eq), O-(7-azabenzotriazol-1-yl)-N,N,N,N-tetramethyluronium hexafluorophosphate (65.15 mg, 171.35 μmol, 2 eq) and N,N-diisopropylethylamine (33.22 mg, 257.02 μmol, 44.77 μL, 3 eq) were added thereto, and the mixture was stirred at 25° C. for 12 hours. After the reaction was completed, the mixture was filtered, and the filtrate was concentrated under reduced pressure to obtain the crude product, which was purified by preparative high performance liquid chromatography (HPLC Preparation: Waters 2767/QDa preparative chromatograph; chromatographic column: C18 80*30 mm*3 μm; mobile phase A: 10 mM ammonium bicarbonate aqueous solution, mobile phase B: acetonitrile; running gradient: B %: 25% to 55%, run for 8 min) to obtain compound 21.

Characterization of Compound 21

LCMS: m/z (ESI)=583.2 $[M+H]^+$.

$^1H$ NMR (400 MHz, DMSO-$d_6$) δ: 8.75-8.84 (m, 1H), 8.44-8.50 (m, 1H), 7.77 -7.99 (m, 2H), 7.18-7.24 (m, 1H), 7.12-7.16 (m, 1H), 6.82-6.87 (m, 1H), 3.30-3.33 (m, 3H), 3.13-3.21 (m, 4H), 3.04-3.11 (m, 2H), 2.71-2.78 (m, 2H), 2.41-2.45 (m, 4H), 2.19 -2.24 (m, 3H).

Examnle 22

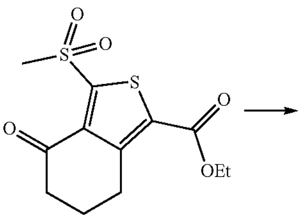

2-1

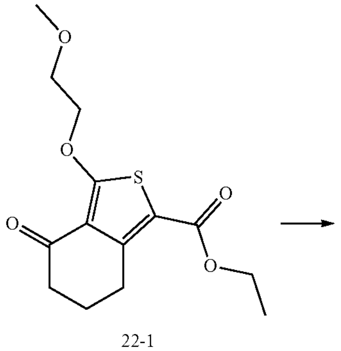

22-1

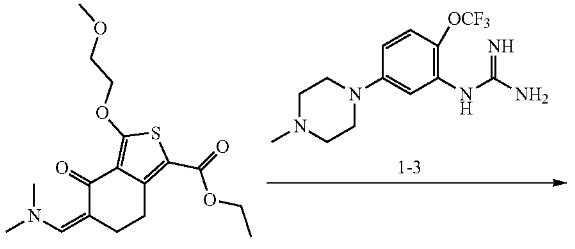

22-2

-continued

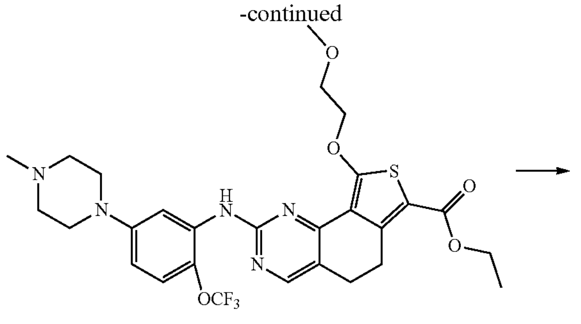

22-3

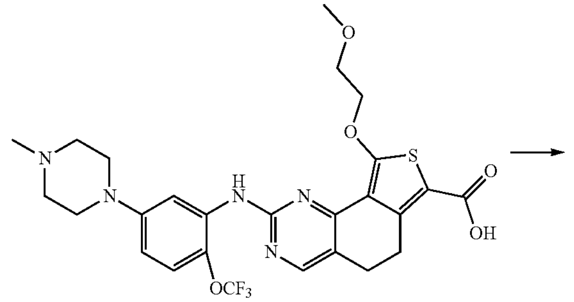

22-4

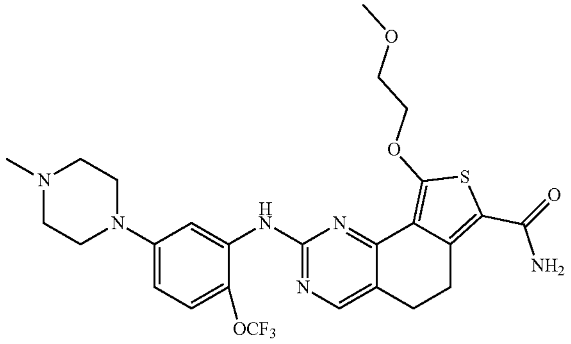

22

Step 1: Synthesis of Compound 22-1

2-Methoxyethanol (151.00 mg, 1.98 mmol, 156.47 μL, 2 eq) was dissolved in tetrahydrofuran solution (5 mL), cooled to 0° C., and sodium hydride (79.37 mg, 1.98 mmol, 2 eq) with purity of 60% was added thereto, and the mixture was reacted at 0° C. for 0.5 hours. Compound 2-1 (300 mg, 992.18 μmol, 1 eq) was added thereto, and the reaction was continued at 0° C. for 0.5 hours. After the reaction was completed, the mixture was added with water (20 mL), extracted with ethyl acetate (10 mL*3), washed with saturated brine (20 mL). The phases were separated, and the organic phase was dried over anhydrous sodium sulfate, filtered, and the filtrate was concentrated under reduced pressure to obtain the crude product, which was separated by column chromatography (gradient eluent: petroleum ether/ethyl methyl acetate=100:0 to 50:50) to obtain compound 22-1.

Characterization of Compound 22-1

LCMS: m/z (ESI)=298.9 $[M+H]^+$.

1H NMR (400 MHz, $CDCl_3$) δ: 1.38 (t, J=7.09 Hz, 3 H), 1.98-2.08 (m, 2 H), 2.42 -2.58 (m, 2 H), 3.19-3.23 (m, 2 H), 3.46-3.55 (m, 3 H), 3.81-3.95 (m, 2 H), 4.33 (q, J=7.09 Hz, 2 H), 4.38-4.42 (m, 2 H).

Step 2: Synthesis of Compound 22-2

Compound 22-1 (100 mg, 335.17 μmol, 1 eq) was dissolved in toluene (3 mL), and tert-butoxy bis(dimethylamino)methane (350.49 mg, 2.01 mmol, 415.27 μL, 6 eq) was added, and the mixture was stirred at 90° C. for 12 hours. After the reaction was completed, saturated ammonium chloride aqueous solution (5 mL) was added, then the mixture was extracted with ethyl acetate (3 mL*3). The phases were separated, and the organic phase was washed with saturated sodium chloride aqueous solution (5 mL), dried over anhydrous sodium sulfate, filtered, and the filtrate was concentrated under reduced pressure to obtain compound 22-2.

Characterization of Compound 22-2

LCMS: m/z (ESI)=327.0 $[M-26]^+$.

Step 3: Synthesis of Compound 22-3

Compound 22-2 (200 mg, 565.88 μmol, 1 eq) and compound 1-3 (179.56 mg, 565.88 pmol, 1 eq) were dissolved in N,N-dimethylformamide (2 mL), and the mixture was stirred at 110° C. 12 hours. After the reaction was completed, water (5 mL) was added to quench the reaction, then the mixture was extracted with ethyl acetate (5 mL*3), and the organic phases were combined, washed with saturated sodium chloride solution (5 mL), dried over anhydrous sodium sulfate, filtered, and the filtrate was concentrated under reduced pressure to obtain the crude product, which was purified by HPLC preparative chromatography (HPLC preparation method: Waters Xbridge Prep OBD preparative chromatograph; chromatographic column: C18 150*40 mm*10 μm; mobile phase A: 10 mM ammonium bicarbonate aqueous solution (containing 0.05% ammonia water), mobile phase B: acetonitrile; gradient B %: 50% to 80%, 8 min) to obtain compound 22-3.

Characterization of Compound 22-3

LCMS: m/z (ESI)=608.3 $[M+H]^+$.

1H NMR (400 MHz, $CD_3OD$) δ: 1.38 (t, J=7.13 Hz, 3 H), 2.37 (s, 3 H), 2.59-2.68 (m, 4 H), 2.80-2.82 (m, 2 H), 3.24-3.31 (m, 9 H), 3.75-3.80 (m, 2 H), 4.33 (q, J=7.13 Hz, 2 H), 4.41-4.50 (m, 2 H), 6.60-6.70 (m J=9.07, 1 H), 7.15-7.23 (m, 1 H), 8.20-8.24 (m, 1 H), 8.32 (s, 1 H).

Step 4: Synthesis of Compound 22-4

Compound 22-3 (40 mg, 65.83 μmol, 1 eq) was dissolved in a mixed solvent of tetrahydrofuran (1 mL), methanol (0.25 mL) and water (0.25 mL), and lithium hydroxide monohydrate (13.81 mg, 329.14 μmol, 5 eq) was added thereto, and the mixture was stirred at 40° C. for 12 hours, then concentrated under reduced pressure to remove most of the solvent after the reaction was completed, and the pH was adjusted to 6 to 7 with 2 N hydrochloric acid, and then the mixture was extracted with ethyl acetate (2 mL*3). The organic phases were combined, dried over anhydrous sodium sulfate, filtered, and the filtrate was concentrated under reduced pressure to obtain compound 22-4.

Characterization of Compound 22-4

LCMS: m/z (ESI)=580.1 [M+H]+.

Step 5: Synthesis of Compound 22

Compound 22-4 (35 mg, 60.39 μmol, 1 eq) was dissolved in N,N-dimethylformamide (2 mL), and then N,N-diisopropylethylamine (78.05 mg, 603.88 μmol, 105.18 μL, 10 eq), 0-(7-azabenzotriazol-1-yl)-N,N,N,N-tetramethyluronium hexafluorophosphate (137.77 mg, 362.33 μmol, 6 eq), and ammonium bicarbonate (47.74 mg, 603.88 μmol, 49.73 μL, 10 eq) were added thereto sequentially, and the mixture was stirred at 20° C. for 12 hours. After the reaction was completed, saturated ammonium chloride aqueous solution (2 mL) was added, and the mixture was extracted with ethyl acetate (2 mL*3). The organic phases were combined, washed with saturated brine (3 mL), dried over anhydrous sodium sulfate, filtered, and the filtrate was concentrated to dryness under reduced pressure to obtain the crude product, which was purified by HPLC preparative chromatography (HPLC preparation method: Phenomenex preparative chromatography; columns: C18 75*30 mm*3 μm; mobile phase A: 10 mM ammonium bicarbonate aqueous solution (containing 0.05% ammonia), mobile phase B: acetonitrile; running gradient: B %: 30% to 55%, run for 8 min) to obtain compound 22.

Characterization of Compound 22

LCMS: m/z (ESI)=579.1 [M+H]+.

1H NMR (400 MHz, DMSO-$d_6$) δ: 2.25 (s, 3 H), 2.71 (s, 2 H), 3.00-3.24 (m, 9 H), 3.35 (s, 4 H), 3.59 (s, 2 H), 4.26 (s, 2 H), 6.60-6.70 (m, 1 H), 7.15-7.20 (m, 1 H), 7.38 (s, 2 H), 7.80 (s, 1 H), 8.21 (s, 1 H), 8.34 (s, 1 H).

Example 23

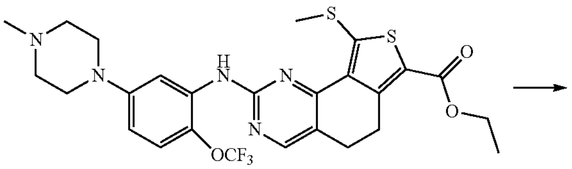

1-4

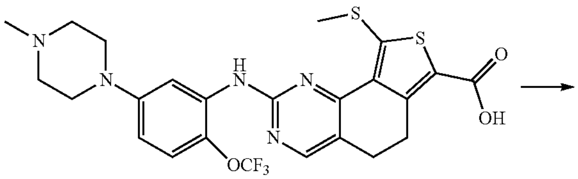

23-1

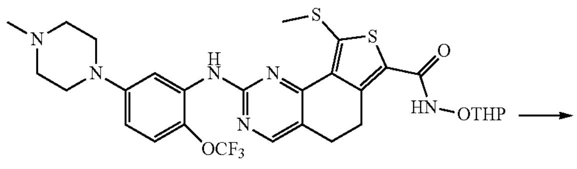

23-2

-continued

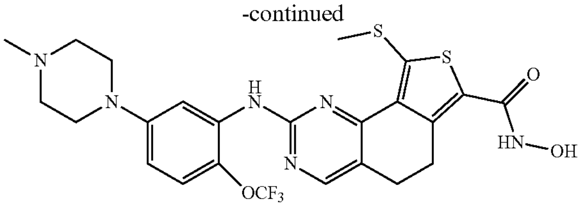

23

Step 1: Synthesis of Compound 23-1

Compound 1-4 (14 g, 24.15 mmol, 1 eq) was added to a mixture of water (140 mL), tetrahydrofuran (70 mL) and methanol (70 mL), and lithium hydroxide monohydrate (3.04 g, 72.46 mmol, 3 eq) was added thereto, and the mixture was stirred at 25° C. for 12 hours. After the reaction was completed, the reaction mixture was concentrated to ½ of the original volume, and 2-methyltetrahydrofuran (30 ml) was added thereto, then pH was adjusted to 6 to 7 with 6N hydrochloric acid, and the mixture was stirred at 20° C. for 2 hours, then filtered, and then dried to obtain compound 23-1.

LCMS: m/z (ESI)=552.1 [M+H]+.

Step 2: Synthesis of Compound 23-2

Compound 23-1 (50 mg, 90.64 μmol, 1 eq) was dissolved in N,N-dimethylformamide (2 mL), and O-(7-azabenzotriazol-1-yl)-N,N,N,N-tetramethyluronium hexafluorophosphate (68.93 mg, 181.29 μmol, 2 eq), N,N-diisopropylethylamine (35.14 mg, 271.93 μmol, 47.36 μL, 3 eq) were added thereto, and the mixture was stirred at 20° C. for 0.5 hours, then O-(tetrahydro-2H-pyran)-2-hydroxylamine (21.24 mg, 181.29 μmol, 2 eq) was added thereto, the stirring was continued for 1 hour at 20° C. Then water (3 mL) was added to the reaction system after the reaction was completed, then the mixture was filtered, and the obtained filter cake was dried to obtain compound 23-2.

Characterization of Compound 23-2

LCMS: m/z (ESI)=651.0 [M+H]+.

Step 3: Synthesis of Compound 23

Compound 23-2 (50 mg, 76.84 μmol, 1 eq) was dissolved in anhydrous methanol (5 mL), p-toluenesulfonic acid (35.71 mg, 207.40 μmol, 2.70 eq) was added thereto, and the reaction was stirred at 20° C. for 1 hour. After the reaction was completed, the reaction system was concentrated under reduced pressure, then water (5 mL) was added thereto, and the mixture was extracted with ethyl acetate (5 mL*3). The phases were separated, and the combined organic phases were dried over anhydrous sodium sulfate, filtered, and the filtrate was concentrated under reduced pressure to obtain the crude product. The crude product was purified by HPLC preparative chromatography (HPLC preparation method: Phenomenex Luna preparative chromatograph; chromatographic column: C18 75*30 mm*3 μm; mobile phase A: Water (containing 0.05% formic acid), mobile phase B: acetonitrile; running gradient: B %: 20% to 60%, run for 8 min) to obtain the formate of compound 23.

Characterization of Compound 23

LCMS: m/z (ESI)=567.1 $[M+H]^+$.

$^1$H NMR (400 MHz, DMSO-$d_6$) δ: 10.53-10.85 (m, 1 H), 8.93-9.36 (m, 1 H), 8.47 (s, 1 H), 8.32 (s, 1 H), 8.16 (s, 1 H), 7.50 (d, J=2.8 Hz, 1 H), 7.17 (dd, J=8.8, 1.6 Hz, 1 H), 6.71 (dd, J=9.2, 2.8 Hz, 1 H), 3.12-3.18 (m, 4 H), 3.07-3.10 (m, 2 H), 2.73 (t, J=7.2 Hz, 2 H), 2.53 (s, 3 H), 2.43-2.46 (m, 4 H), 2.22 (s, 3 H).

Biological Test Data

Test Example 1: Evaluation of PLK1 Kinase Activity In Vitro

The $^{33}$P isotope-labeled kinase activity assay (Reaction Biology Corp) was used to determine the IC50 value to evaluate the inhibitory ability of the test compound to human PLK1 protein kinase.

Buffer conditions: 20 mM HEPES (pH 7.5), 10 mM $MgCl_2$, 1 mM EGTA, 0.01% Brij35, 0.02 mg/ml BSA, 0.1 mM $Na_3VO_4$, 2 mM DTT, 1% DMSO Test steps: At room temperature, the compounds to be tested were dissolved in DMSO to prepare a 10 mM solution for use. The substrate Casein was dissolved in a freshly prepared buffer (with a final concentration of 20 μM), and the tested PLK1 kinase (with a final concentration of 12 nM) was added thereto and mixed well. The acoustic wave pipetting system Echo 550 was used to add the mother solution of the test compound dissolved in DMSO to the above mixed reaction mixture according to the set final concentration gradient (the highest final concentration was 1 μM, 3-fold dilution, 10 gradients). After incubation at room temperature for 20 minutes, $^{33}$P-ATP (30 μM) was added, and after incubation at room temperature for 120 minutes, the reaction mixture was spotted on P81 ion exchange filter paper (Whatman #3698-915). After the filter paper was repeatedly washed with 0.75% phosphoric acid solution, the radioactivity of the phosphorylated substrate remaining on the filter paper was measured. % Kinase activity=kinase activity $_{test\ compound}$/kinase activity $_{blank\ group\ (DMSO)}$×100%, the $IC_{50}$ value was obtained by curve fitting with Prism4 software (GraphPad), and the experimental results are shown in Table 1.

TABLE 1

PLK1 kinase activity screening test results of compounds of the present disclosure in vitro

| Compound number | PLK1/$IC_{50}$(nM) |
|---|---|
| 1 | 4.4 |
| 2 | 4.2 |
| 3 | 5.0 |
| 4 | 1.0 |
| 5 | 2.6 |
| 6 | 6.9 |
| 7 | 3.0 |
| 8 | 1.7 |
| 12 | 4.0 |
| 13 | 4.9 |
| 14 | 7.3 |
| 15 | 6.4 |
| 16 | 5.3 |
| 17 | 5.9 |
| 18 | 4.3 |
| 20 | 2.8 |

Conclusion: The compounds of the present disclosure generally exhibit better inhibitory activity against PLK1.

Test Example 2: Evaluation of PLK2/PLK3/PLK4 Kinase Activity In Vitro

The $^{33}$P isotope-labeled kinase activity test (Reaction Biology Corp) was used to determine the $IC_{50}$ value to evaluate the inhibitory ability of the test compound to the human PLK family protein kinase PLK2/PLK3/PLK4.

Buffer conditions: 20 mM HEPES (pH 7.5), 10 mM $MgC_2$, 1 mM EGTA, 0.01% Brij35, 0.02 mg/ml BSA, 0.1 mM $Na_3VO_4$, 2 mM DTT, 1% DMSO.

Test steps: At room temperature, the compounds to be tested were dissolved in DMSO to prepare a 10 mM solution for use. The substrate Casein was dissolved in the freshly prepared buffer (with a final concentration of 20 μM), and the tested PLK2/PLK3/PLK4 kinases (with a final concentration of 15/10/150 nM, respectively) were added thereto and mixed well. The acoustic wave pipetting system Echo 550 was used to add the mother solution of the test compound dissolved in DMSO to the above mixed reaction mixture according to the set final concentration gradient (the highest final concentration was 1 μM, 3-fold dilution, 10 gradients). After incubation at room temperature for 20 minutes, $^{33}$P-ATP (with a final concentration of 30/50/10 μM, respectively) was added, then after incubation at room temperature for 120 minutes, the reaction mixture was spotted on P81 ion exchange filter paper (Whatman #3698-915). After the filter paper was repeatedly washed with 0.75% phosphoric acid solution, the radioactivity of the phosphorylated substrate remaining on the filter paper was measured. % Kinase activity=kinase activity$_{test\ compound}$/kinase activity$_{blank\ group\ (DMSO)}$×100%, the $IC_{50}$ value was obtained by curve fitting with Prism4 software (GraphPad), and the experimental results are shown in Table 2.

TABLE 2

Results of selectivity test of the present disclosure over PLK family protein kinases

| | Compound 1 |
|---|---|
| PLK2 $IC_{50}$ (μM) | >10 |
| PLK3 $IC_{50}$ (μM) | >10 |
| PLK4 $IC_{50}$ (μM) | >10 |

Conclusion: The compounds of the present disclosure have weak inhibitory activity against PLK2/PLK3/PLK4 kinases, that is, they have better PLK1 selectivity.

Test Example 3: Evaluation of HCT116 Cytological Activity In Vitro

Experimental Materials:

McCoy's 5A medium, penicillin/streptomycin antibiotics was purchased from Vicente, and fetal bovine serum was purchased from Biosera. 3D CellTiter-Glo (cell viability chemiluminescence assay reagent) reagent was purchased from Promega. HCT116 cell line was purchased from Nanjing Cobioer Biosciences Co., Ltd. Envision multimode microplate reader (PerkinElmer).

Experimental Methods:

HCT116 cells were seeded in ultra-low adsorption 96-well U-plates, 80 μL of cell suspension per well, which contained 1000 HCT116 cells. Cell plates were cultured overnight in a carbon dioxide incubator.

The compound to be tested was 5-fold diluted to the 9th concentration with a pipette, that is, diluted from 2 mM to 5.12 nM, and a double-well experiment was set up. 78 μL of medium was added to the intermediate plate, and then 2 μL of each well of the gradient diluted compound was transferred to the intermediate plate according to the corresponding position, 20 μL of each well was transferred to the cell plate after mixing well. Compound concentrations transferred to cell plates ranged from 10 μM to 0.0256 nM. Cell plates were cultured in a carbon dioxide incubator for 5 days. Another cell plate was prepared, and the signal value was read as the maximum value (Max value in the following equation) on the day of drug addition to participate in data analysis.

Every 100 μL of cell viability chemiluminescent detection reagent was added to the cell plate, and incubated at room temperature for 10 minutes to stabilize the luminescent signal. A multimode microplate reader was used to read.

Data Analysis:

The equation (Sample−Min)/(Max−Min)*100% was used to convert the original data into an inhibition rate, and the value of $IC_{50}$ can be obtained by curve fitting with four parameters ("log(inhibitor) vs. response in GraphPad Prism—Variable slope" mode). Table 3 provides the inhibitory activity of the compounds of the present disclosure against the proliferation of HCT116 cells.

TABLE 3

In vitro screening test results of compounds of the present disclosure

| Compound number | HCT116/$IC_{50}$(nM) |
|---|---|
| 1 | 27 |
| 2 | 30.8 |
| 4 | 35 |
| 8 | 52 |
| 16 | 29.2 |
| 17 | 18.3 |
| 18 | 74.5 |
| 20 | 58.6 |
| 23 | 72 |

Conclusion: the compound of the present disclosure exhibits better inhibitory activity against cell proliferation in HCT116 cell line.

Test Example 4: Pharmacokinetic Study of Test Compound in CD-1 Male Mice by Oral Administration and Intravenous Injection Purpose of the Experiment:

The purpose of this experiment is to study the pharmacokinetics of the test compound in the plasma of CD-1 male mice after intravenous injection and oral administration.

Experimental Operation:

Intravenous injection group: an appropriate amount of the test compound was weighed and dissolved in 20% SBE-b-CD aqueous solution and the pH was adjusted to 4 to 5 with 6 M hydrochloric acid, and the mixture was vortexed for 2, minutes to obtain a clear solution, and then pH was adjusted around 7 with 5 N sodium hydroxide, and the mixture was vortexed for 1 minute to prepare a 1.5 mg/mL clear solution, which was filtered through a 0.22 μm microporous membrane for later use. CD-1 male mice from 6 to 10 weeks old were selected and given a solution of the test compound intravenously. Samples were collected at 0.083, 0.25, 0.5, 1, 2, 4, 6, 8, and 24 hours.

Oral administration group: an appropriate amount of the test compound was weighed and dissolved in 20% SBE-b-CD aqueous solution, and the pH was adjusted to 3 to 4 with 6 M hydrochloric acid, and the mixture was vortexed for 2, minutes to obtain a clear solution, and then pH was adjusted around 7 with 5 N sodium hydroxide, and mixture was vortexed for 1 minute to prepare a 2.0 mg/mL clear solution for later use. CD-1 male mice between 6 and 10 weeks of age were selected and given the test compounds orally. Samples were collected at 0.25, 0.5, 1, 2, 4, 6, 8, 10, and 24 hours.

Approximately 50 μL of whole blood was collected through the jugular vein at each time point for plasma preparation for concentration determination by high performance liquid chromatography-tandem mass spectrometry (LC-MS/MS). All animals were euthanized under $CO_2$ anesthesia after collecting the PK samples at the last time point. The plasma concentration was processed using the non-compartmental model of WinNonlin™ Version 6.3 (Pharsight, Mountain View, CA) pharmacokinetic software, and the pharmacokinetic parameters were calculated using the linear logarithmic trapezoidal method, and the experimental results are shown in Table 4.

TABLE 4

Pharmacokinetic results of the tested compounds

| | Pharmacokinetic parameters | Compound 1 | Compound 2 | Compound 8 | Compound 18 |
|---|---|---|---|---|---|
| IV | Dose (mg/kg) | 0.5 | 1.0 | 0.5 | 1.1 |
| | Half-life T½ (h) | 1.47 | 1.15 | 0.74 | 1.22 |
| | Clearance CL (ml/min/kg) | 37.8 | 47.9 | 37.4 | 31.4 |
| | Apparent volume of distribution Vdss (L/kg) | 3.37 | 2.89 | 2.04 | 2.38 |
| | Area under the plasma concentration-time curve $AUC_{0-24\ h}$ (nM · h) | 410 | 624 | 374 | 940 |
| PO | Dose (mg/kg) | 2.0 | 3.0 | 2.2 | 3.4 |
| | Peak time Tmax (h) | 0.75 | 0.75 | 0.75 | 1.00 |
| | Peak concentration Cmax (nM) | 386 | 478 | 157 | 688 |
| | Area under the plasma concentration-time curve $AUC_{0-24\ h}$ (nM · h) | 1051 | 1018 | 459 | 2129 |
| | Bioavailability F (%) | 66.4 | 54.2 | 30.9 | 82.5 |

Experimental Results:

The pharmacokinetic study of the compound in CD-1 mice showed a low drug clearance rate, and after oral administration, it could reach the peak quickly and presented a high oral absorption bioavailability.

Test Example 5: In vivo Pharmacodynamic Study of the Test Compound on the Subcutaneous Xenograft Tumor Model of Human Colon Cancer HCT116 Cells 1. Experimental Purpose In this experiment, human colon cancer HCT116 cells were subcutaneously transplanted into BALB/c Nude mouse model to evaluate the antitumor effect of the test compound in vivo.

2. Experimental Method 2.1 Model Establishment

HCT116 cell culture: 10% fetal calf serum was added to McCoy's 5A medium and cultured in 37° C. 5% CO2 cell incubator. When the cell saturation reached 80% to 90% and the number reached the requirement, cells were collected, counted and inoculated subcutaneously into BALB/c Nude mice (female, 6 to 7 weeks old)

2.2 Grouping and Administration Observation

When the tumors grew to a certain size, the animals with tumor volumes that were too large, too small, or with irregular tumor shapes were eliminated, and animals with tumor volumes ranging from 103.12 to 174.35 $mm^3$ were selected. According to the tumor volume, the animals were divided into 6 groups by random block method, and each group was composed of 6 mice wherein the average volume of the tumor was about 147.12 $mm^3$ , and the experimental grouping and dosing regimen were shown in Table 5 below. The health status and death of the animals were monitored every day. Routine inspections included observation of tumor growth and the effects of drug treatment on the daily behavior of the animals, such as behavioral activities, food and water intake, body weight changes (measured twice a week), tumor size (tumor volume was measured twice a week), appearance signs or other abnormal conditions.

TABLE 5

Research protocol of human colon cancer HCT116 cell BALB/c Nude mouse xenograft tumor model

| Group | Test compound | Number of animals | Administration dose (mg/kg) | Route of administration | Frequency of administration |
|---|---|---|---|---|---|
| 1 | Vehicle | 6 | / | PO | QD |
| 2 | Compound 1 | 6 | 30 | PO | QD |
| 3 | Compound 1 | 6 | 45 | PO | QD |
| 4 | Compound 2 | 6 | 60 | PO | QD |
| 5 | Compound 8 | 6 | 60 | PO | QD |

Solvent: i.e. Vehicle group, 20% SEB-β-CD
PO: oral administration
QD: Once a day, give for 5 days and stop for 2 days 2.3 Evaluation Indicators The formula for calculating tumor volume (TV) was: $\frac{1}{2} \times a \times b^2$, where a and b were the measured length and width of the tumor, respectively. The formula for calculating the tumor inhibition rate TGI (%) was: TGI (%)=[1−(average tumor volume at the end of administration of a certain treatment group−average tumor volume at the beginning of administration of this treatment group)/(average tumor volume at the end of treatment of the solvent control group−average tumor volume at the beginning of treatment in solvent control group)]×100%.

2.4 Data Analysis

In this study, the experimental data were expressed as Mean±SEM. Statistical analysis was based on the data of RTV at the end of the experiment using IBM SPSS Statistics software. The comparison between two groups was analyzed by T test, and the comparison between three or more groups was analyzed by one-way ANOVA. If the variances were homogeneous (the F value had no significant difference), the Tukey's method was used for analysis. If the variances were not homogeneous (the F value had significant differences), and the Games-Howell method was used for testing. $p<0.05$ was considered as a significant difference.

3. Experimental Results and Discussion

Figure 2:
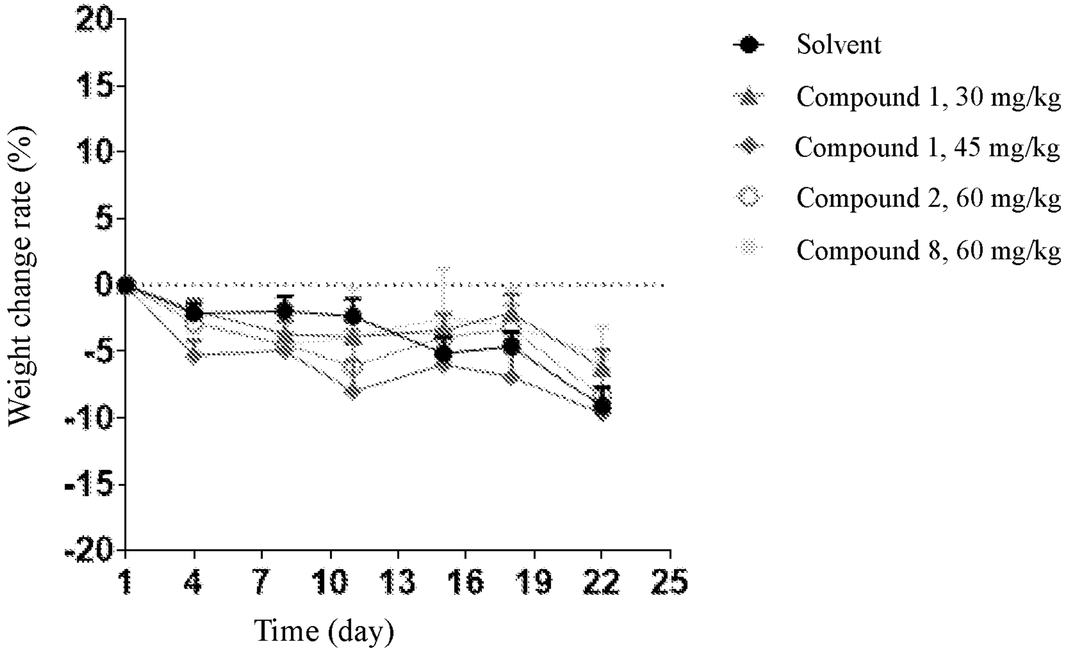
FIG. 2. Body weight change diagram of in vivo pharmacodynamic study of human colon cancer HCT-116 cell subcutaneous xenograft tumor model.

In this experiment, the drug efficacy of test compound 1, compound 2 and compound 8 in human colon cancer HCT-116 cells subcutaneously transplanted tumor BALB/c Nude mouse model was evaluated. In this experiment, no animal death occurred in all experimental groups during the whole administration period, and the mice were well tolerated. The experimental results are shown in Table 6, FIG. 1, and FIG. 2.

TABLE 6

Antitumor efficacy evaluation of test compounds on the subcutaneous xenograft tumor model of human colon cancer HCT116 cells (calculated based on tumor volume on day 22 after dosing)

| Test compound | Administration dose (mg/kg) | TGI |
|---|---|---|
| Vehicle | / | — |
| Compound 1 | 30 | 72.9% |
| Compound 1 | 45 | 87.3% |
| Compound 2 | 60 | 72.5% |
| Compound 8 | 60 | 85.4% |

Experimental conclusion: In this pharmacodynamic model, the compounds of the present disclosure exhibited a dose-dependent antitumor activity, and had a significant antitumor activity, and during the whole experiment, the body weight change of the animals was close to that of the vehicle group, and the animal tolerance was good.

What is claimed is:

1. A compound of formula (P) or a pharmaceutically acceptable salt thereof, (P)

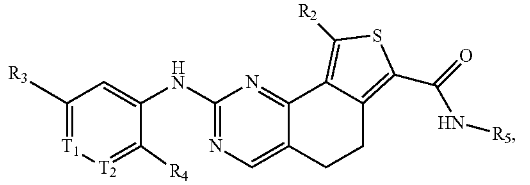

wherein $T_1$ is selected from $CR_1$ and N;

$T_2$ is selected from CH and N;

$R_1$ is selected from H;

$R_2$ is selected from H, CN, $C_{1-3}$ alkyl, $C_{1-3}$ alkoxy, $C_{1-3}$ alkylthiol, $S(=O)_2C_{1-3}$ alkyl, $C_{2-3}$ alkynyl, $C_{3-5}$ cycloalkyl, —O—$C_{3-5}$ cycloalkyl, and 5-membered heteroaryl, and the $C_{1-3}$ alkyl, $C_{1-3}$ alkoxy, $C_{1-3}$ alkylthiol, $S(=O)_2C_{1-3}$ alkyl, $C_{2-3}$ alkynyl, $C_{3-5}$ cycloalkyl, —O—$C_{3-5}$ cycloalkyl, and 5-membered heteroaryl are optionally substituted by 1, 2, or 3 $R_b$;

$R_3$ is selected from $C_{1-4}$ alkyl, piperazinyl, and 7- to 9-membered heterocycloalkyl, and the $C_{1-4}$ alkyl, piperazinyl, and 7- to 9-membered heterocycloalkyl are optionally substituted by 1, 2, or 3 $R_c$;

$R_4$ is selected from $C_{1-3}$ alkyl and $C_{1-3}$ alkoxy, and the $C_{1-3}$ alkyl and $C_{1-3}$ alkoxy are optionally substituted by 1, 2, or 3 $R_d$;

$R_5$ is selected from H and OH;

or, $R_1$ and $R_3$ together with the atom to which they are attached form a ring, so that the structural moiety

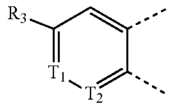

is selected from

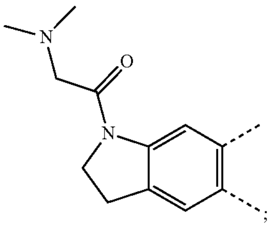

each $R_b$ is independently selected from F, Cl, Br, I, OH, and $OCH_3$;

each $R_c$ is independently selected from =O, $C_{1-3}$ alkyl, $C_{1-4}$ alkylamino, and heterocyclobutyl, and the $C_{1-3}$ alkyl, $C_{1-4}$ alkylamino, and heterocyclobutyl are optionally substituted by 1, 2, or 3 R;

each Rd is independently selected from F, Cl, Br, and I;

each R is independently selected from F, Cl, Br, I, and OH;

heteroatoms of the "heterocyclobutyl" and "7- to 9-membered heterocycloalkyl" are selected from N, O, and S.

2. The compound or the pharmaceutically acceptable salt thereof according to claim 1, wherein $R_2$ is selected from H, CN, $SCH_3$, $SCH_2CH_3$, $SCH(CH_3)_2$, $S(=O)_2CH_3$, $OCH_3$, $OCH_2CH_3$, $OCH(CH_3)_2$, $CH_3$, $CH_2CH_3$, $CH(CH_3)_2$, cyclopropyl,

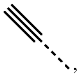, 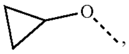, and 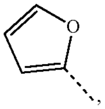, and the $SCH_3$, $SCH_2CH_3$, $SCH(CH_3)_2$, $S(=O)_2CH_3$, $OCH_3$, $OCH_2CH_3$, $OCH(CH_3)_2$, $CH_3$, $CH_2CH_3$, $CH(CH_3)_2$, cyclopropyl,

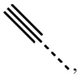, 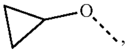, and 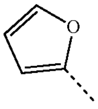

are optionally substituted by 1, 2, or 3 $R_b$.

3. The compound or the pharmaceutically acceptable salt thereof according to claim 2, wherein $R_2$ is selected from H, CN, $SCH_3$, $SCH_2CH_2OH$, $S(=O)_2CH_3$, $OCH_2CH_3$, $OCH_2CH_2OH$, $OCH_2CH_2OCH_3$, $CH_3$, $CH_2CH_2OH$, $CH_2OCH_3$, cyclopropyl,

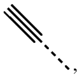, 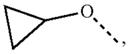, and 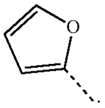.

4. The compound or the pharmaceutically acceptable salt thereof according to claim 1, wherein $R_c$ is selected from =O, $CH_3$, $CH_2CH_3$, $N(CH_3)_2$, and

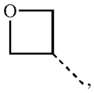, and the $CH_3$, $CH_2CH_3$, and $N(CH_3)_2$ are optionally substituted by 1, 2, or 3 R.

5. The compound or the pharmaceutically acceptable salt thereof according to claim 4, wherein $R_c$ is selected from =O, $CH_3$, $CH_2CH_2OH$, $N(CH_3)_2$, and

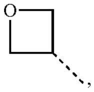,

6. The compound or the pharmaceutically acceptable salt thereof according to claim 1, wherein $R_3$ is selected from $CH_2CH_2CH_3$,

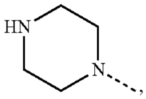, 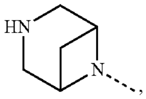, 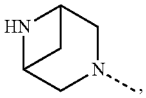, and 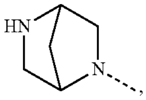, and the $CH_2CH_2CH_3$,

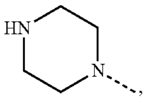, 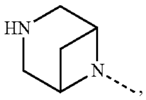, 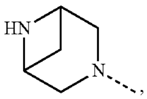, and 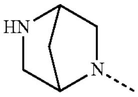

are optionally substituted by 1, 2, or 3 $R_c$.

7. The compound or the pharmaceutically acceptable salt thereof according to claim 1, wherein $R_3$ is selected from

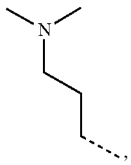, 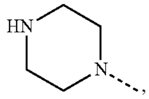, 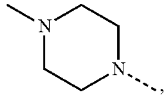, 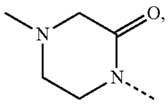

-continued

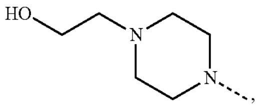

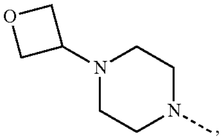

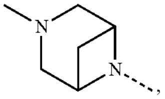

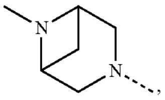

and

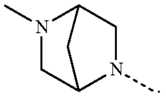

8. The compound or the pharmaceutically acceptable salt thereof according to claim 1, wherein $R_4$ is selected from $CH_3$, $OCH_3$, $OCHF_2$, and $OCF_3$.

9. The compound or the pharmaceutically acceptable salt thereof according to claim 1, wherein the compound is selected from (P-1)

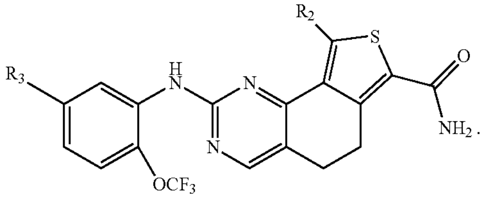

10. A compound shown below or a pharmaceutically acceptable salt thereof, wherein the compound is selected from

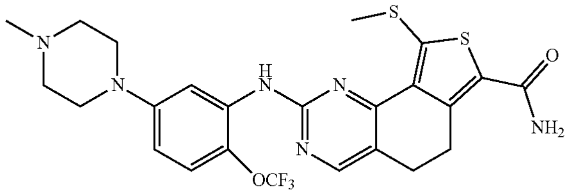

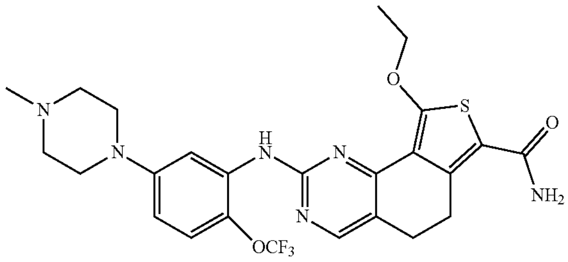

-continued

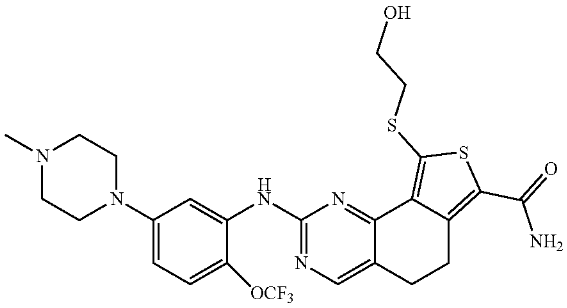

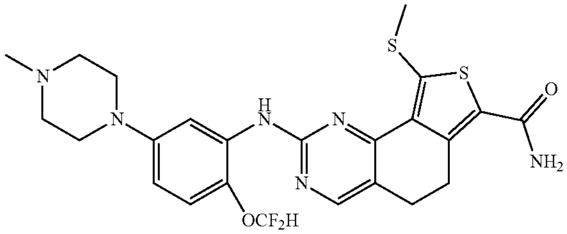

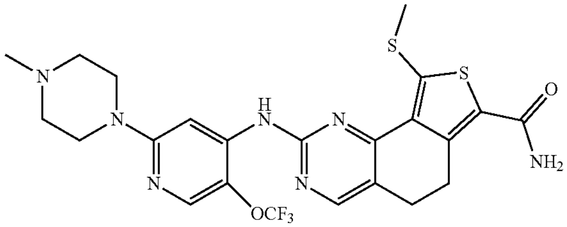

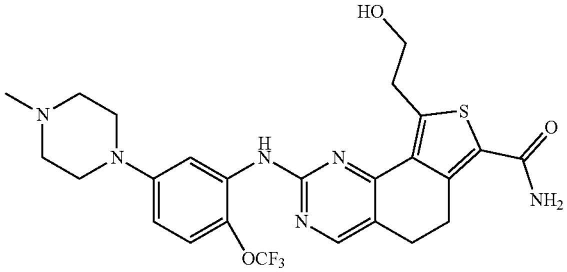

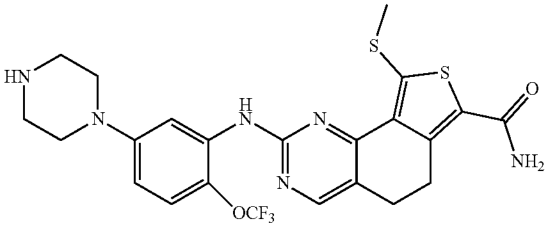

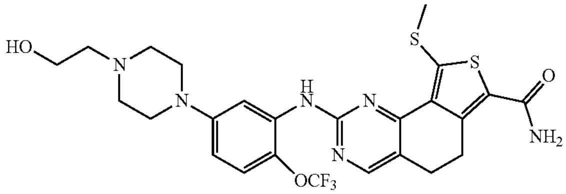

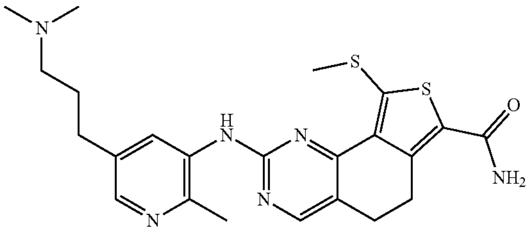

-continued
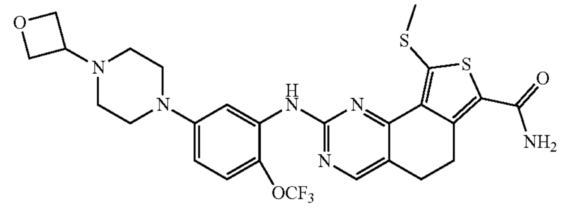
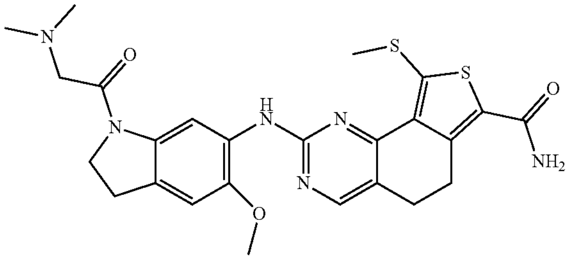
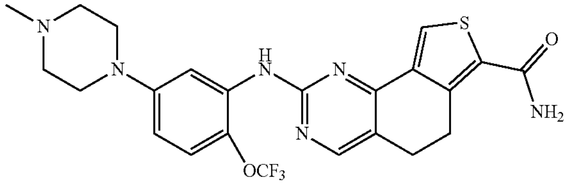
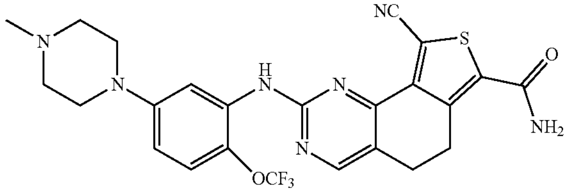
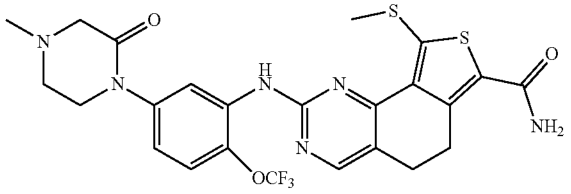
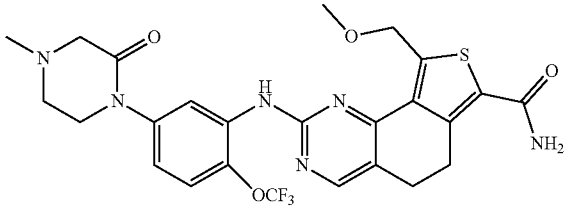
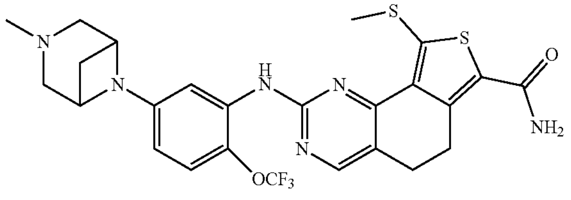
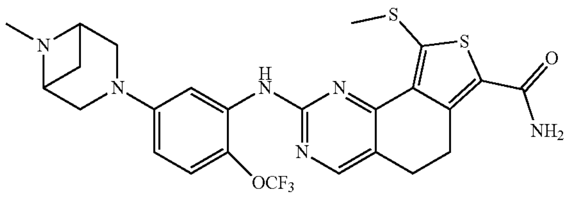
-continued
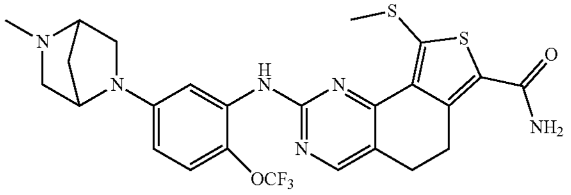
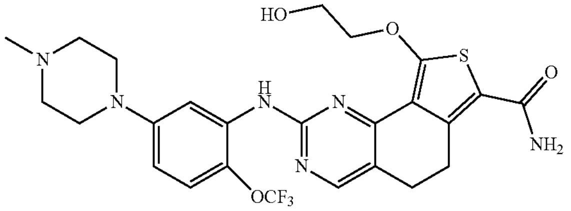
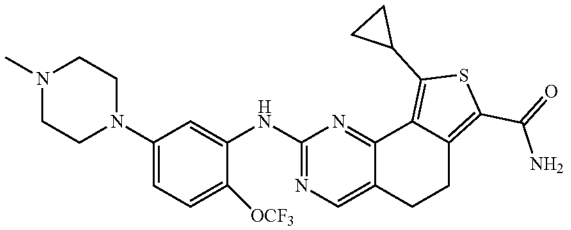
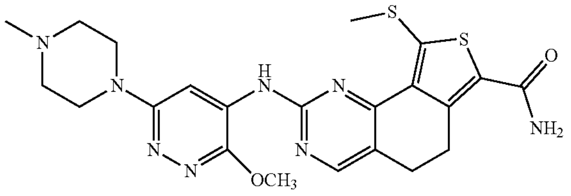
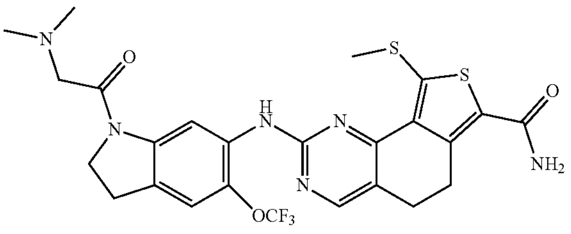
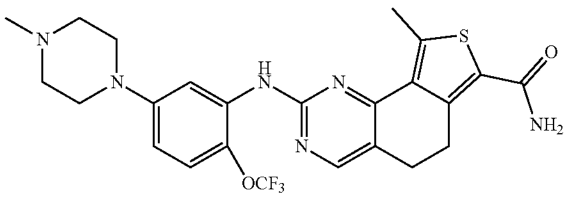
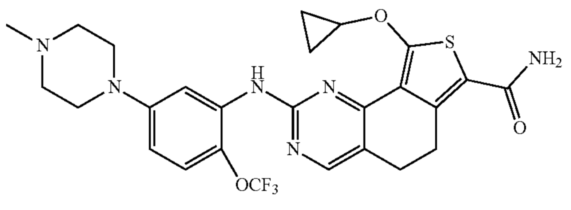

-continued

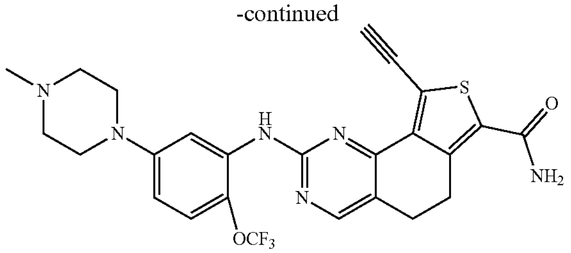

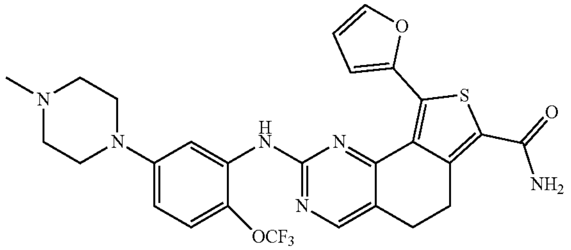

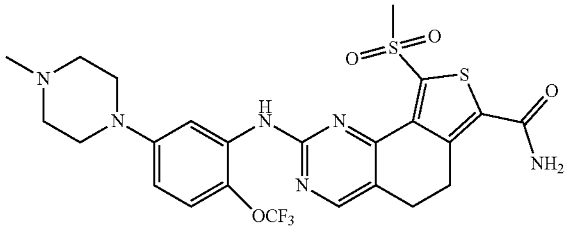

-continued

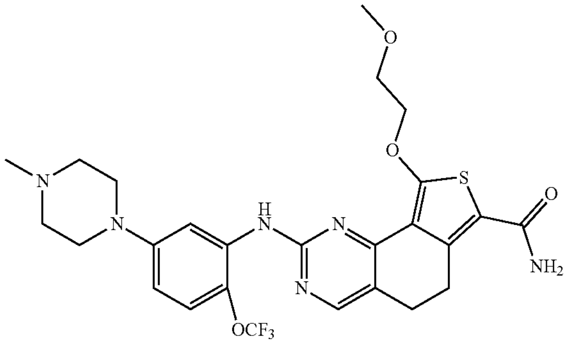

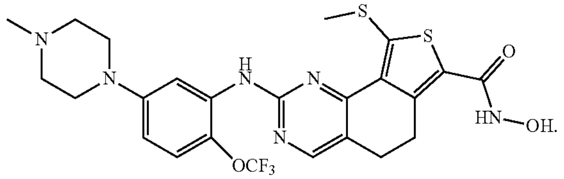

11. A method for treating solid tumors in a subject in need thereof, comprising: administering the compound or the pharmaceutically acceptable salt thereof according to claim 1 to the subject.

12. A method for selectively inhibiting PLK1 in a subject in need thereof, comprising: administering an effective amount of the compound or the pharmaceutically acceptable salt thereof according to claim 1 to the subject.

13. The method according to claim 11, wherein the solid tumor refers to colorectal cancer.

* * * * *